(12) United States Patent
Duckett et al.

(10) Patent No.: US 12,350,350 B2
(45) Date of Patent: Jul. 8, 2025

(54) HYPERPOLARISATION IN AQUEOUS MEDIA VIA SABRE

(71) Applicant: UNIVERSITY OF YORK, York (GB)

(72) Inventors: Simon Benedict Duckett, North Yorkshire (GB); Wissam Iali, North Yorkshire (GB); Maria-Alexandra Olaru, North Yorkshire (GB)

(73) Assignee: UNIVERSITY OF YORK (GB)

( * ) Notice: Subject to any disclaimer, the term of this patent is extended or adjusted under 35 U.S.C. 154(b) by 329 days.

(21) Appl. No.: 16/491,814

(22) PCT Filed: Mar. 7, 2018

(86) PCT No.: PCT/GB2018/050573
§ 371 (c)(1),
(2) Date: Sep. 6, 2019

(87) PCT Pub. No.: WO2018/162895
PCT Pub. Date: Sep. 13, 2018

(65) Prior Publication Data
US 2020/0397923 A1    Dec. 24, 2020

(30) Foreign Application Priority Data
Mar. 7, 2017 (GB) .................................... 1703658

(51) Int. Cl.
*A61K 49/10* (2006.01)
*G01R 33/28* (2006.01)
*G01R 33/56* (2006.01)

(52) U.S. Cl.
CPC .......... *A61K 49/106* (2013.01); *G01R 33/282* (2013.01); *G01R 33/5601* (2013.01)

(58) Field of Classification Search
CPC .............. G01R 33/5601; G01R 33/282; G01R 33/5305; A61K 49/106; A61K 49/10
See application file for complete search history.

(56) References Cited

U.S. PATENT DOCUMENTS

| 2008/0293605 | A1 | 11/2008 | Gibis et al. | |
| 2009/0016964 | A1* | 1/2009 | Kalechofsky | A61K 49/1806 424/9.3 |
| 2011/0178393 | A1* | 7/2011 | Reineri | A61K 49/10 600/420 |
| 2011/0274626 | A1* | 11/2011 | Duckett | G01R 33/5601 424/9.361 |

FOREIGN PATENT DOCUMENTS

WO    2010/037771 A1    4/2010

OTHER PUBLICATIONS

Haifeng Zeng et al.; "Achieving 1% NMR polarization in water in less than 1 min using Sabre"; Journal of Magnetic Resonance; vol. 246; (8 pages).
PCT International Search Report and PCT Written Opinion for PCT International Patent Application No. PCT/GB2018/050573; date of mailing Sep. 5, 2018; (28 pages).

* cited by examiner

*Primary Examiner* — Michael G. Hartley
*Assistant Examiner* — Leah H Schlientz
(74) *Attorney, Agent, or Firm* — K&L GATES LLP

(57) ABSTRACT

There is described a method for the preparation of an aqueous magnetic resonance imaging medium, said method comprising the steps of: •(i) preparing a multiphasic solvent system comprising an aqueous component and a non-aqueous component, said solvent comprising a target substrate and a SABRE hyperpolarisation transfer catalyst; •(ii) adding $H_2$ or parahydrogen gas; •(iii) agitating the solvent system to form an emulsion thereby transferring the spin order from the hyperpolarisation transfer catalyst to the target substrate; •(v) adding a solvent phase-separation promoter; and •(vi) separating the non-aqueous component and the aqueous component wherein the aqueous component contains the hyperpolarised target substrate and provides the aqueous magnetic resonance imaging medium.

20 Claims, 50 Drawing Sheets

Figure 101:
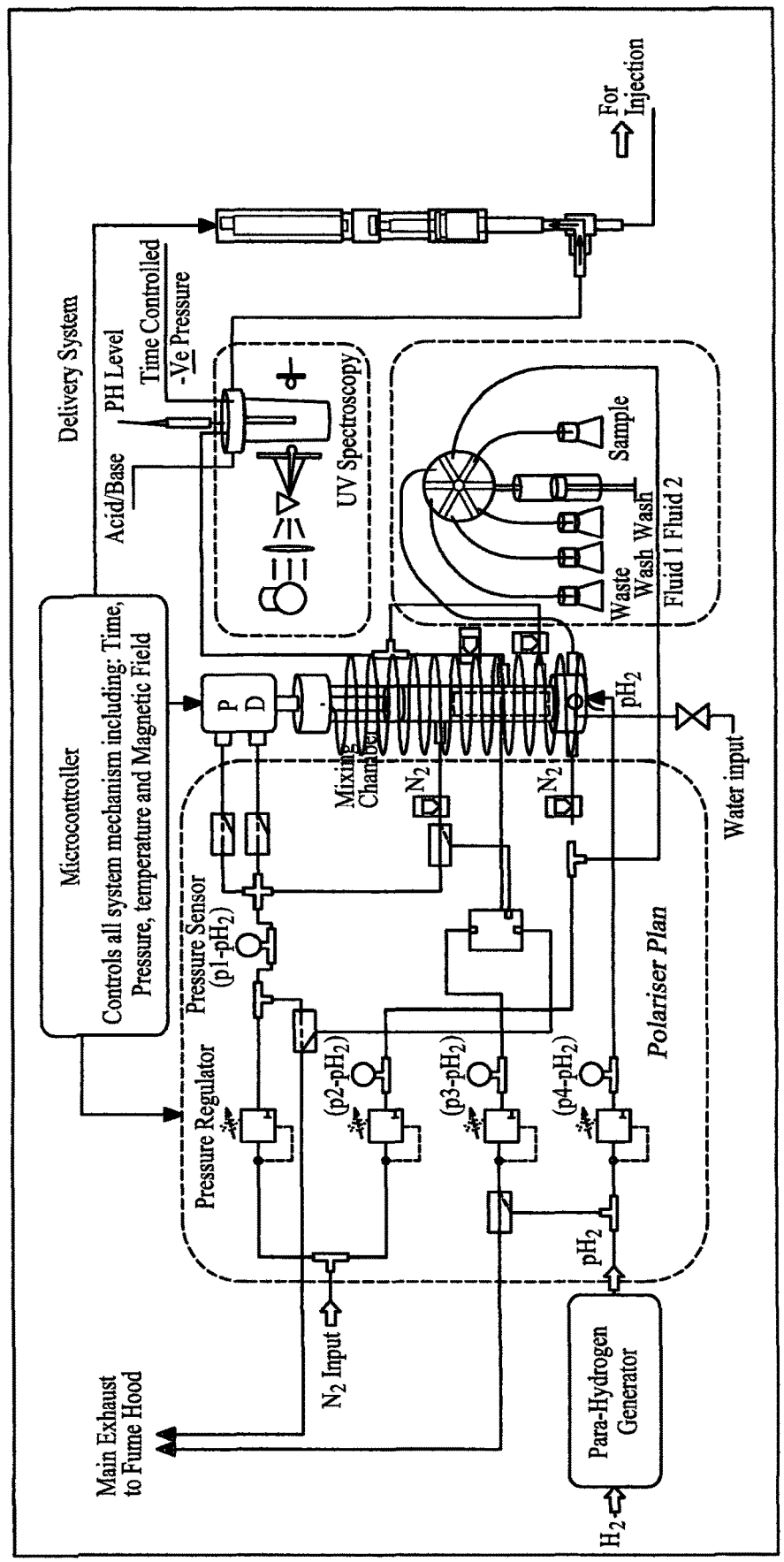

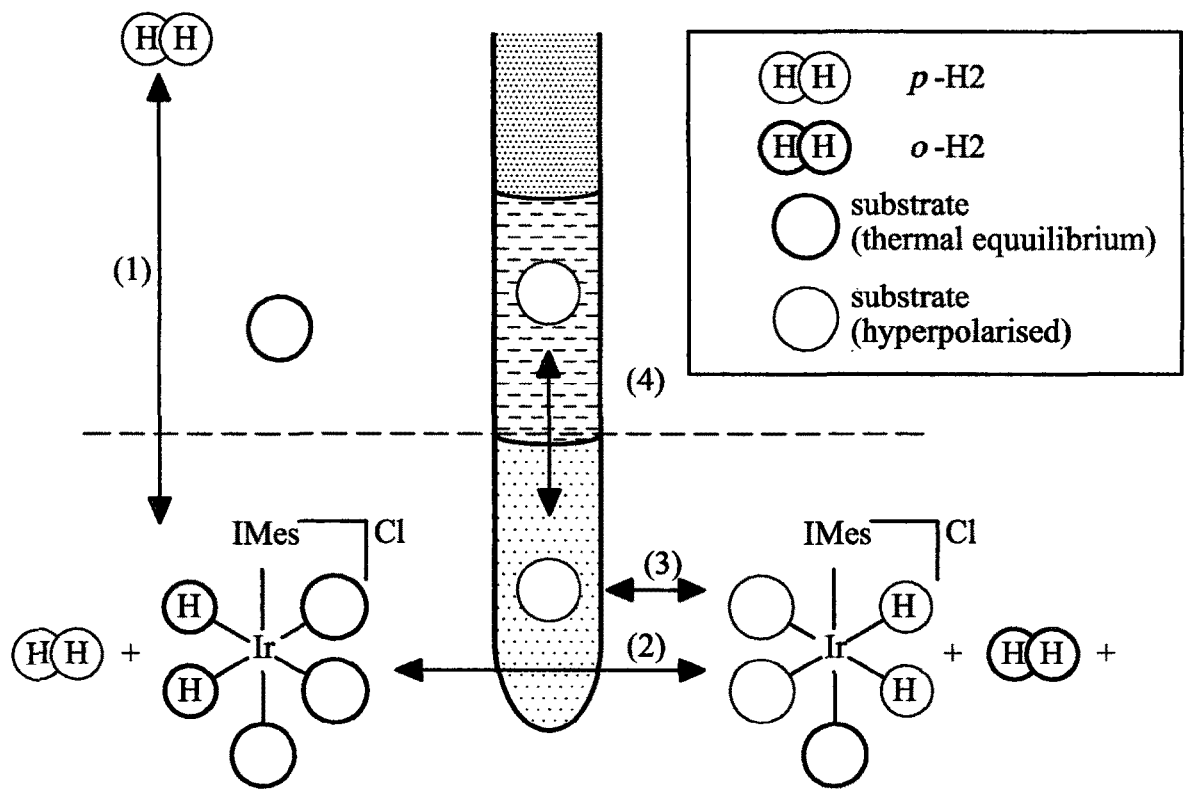
Scheme 1
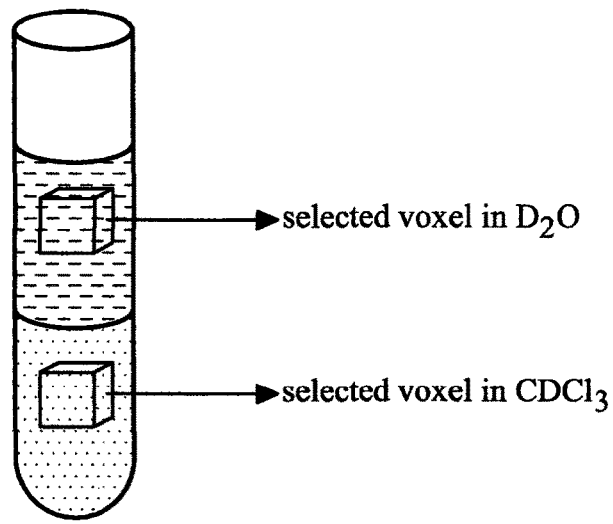
Figure S1

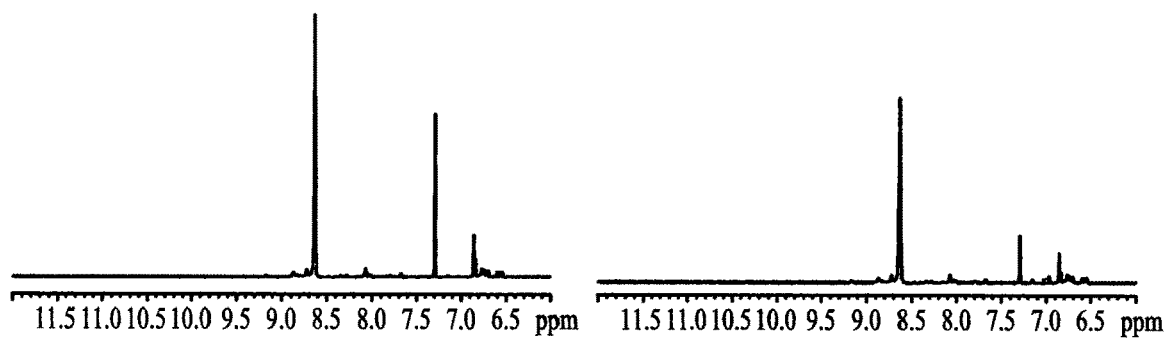
Figure S2     Figure S3
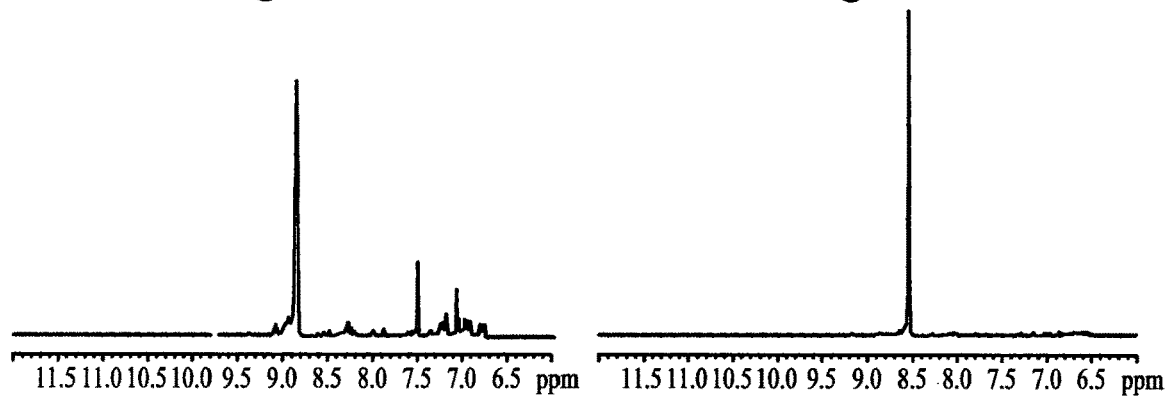
Figure S4     Figure S5

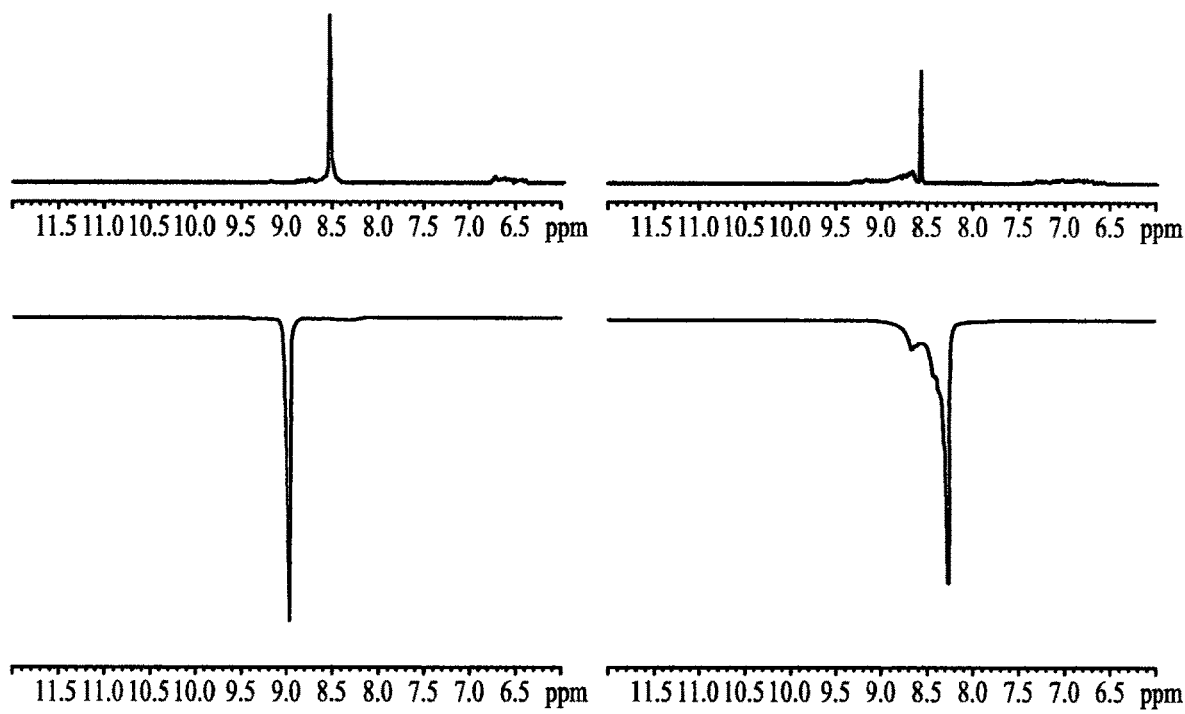
Figure S6        Figure S7
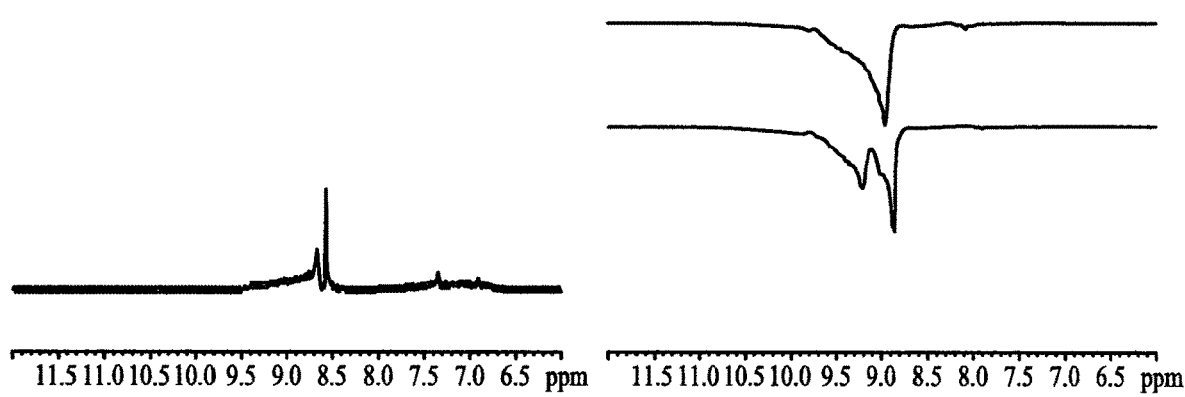
Figure S8        Figure S9

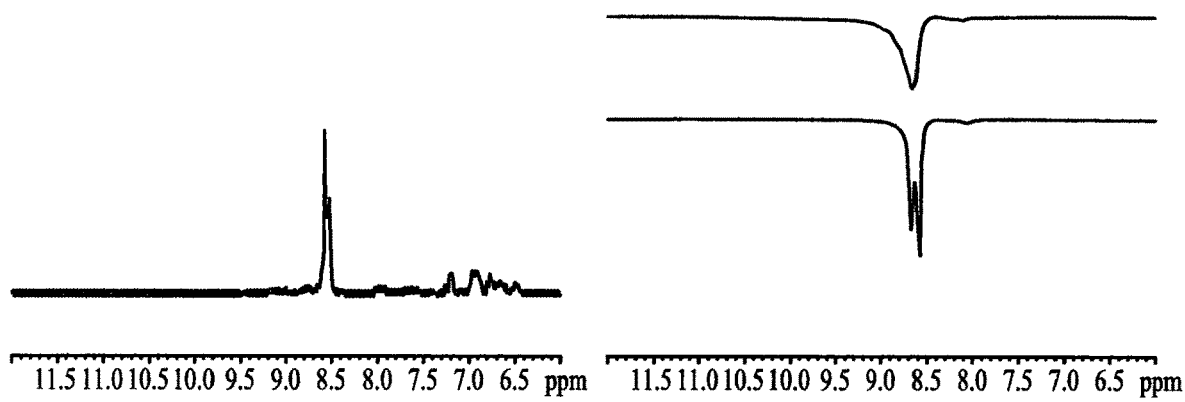
Figure S10
Figure S11
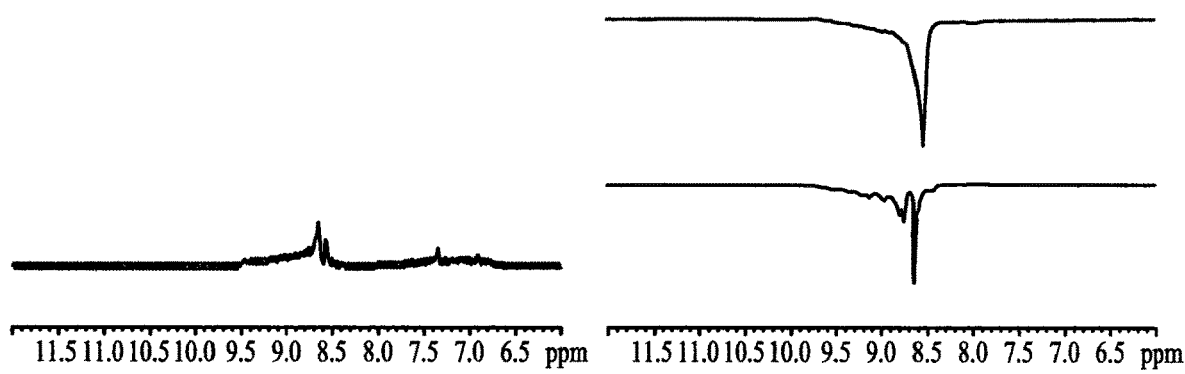
Figure S12
Figure S13

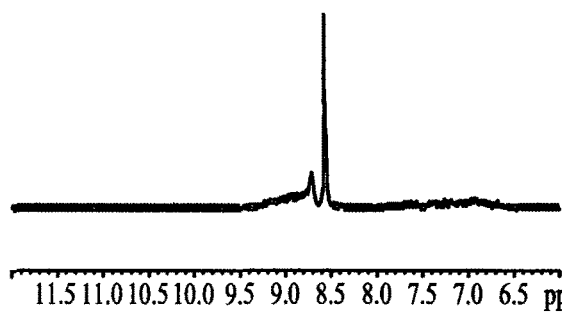
Figure S14
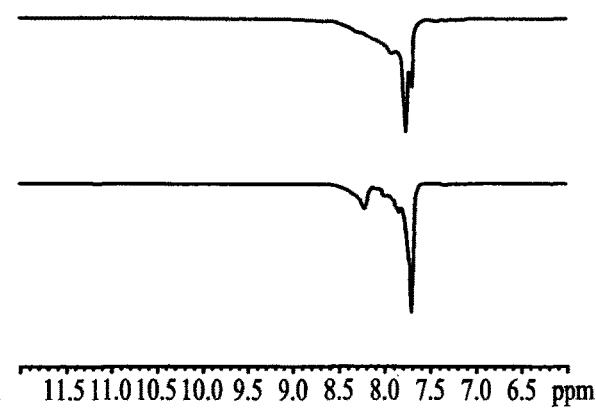
Figure S15
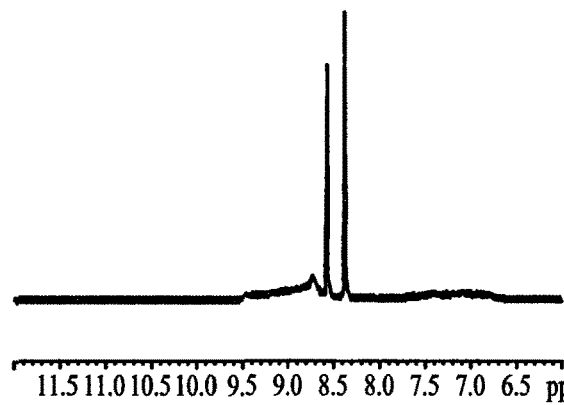
Figure S16
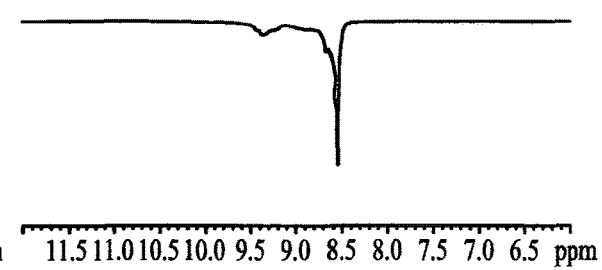
Figure S17

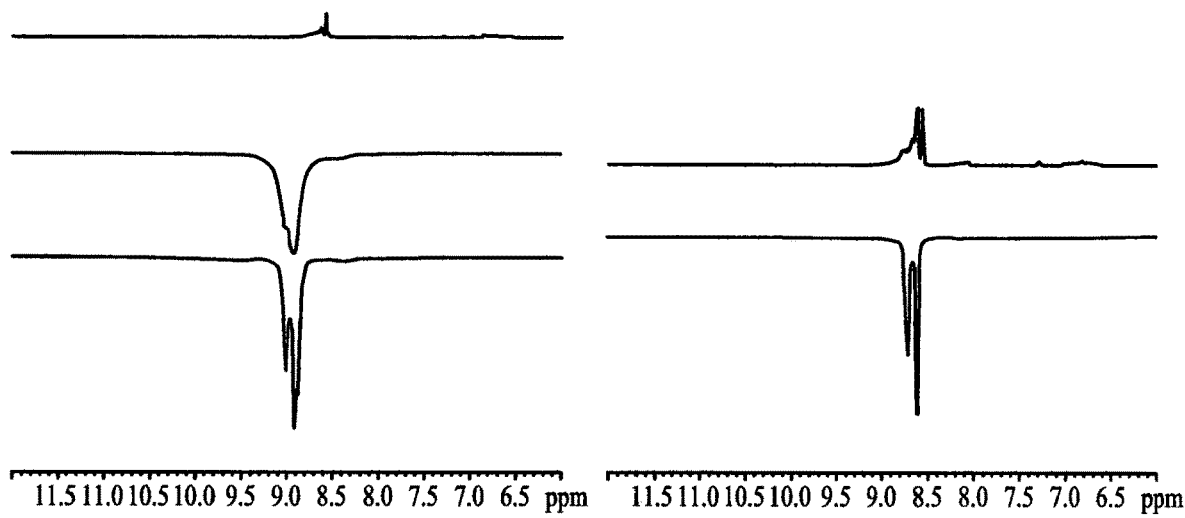
Figure S18    Figure S19
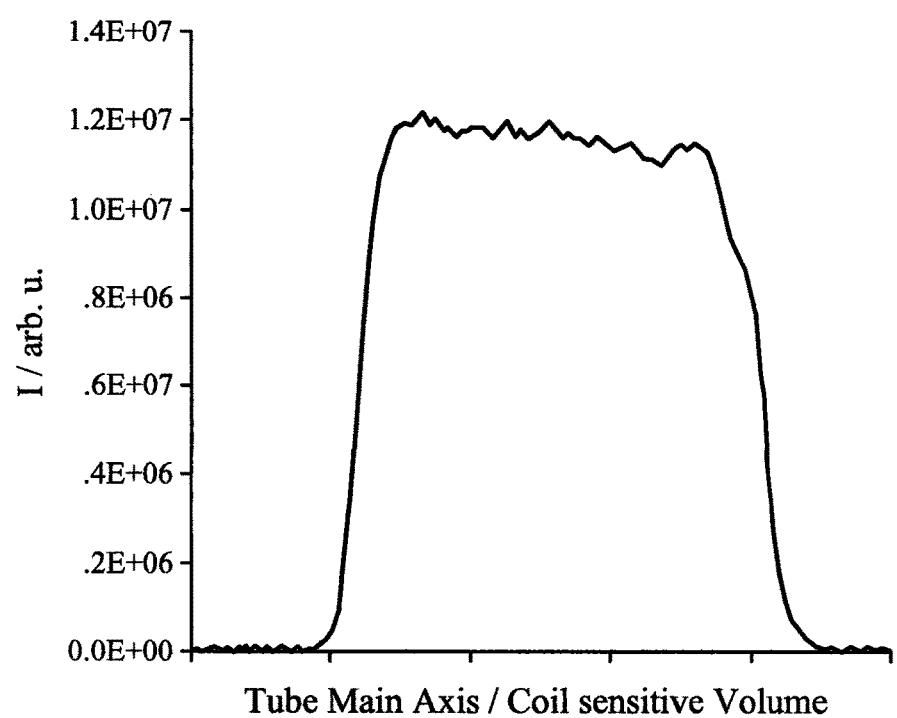
Figure S20

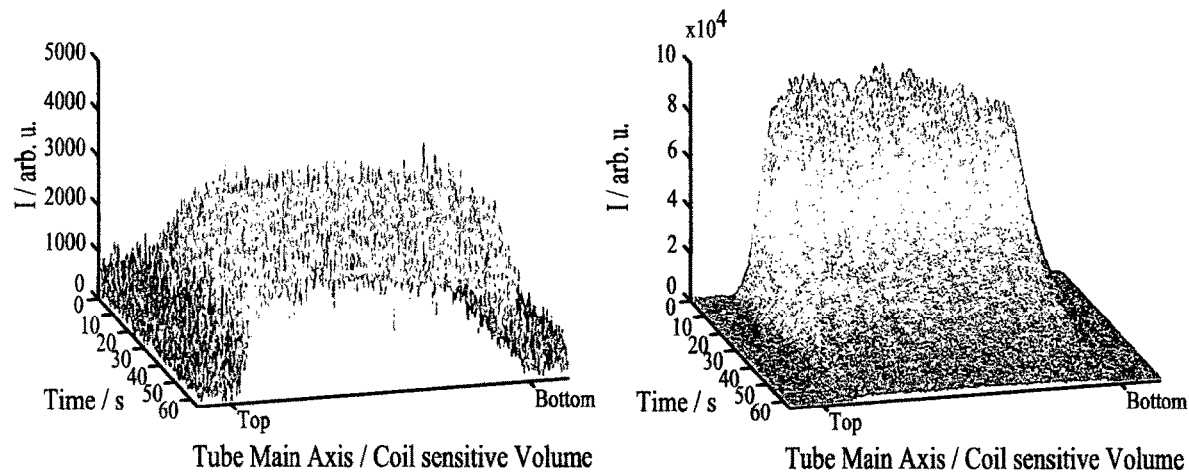
Figure S21
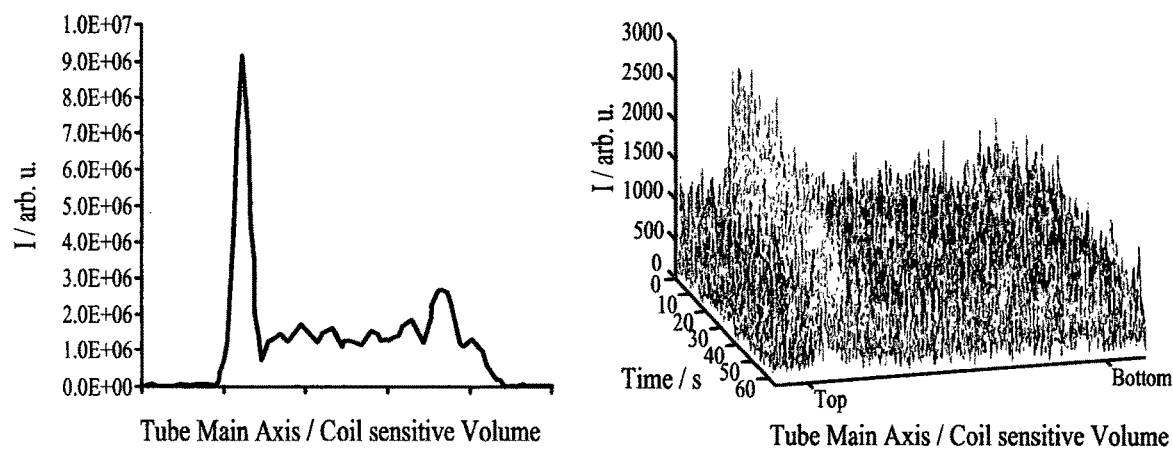
Figure S22

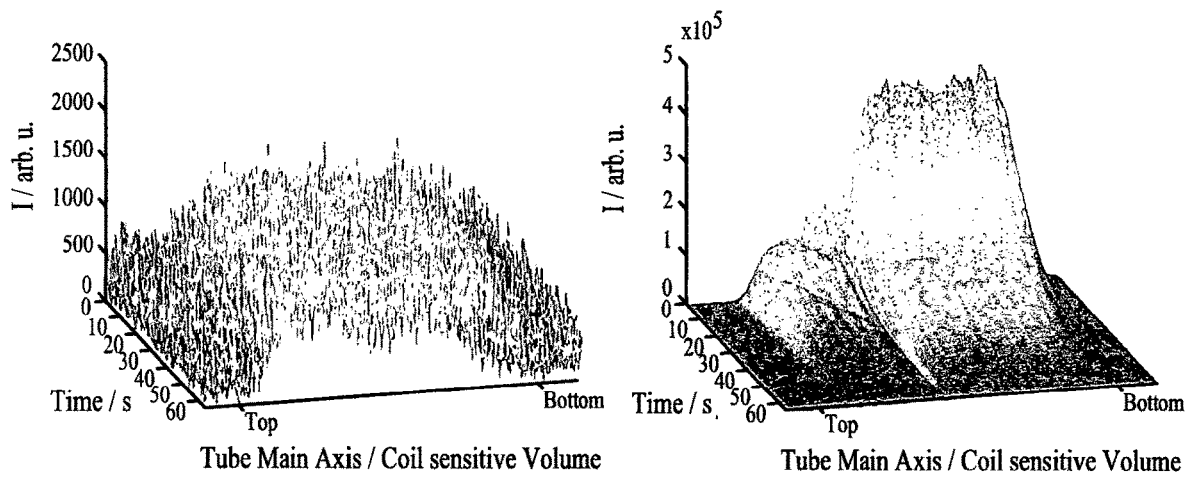
Figure S23
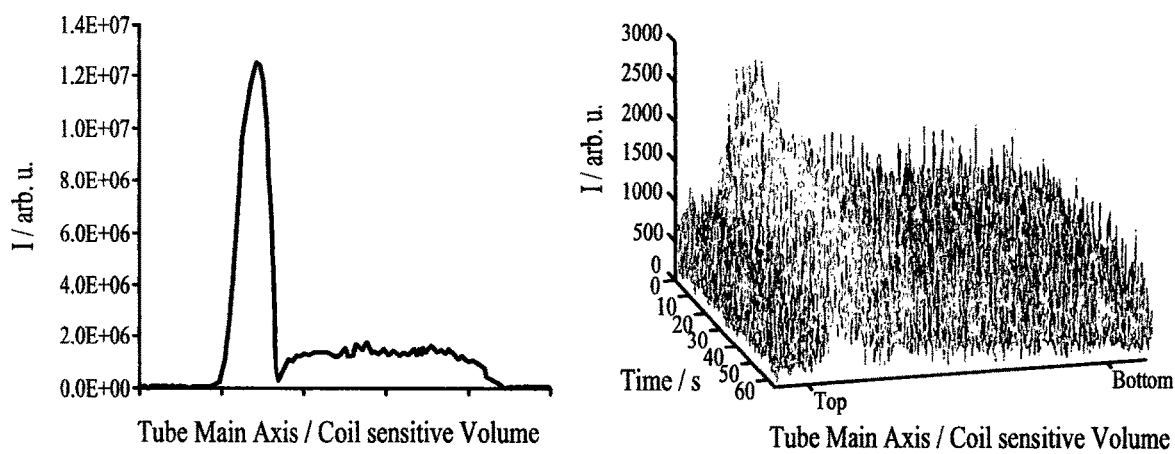
Figure S24

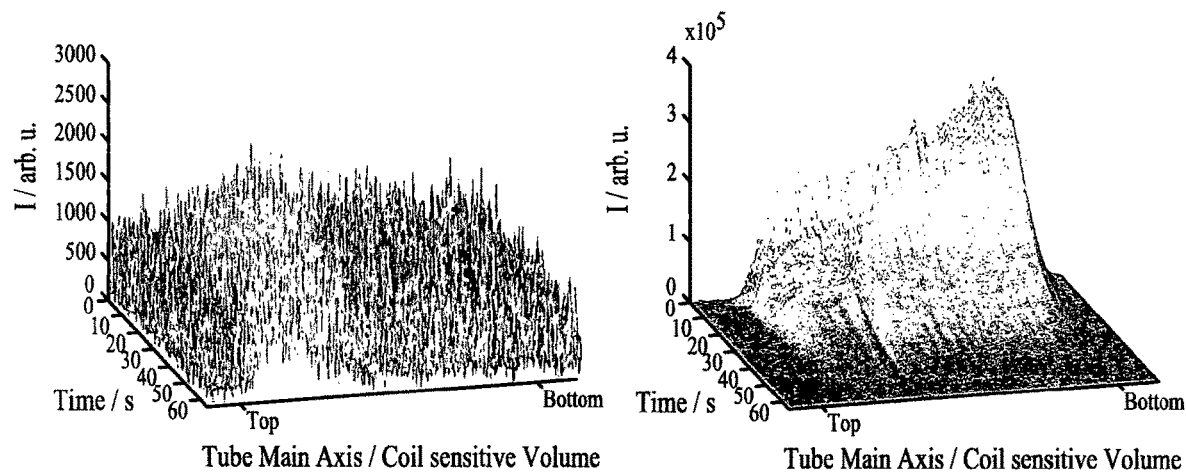
Figure S25
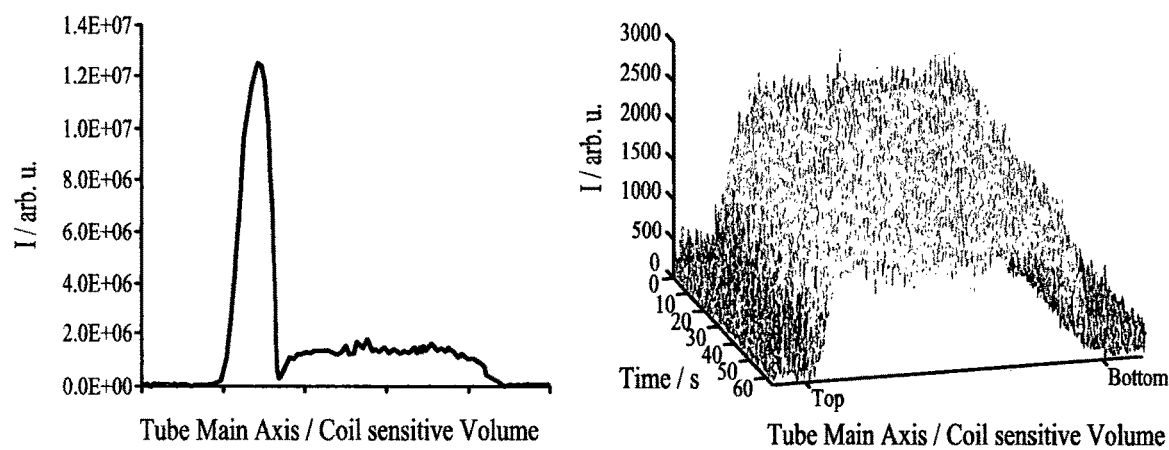
Figure S26

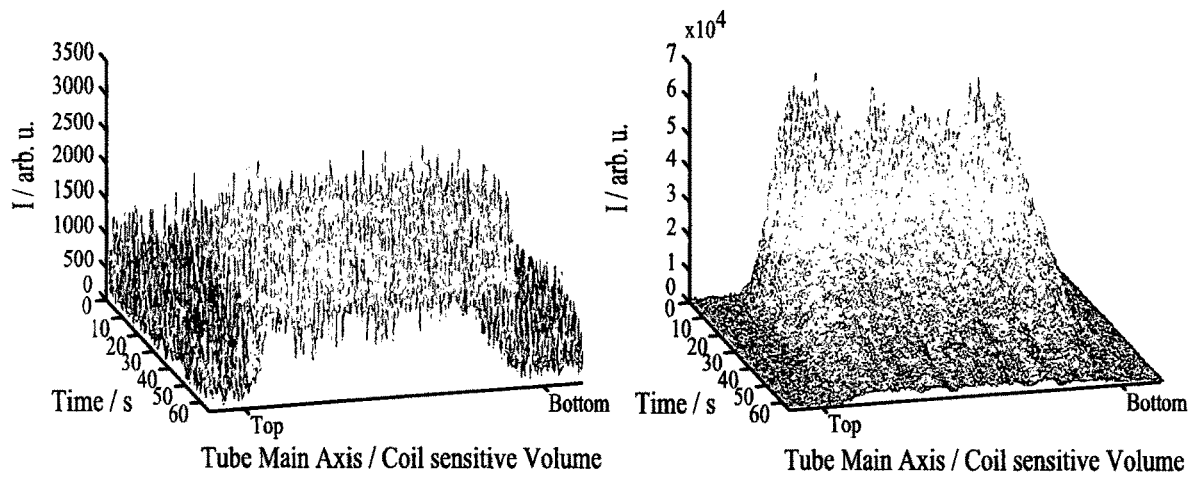
Figure S27
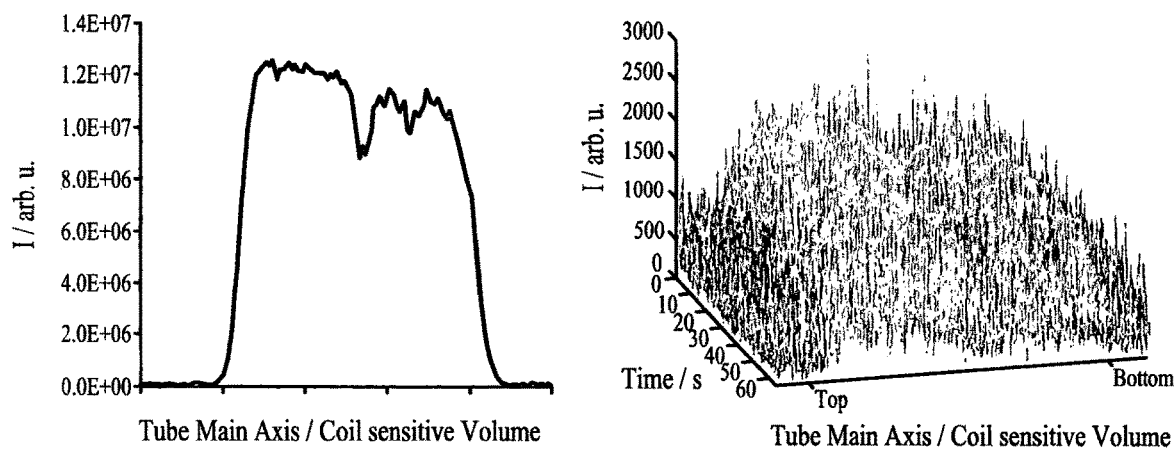
Figure S28

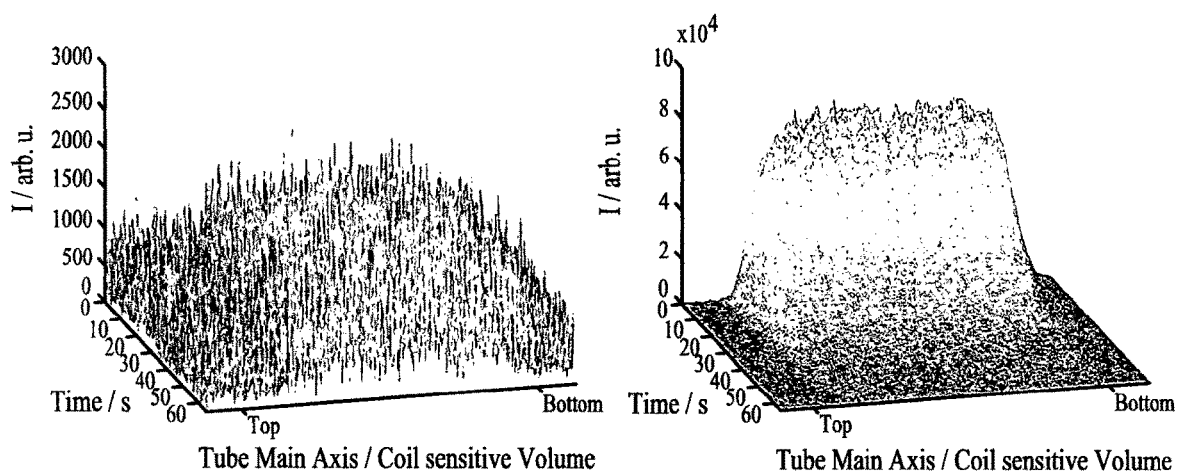
Figure S29
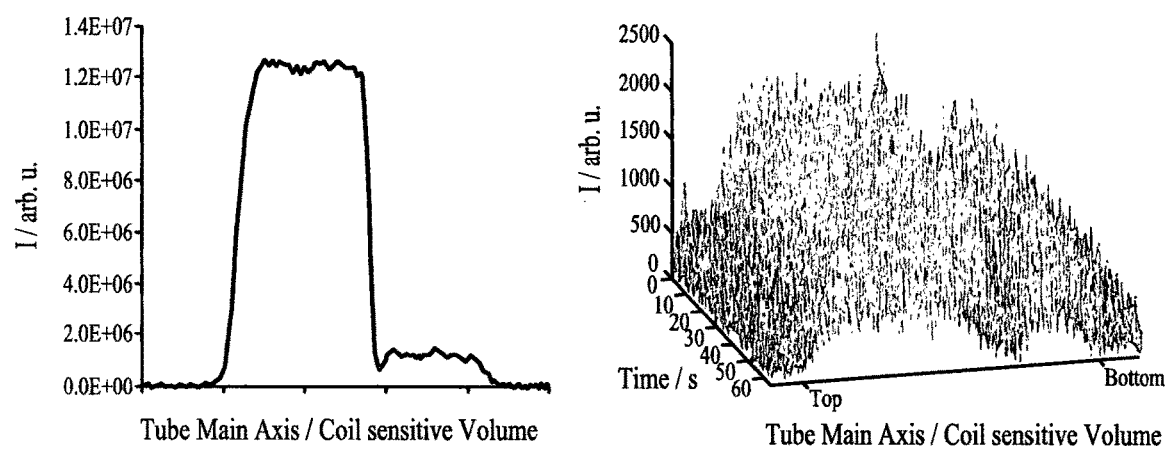
Figure S30

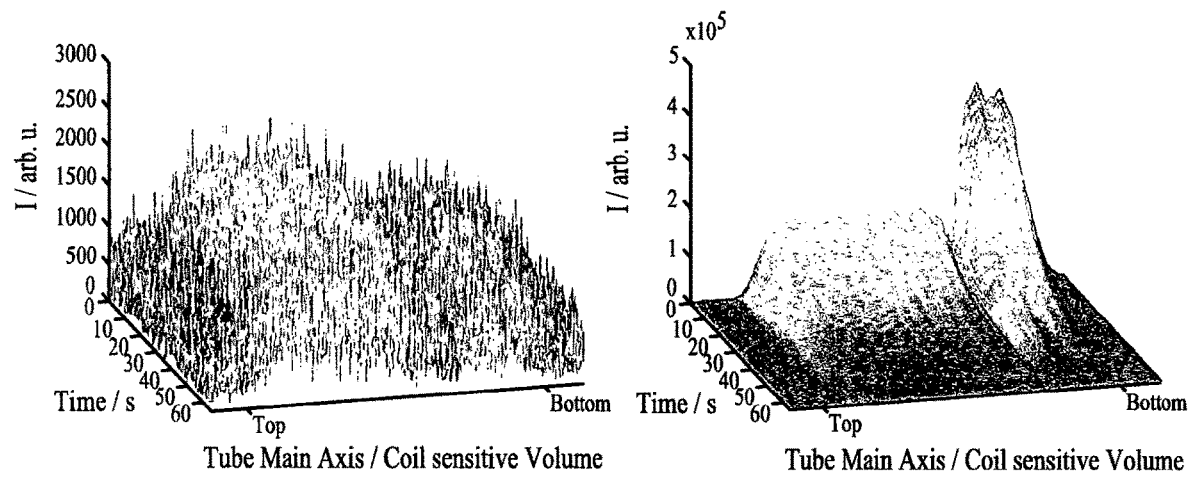
Figure S31
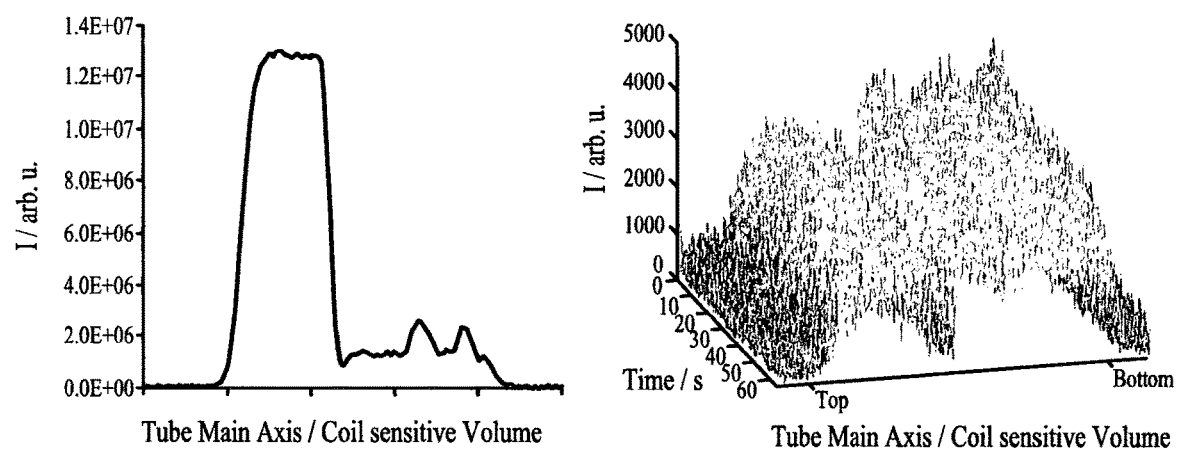
Figure S32

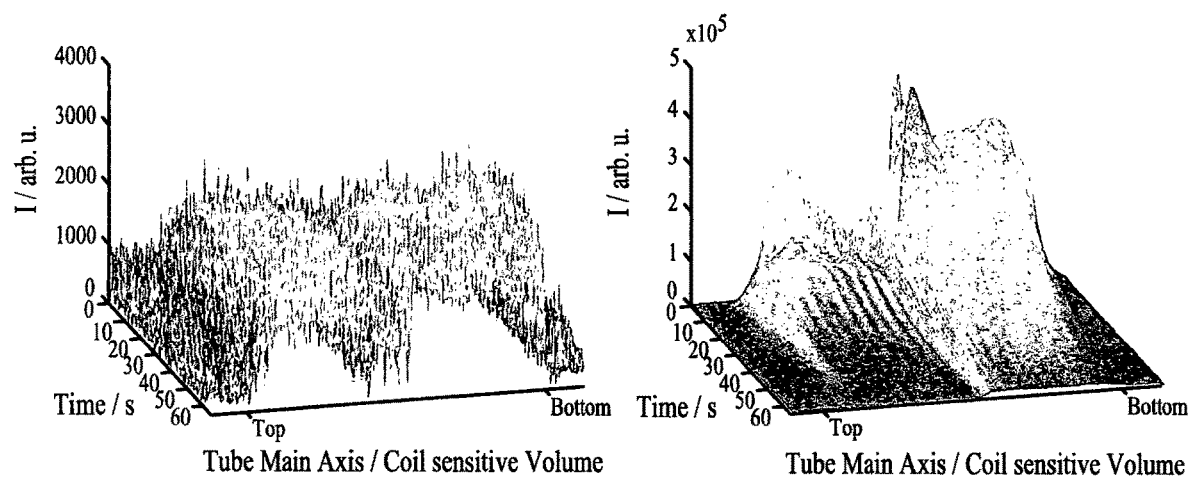
Figure S33
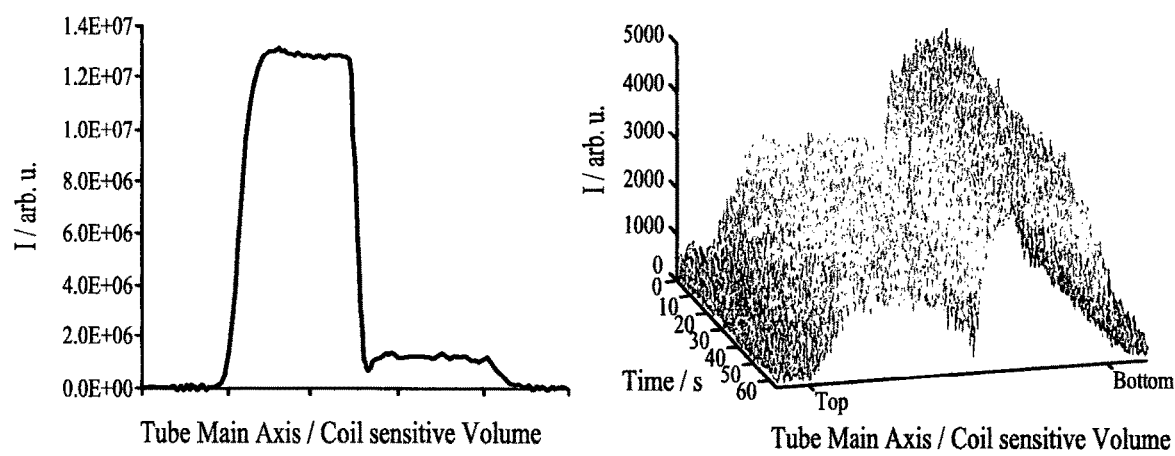
Figure S34

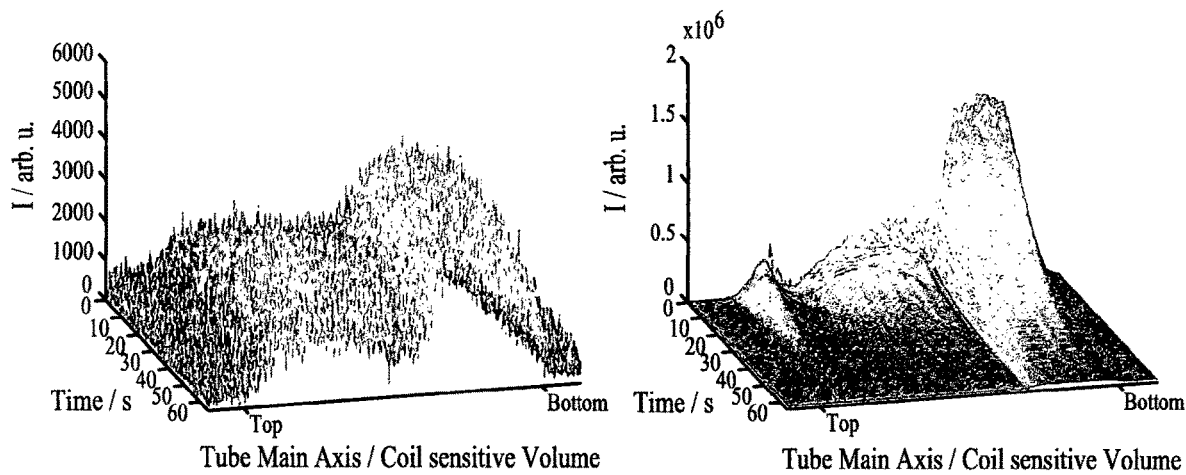
Figure S35
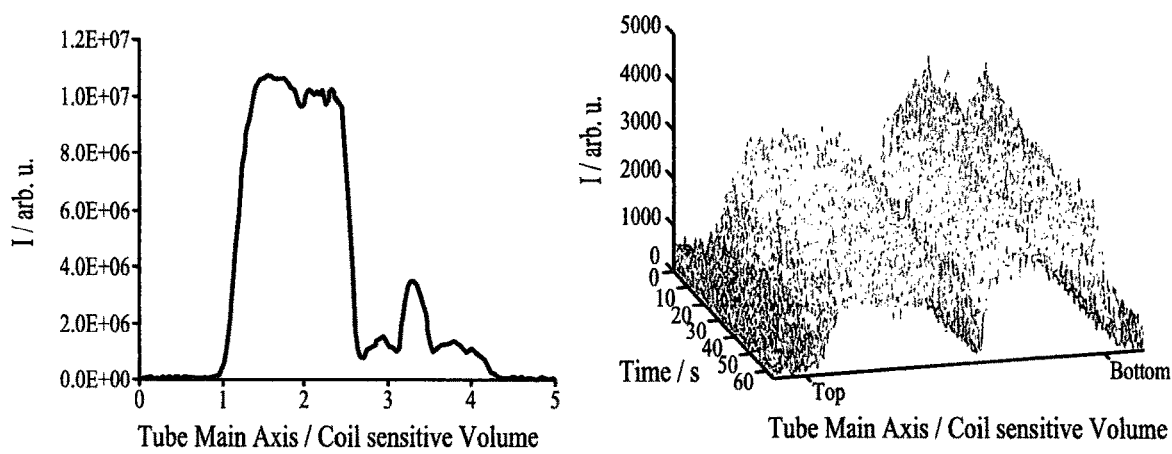
Figure S36

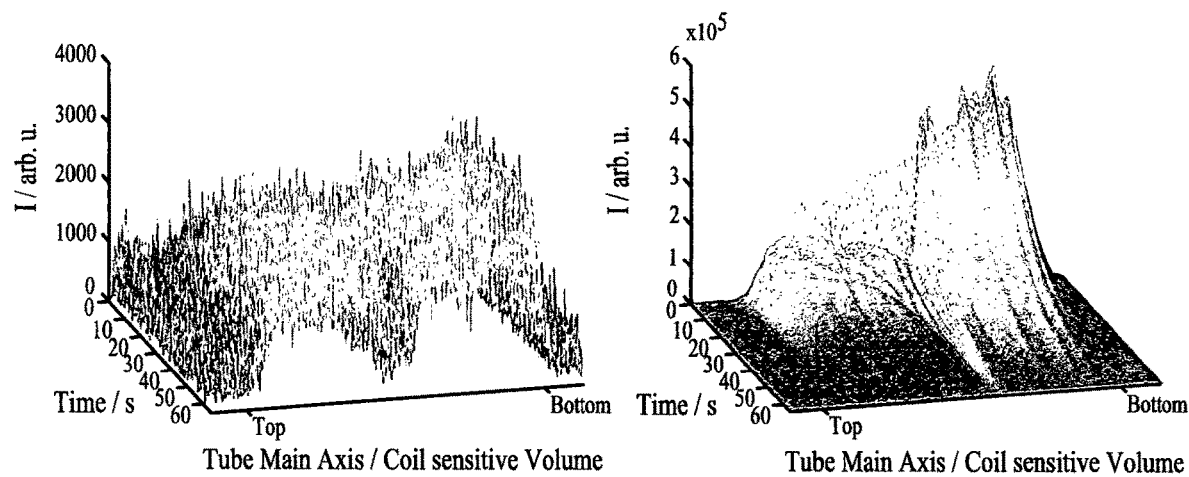
Figure S37
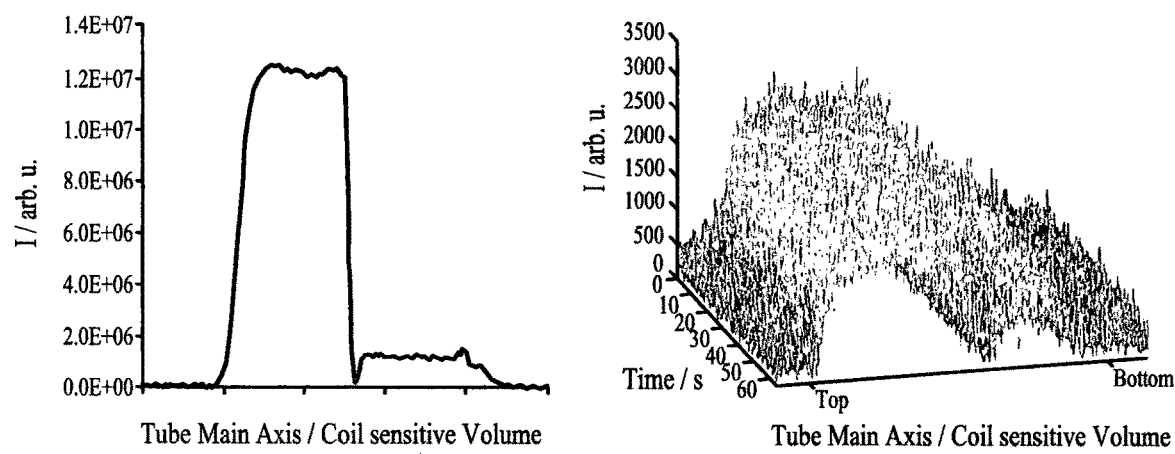
Figure S38

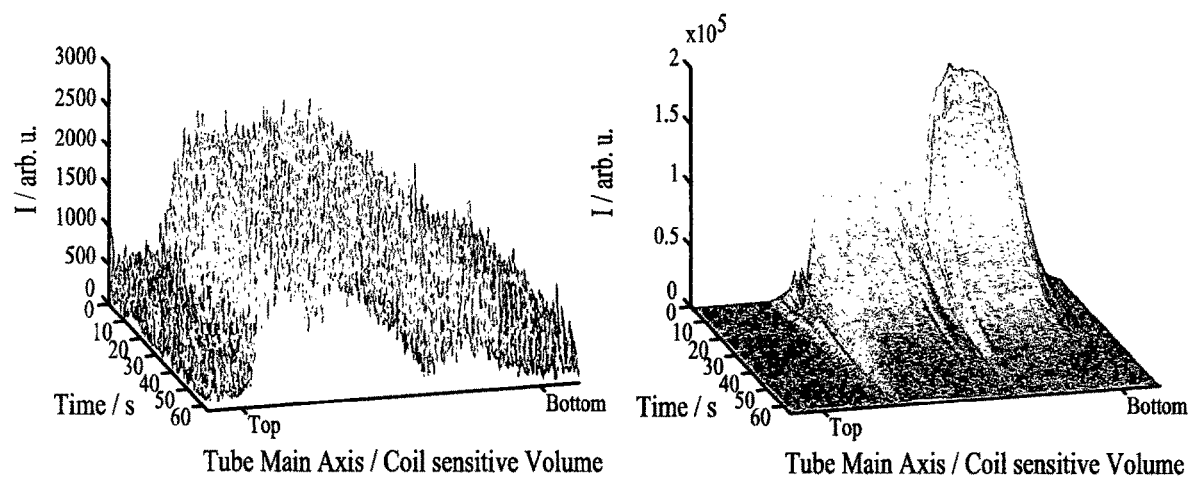
Figure S39
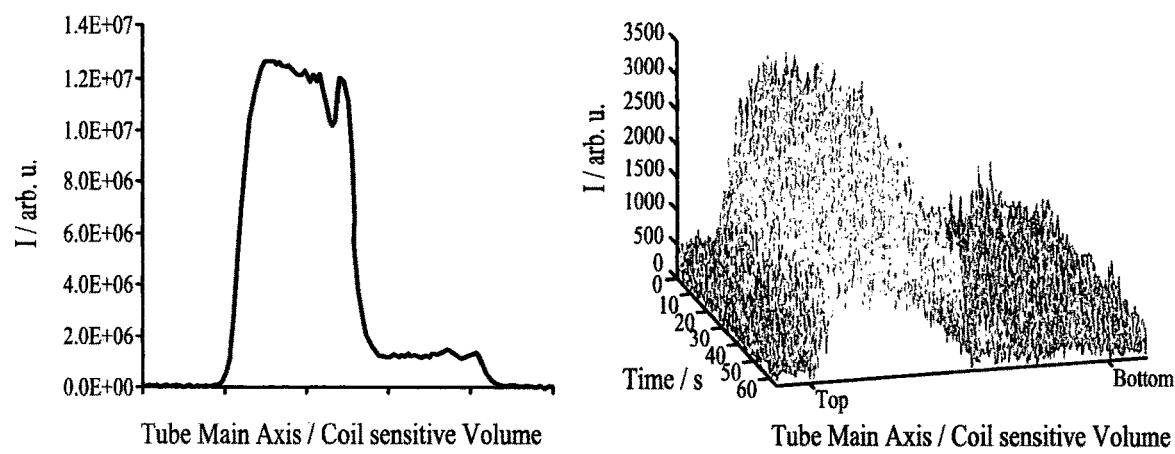
Figure S40

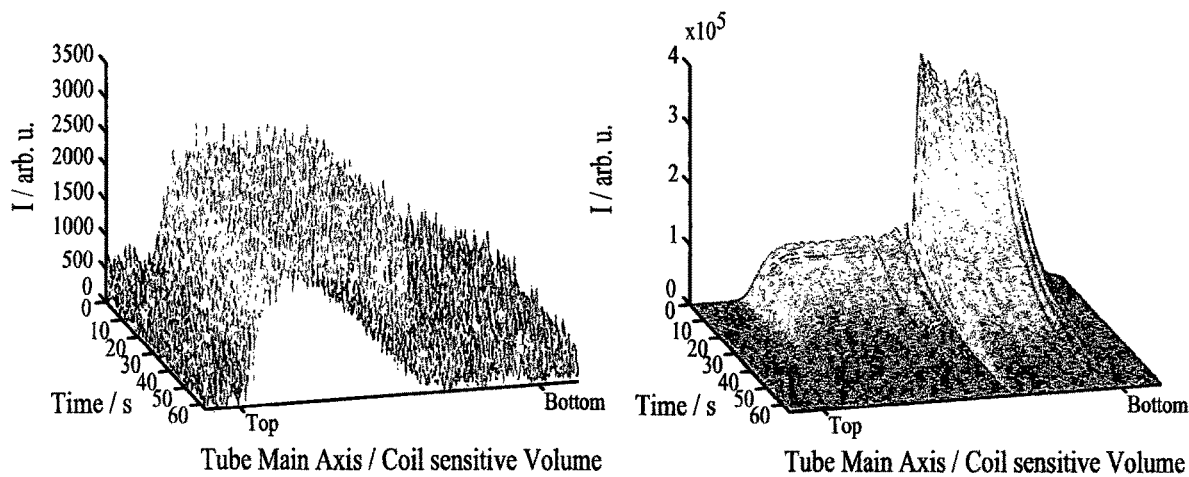
Figure S41
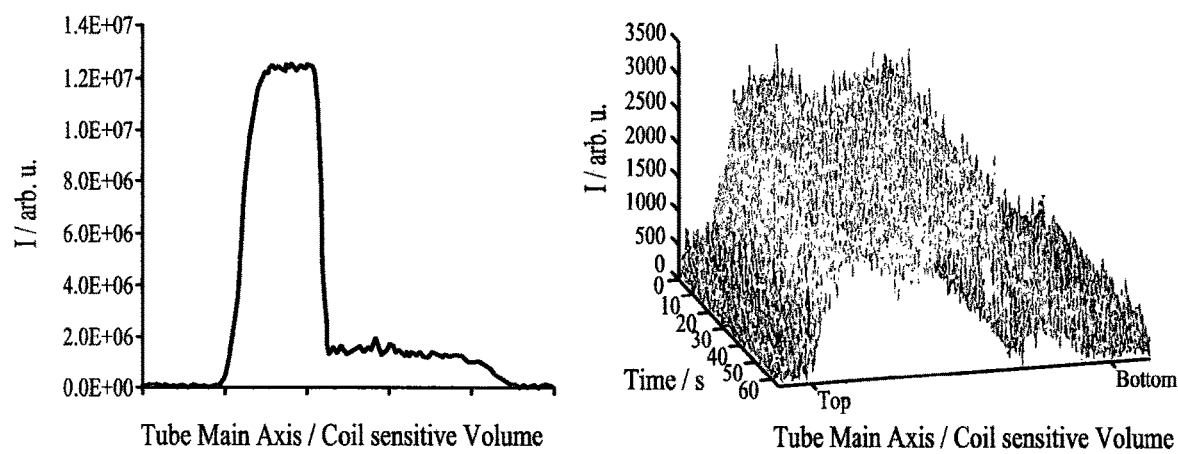
Figure S42

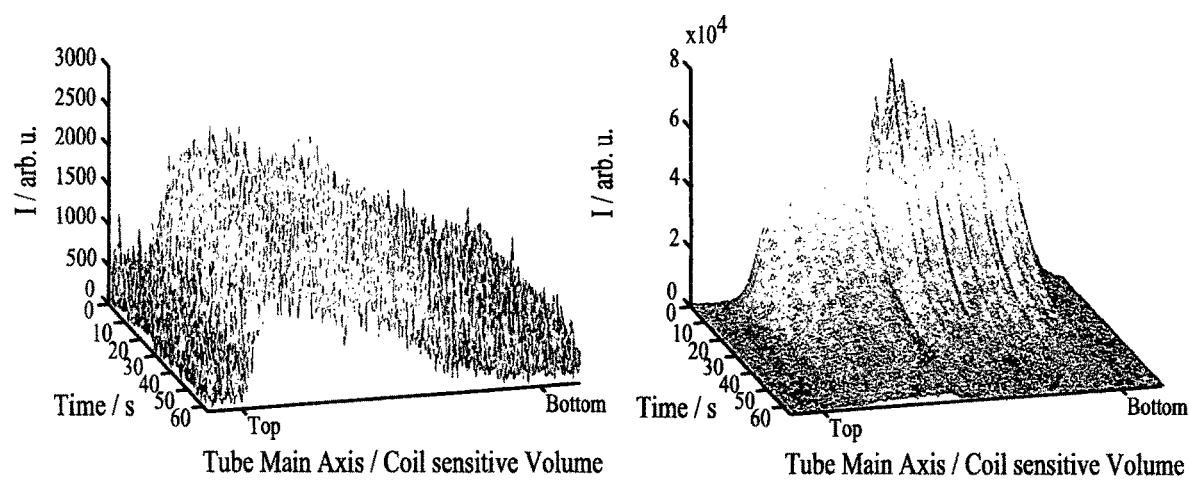
Figure S43
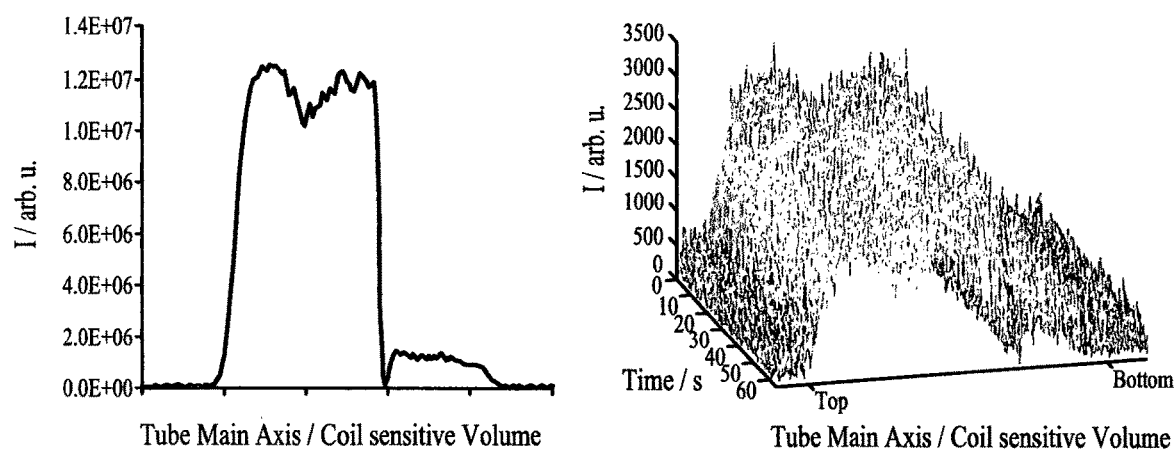
Figure S44

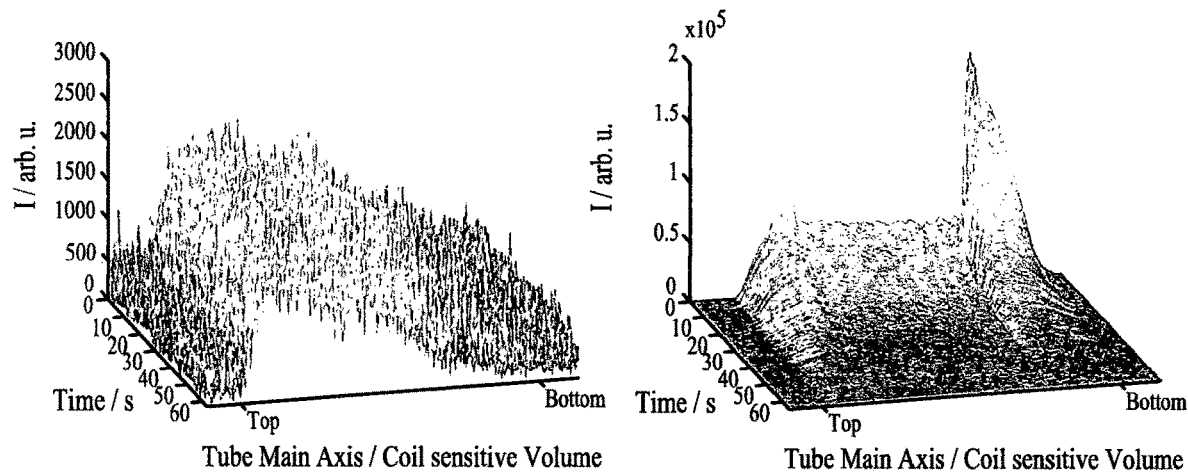
Figure S45
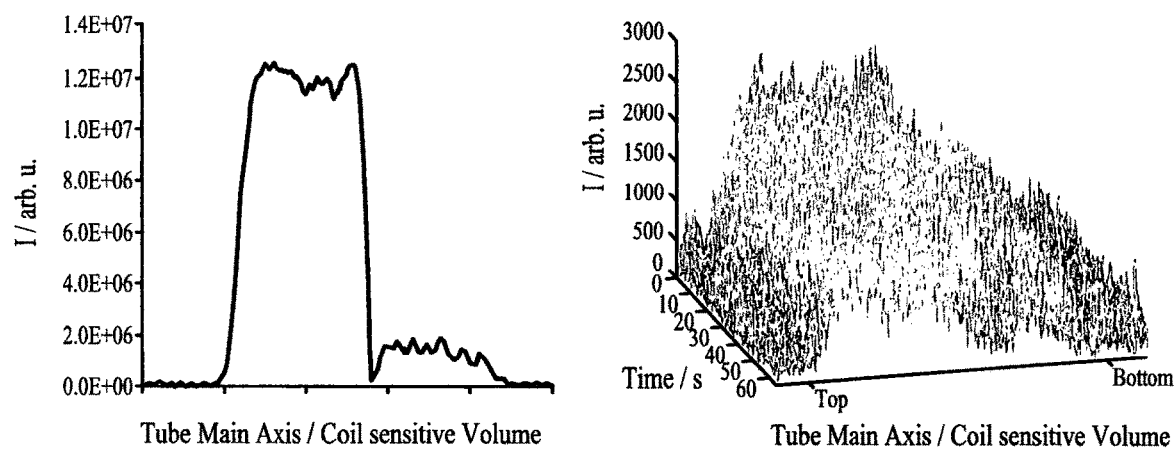
Figure S46

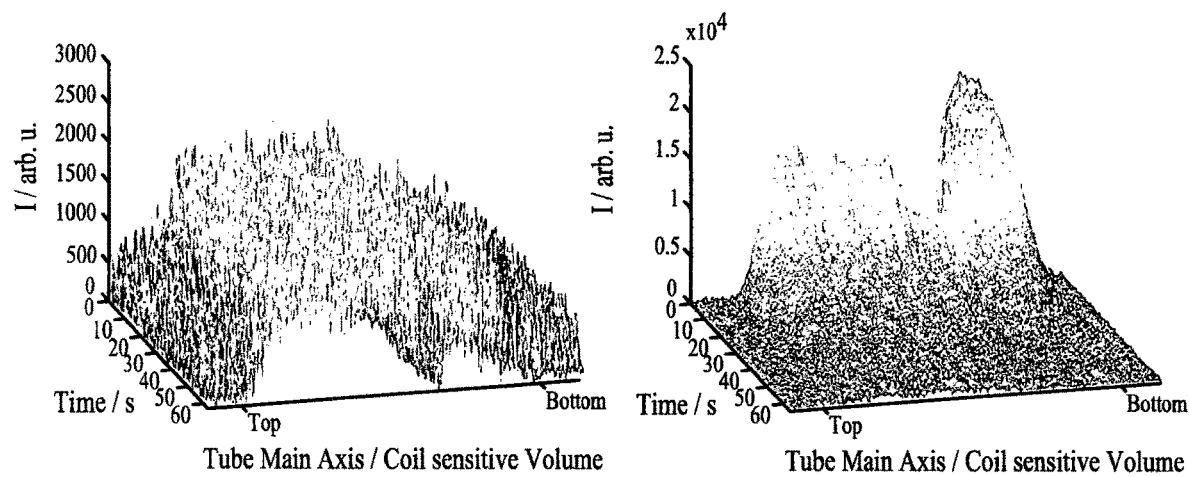
Figure S47
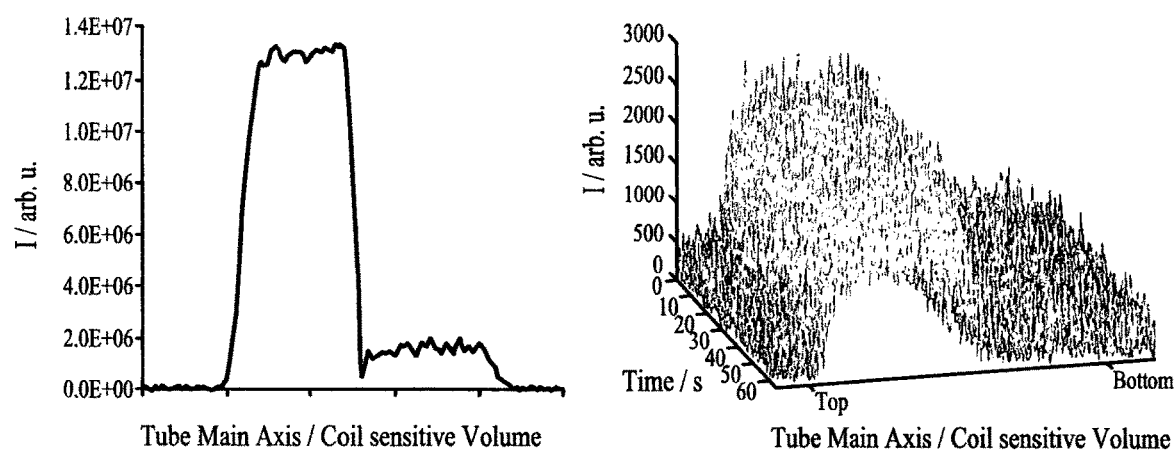
Figure S48

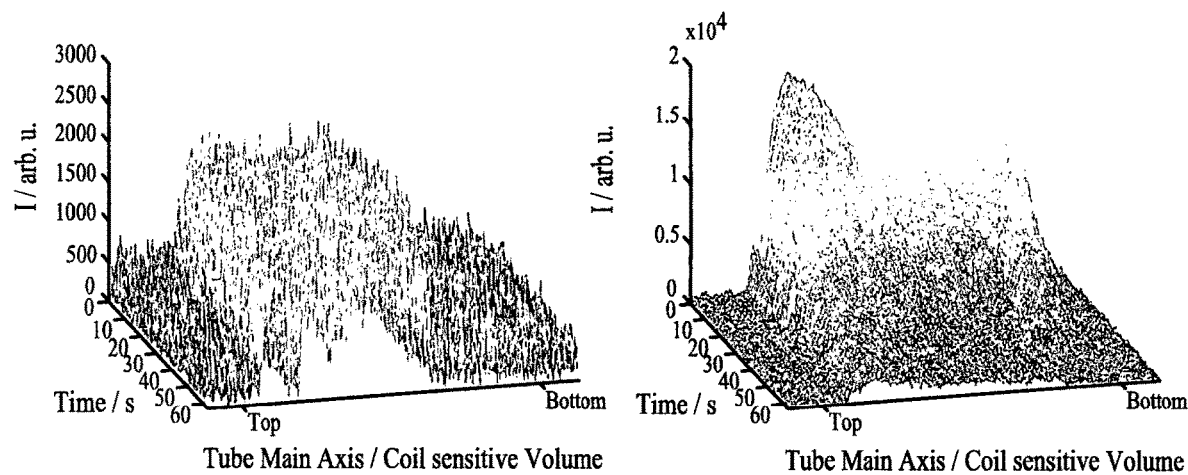
Figure S49
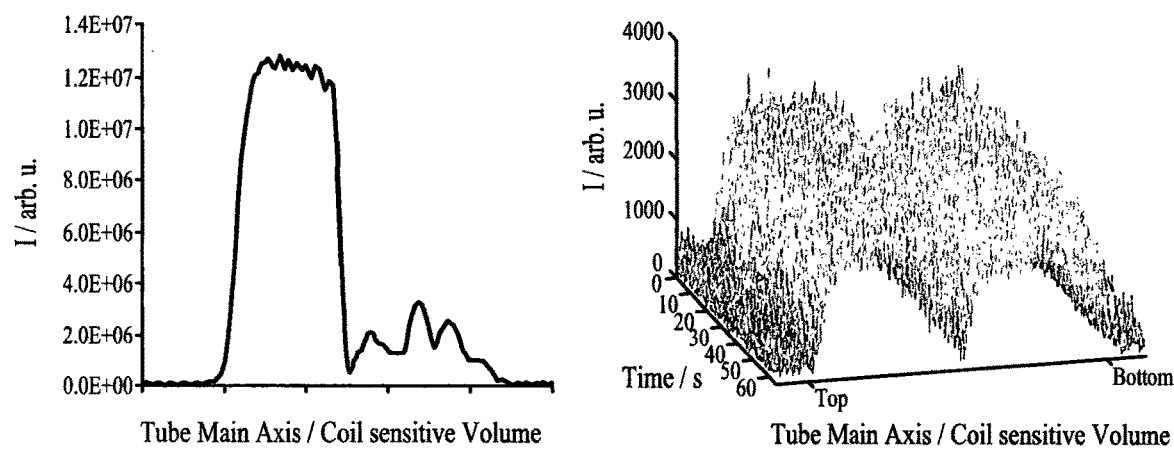
Figure S50

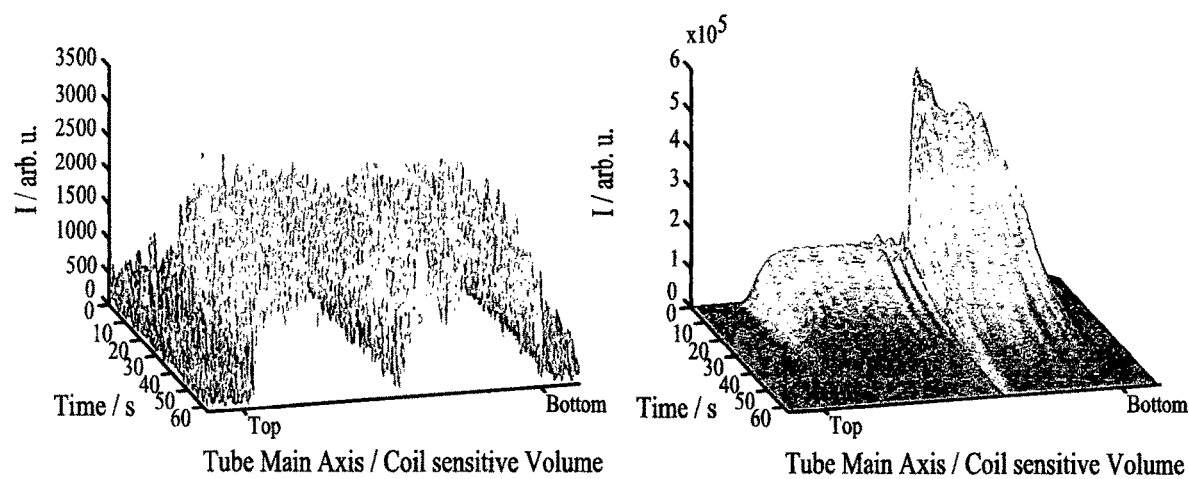
Figure S51
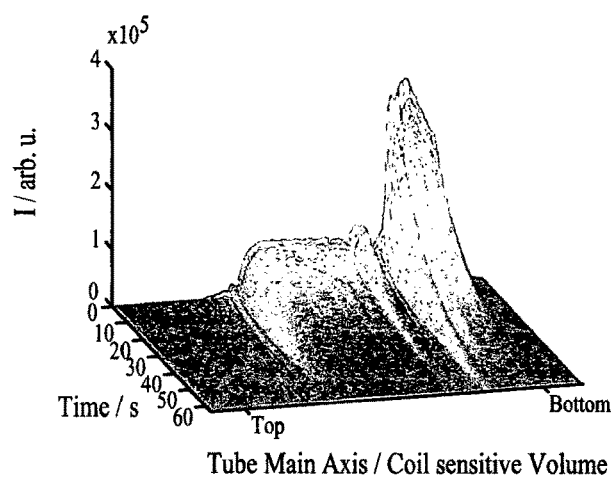
Figure S52

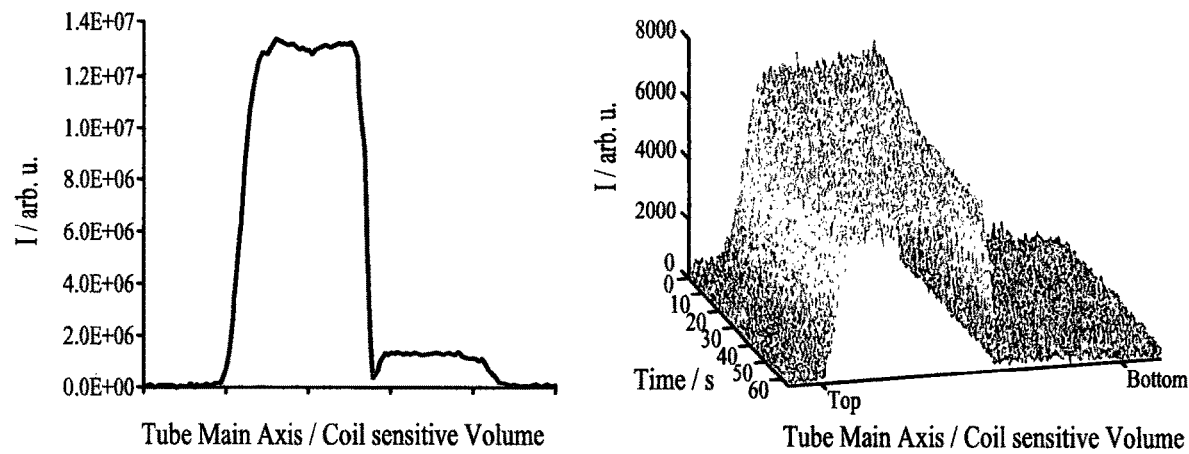
Figure S53
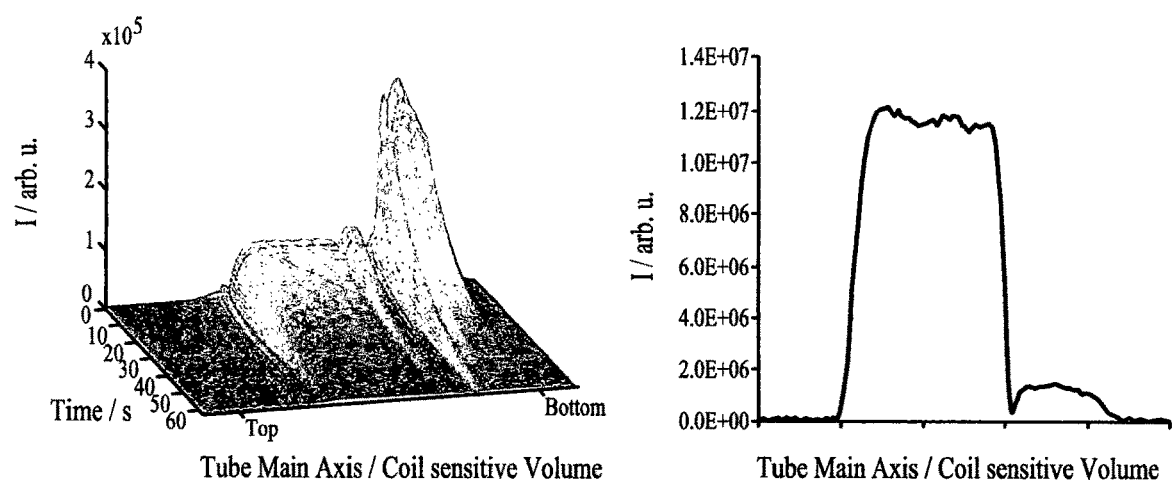
Figure S54
Figure S55

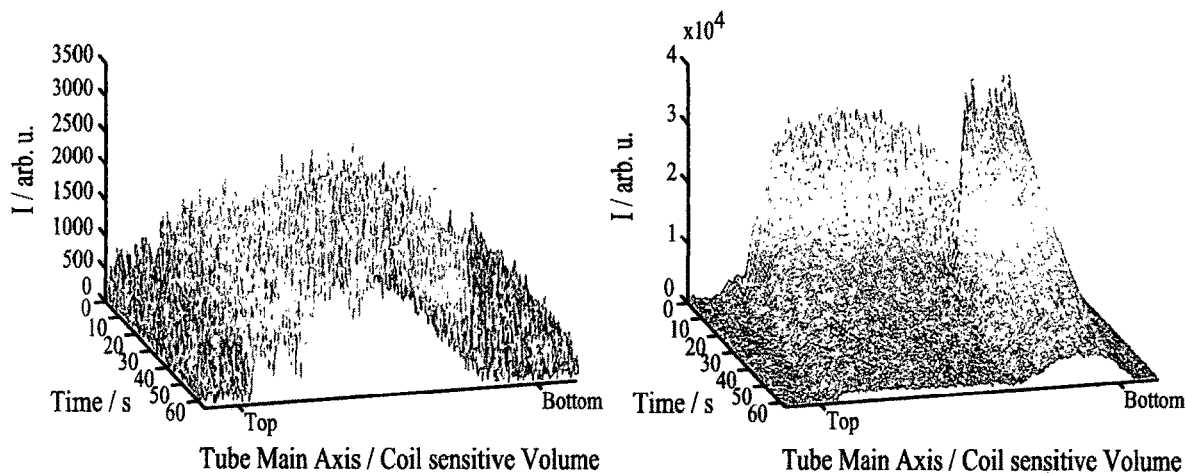
Figure S56
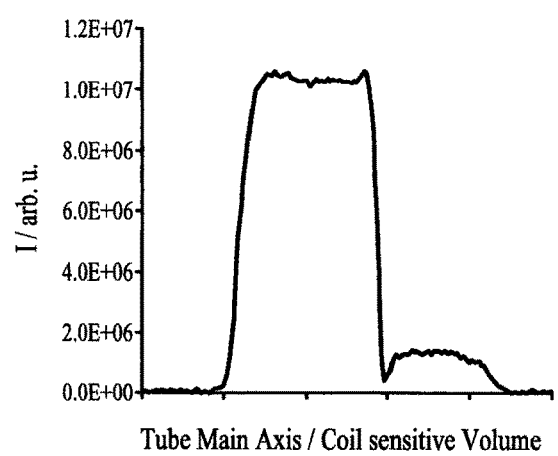
Figure S57

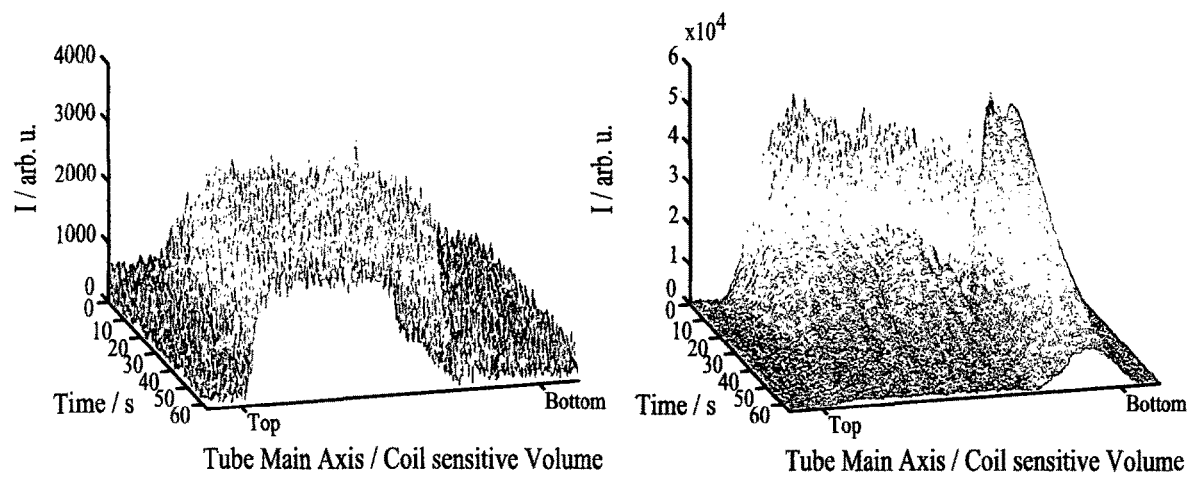
Figure S58
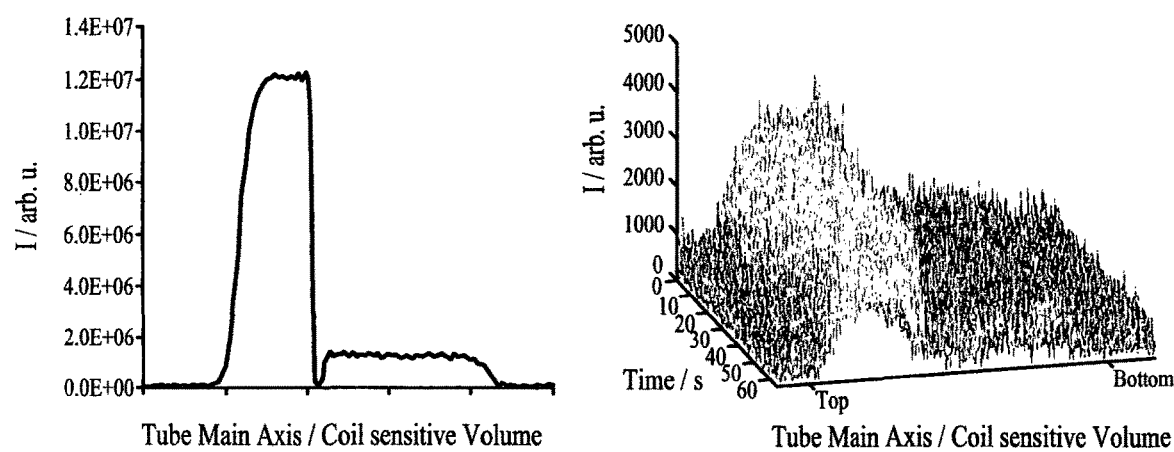
Figure S59

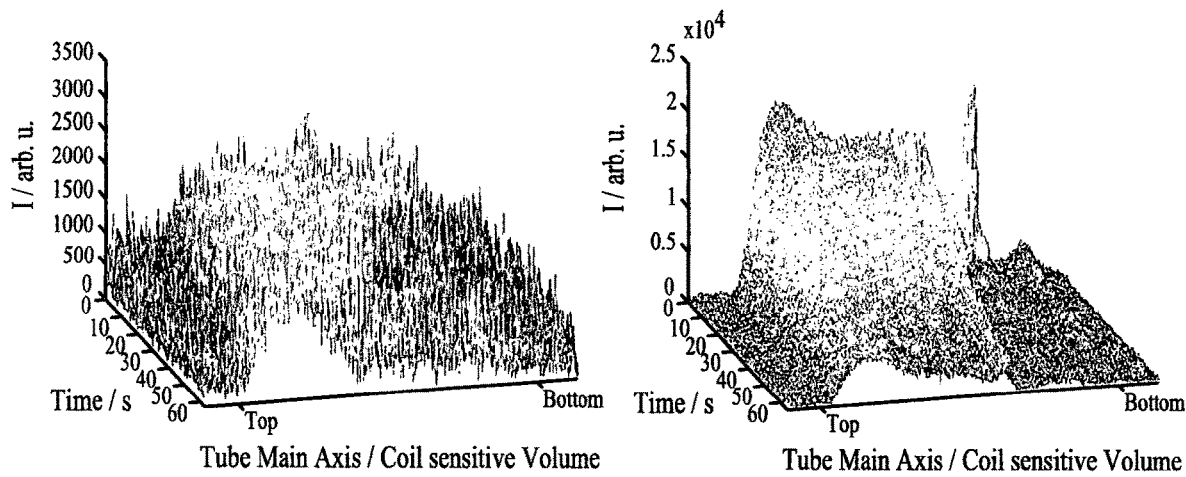
Figure S60
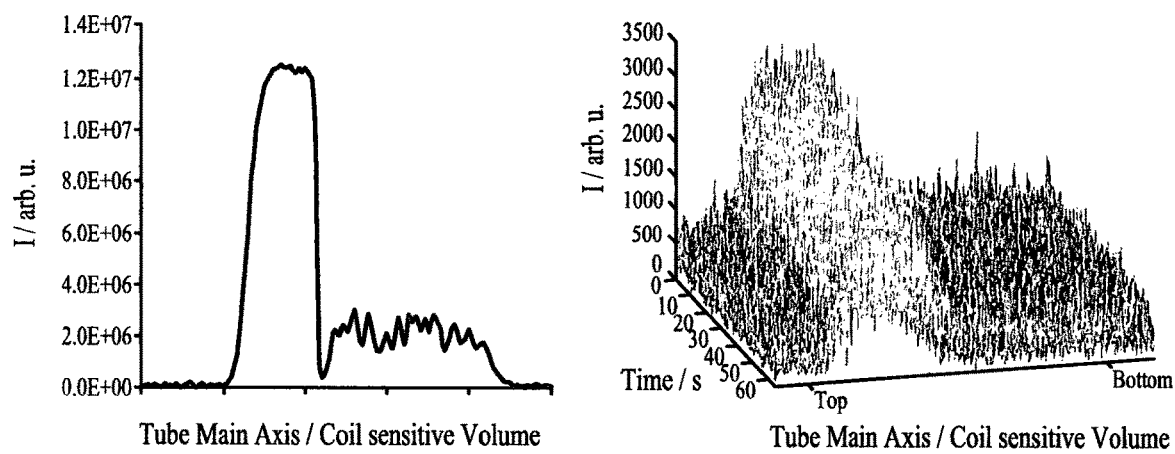
Figure S61

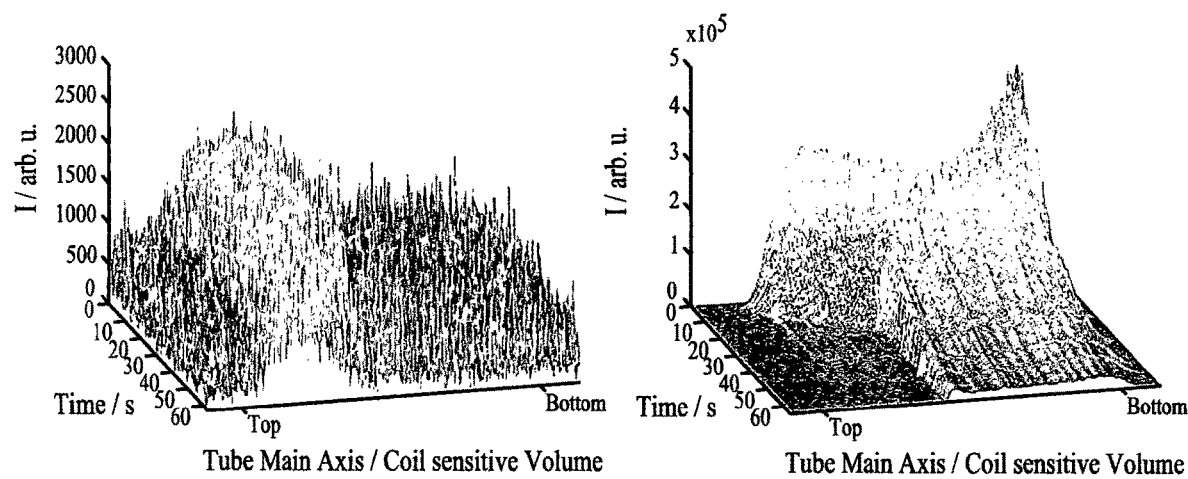
Figure S62
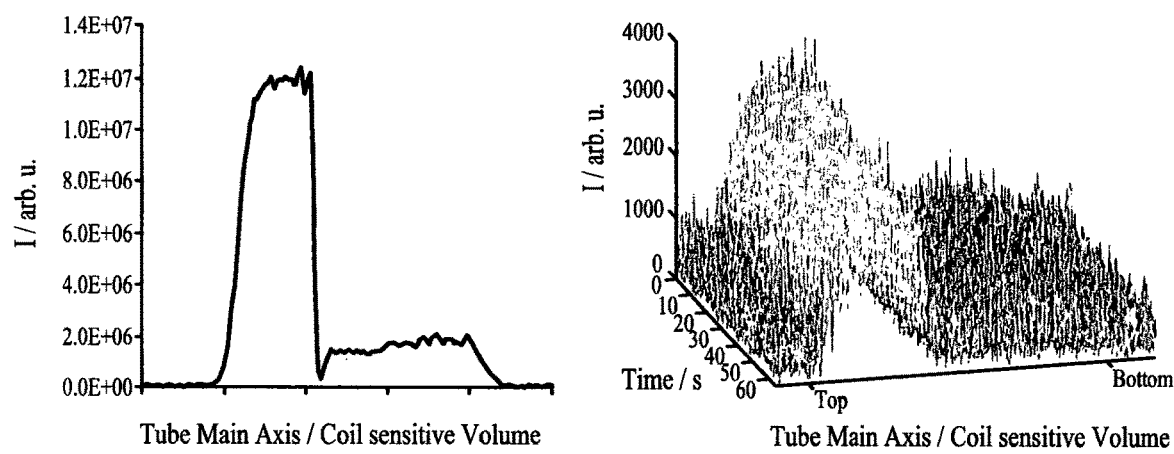
Figure S63

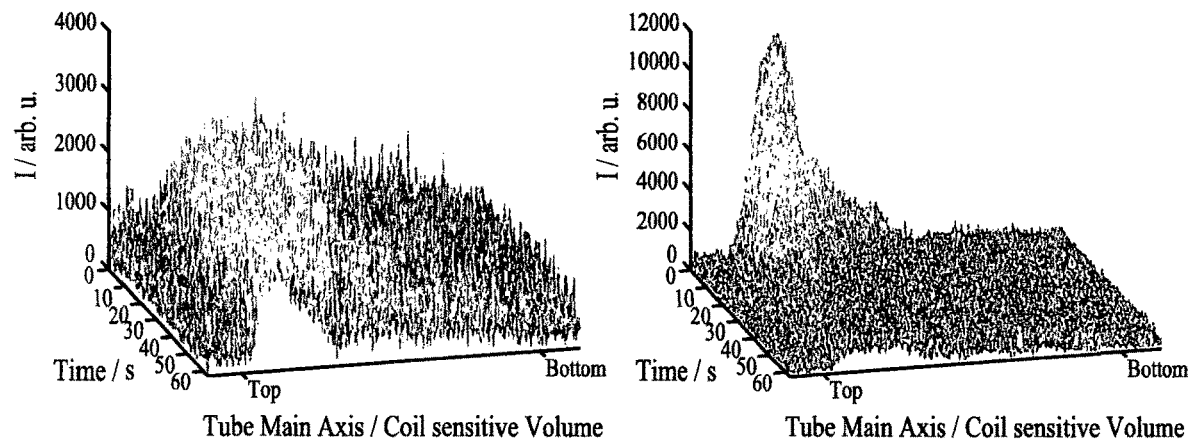
Figure S64
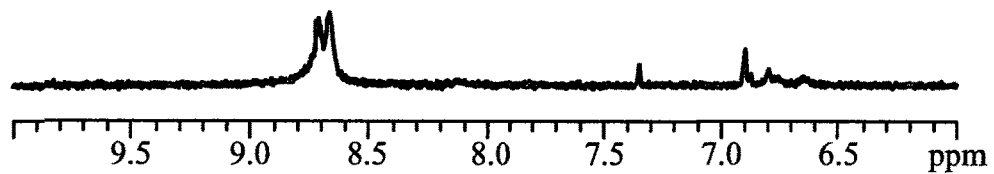
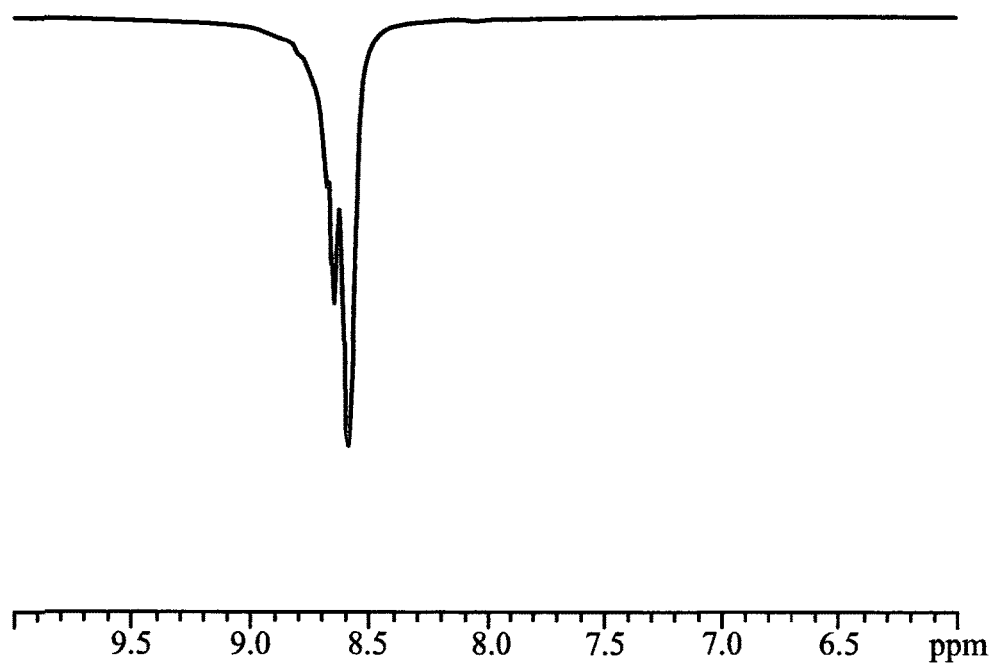
Figure S65

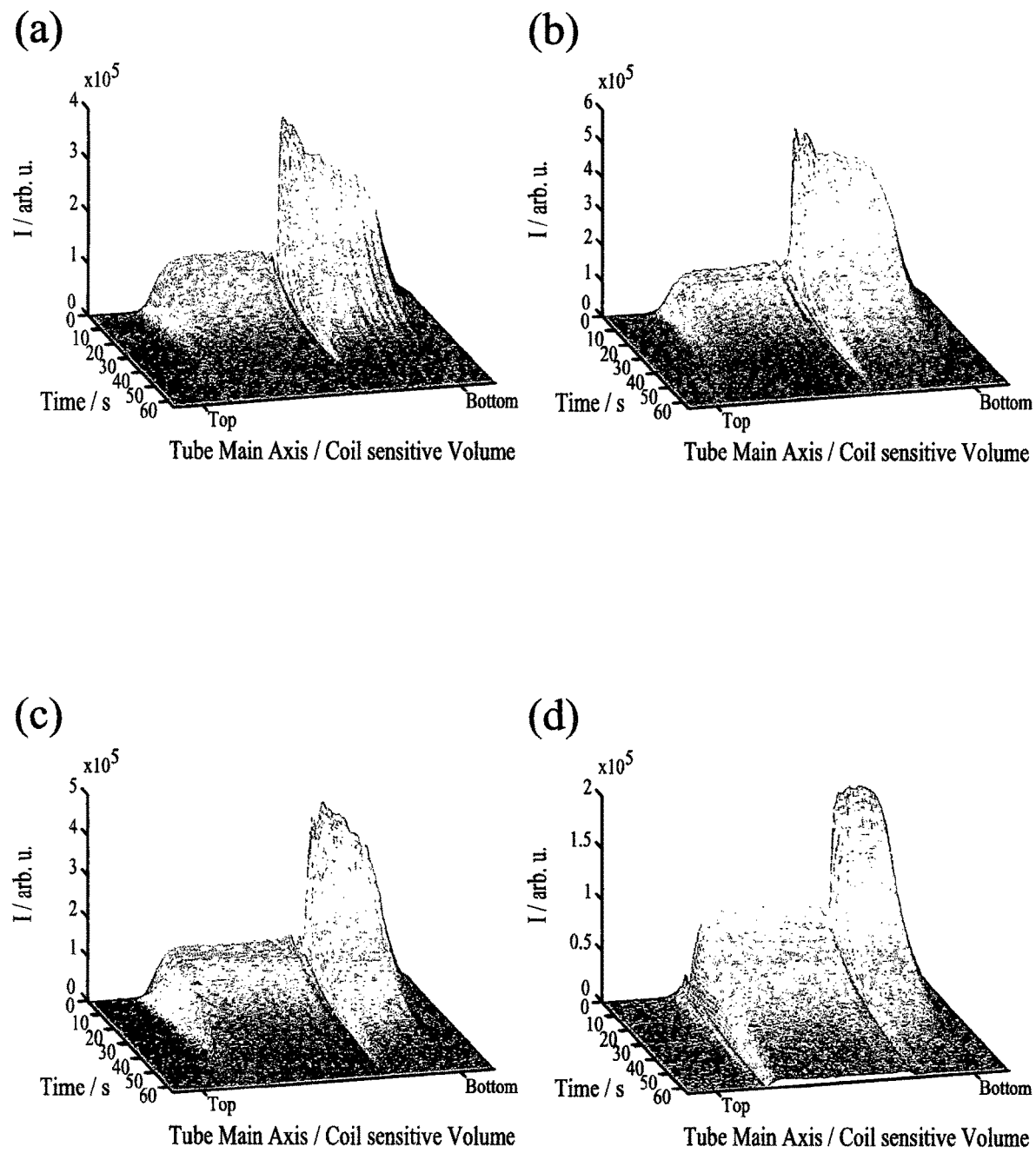
Figure S66

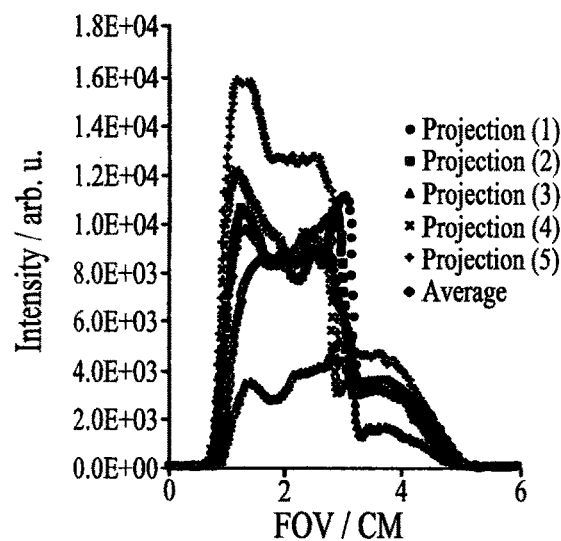
Figure S67
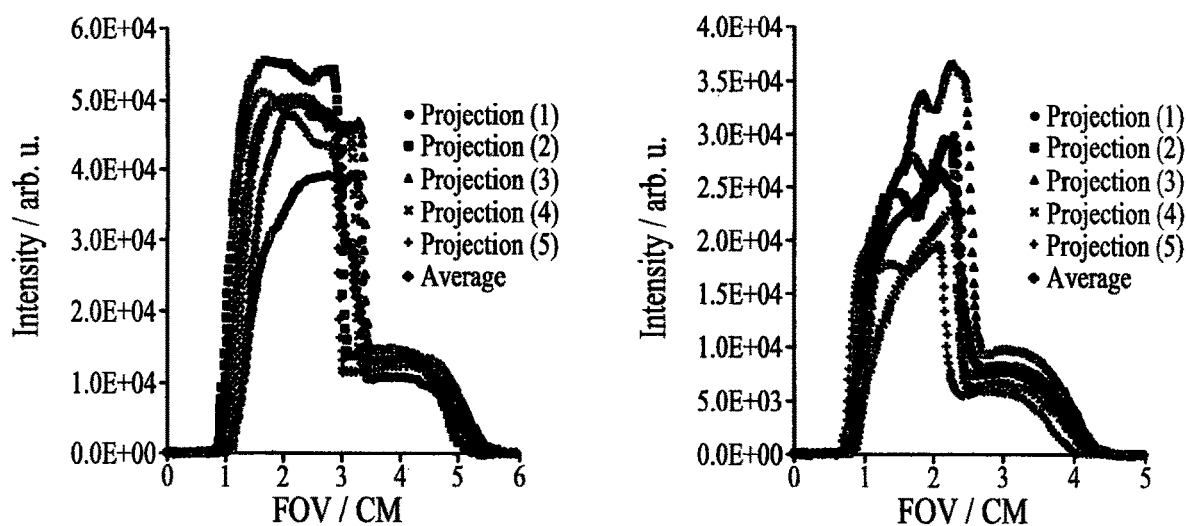
Figure S68

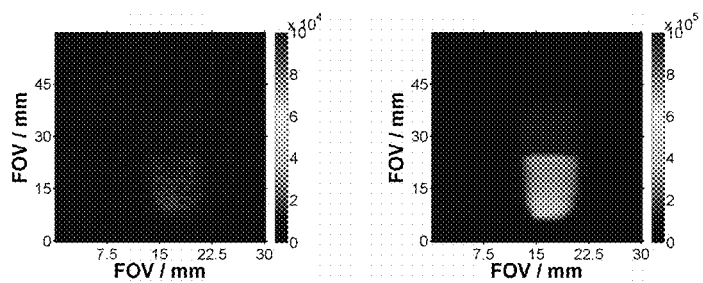
Figure S69
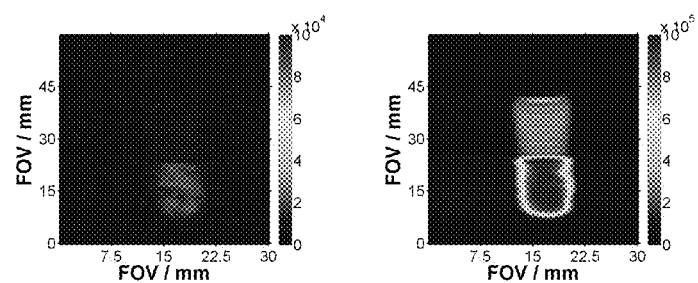
Figure S70
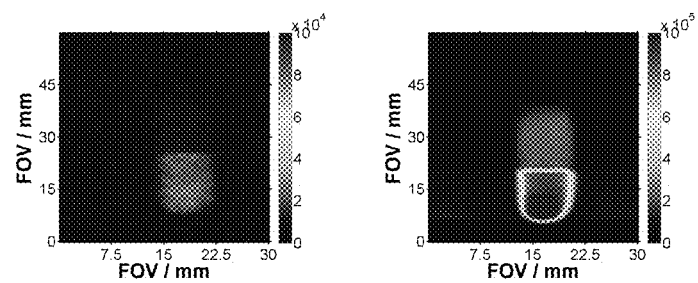
Figure S71

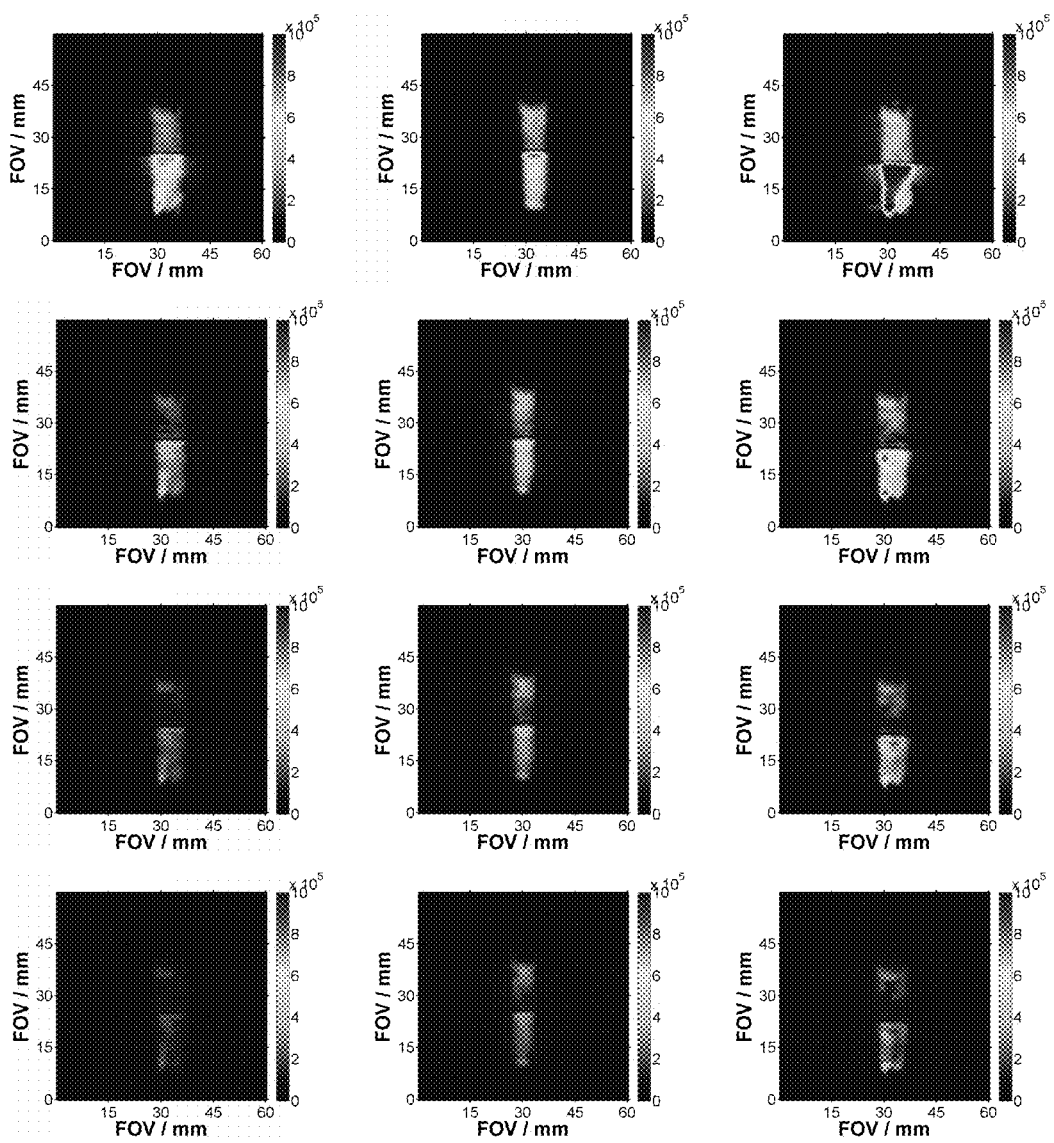
Figure S72

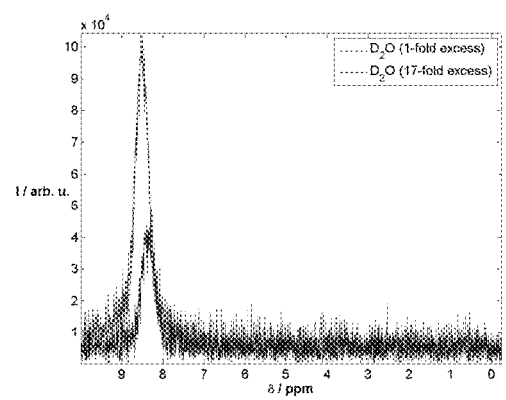
Figure S73
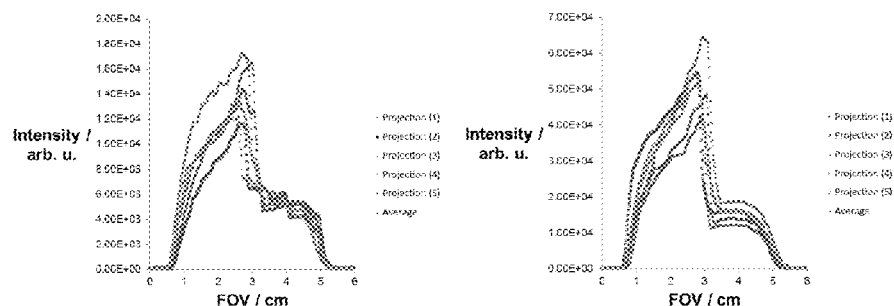
Figure S74

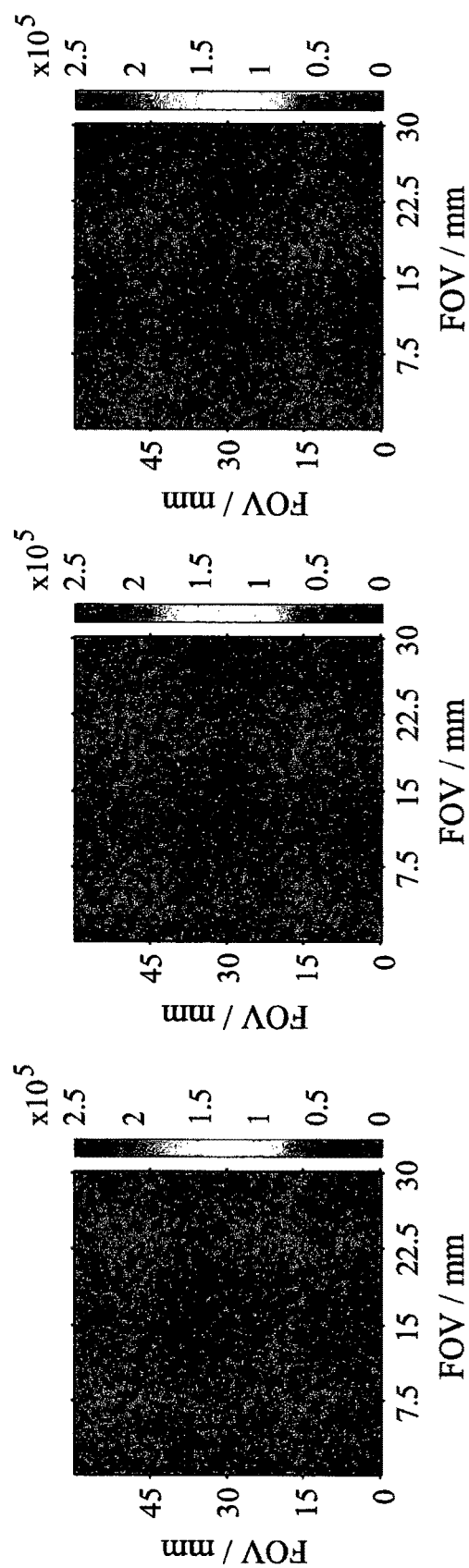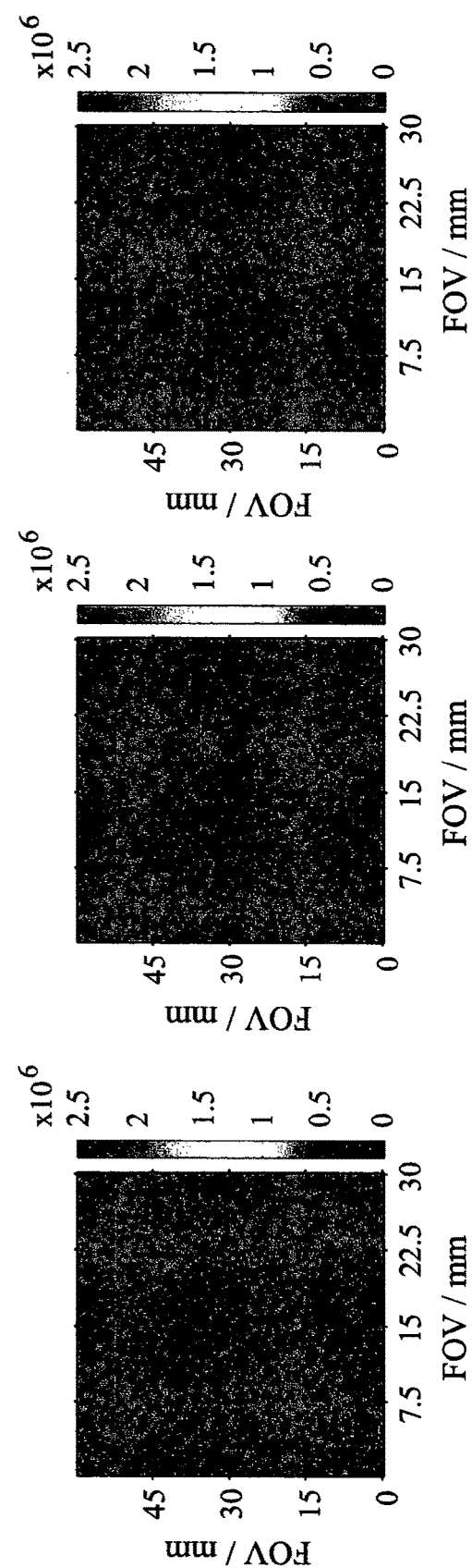
Figure S75

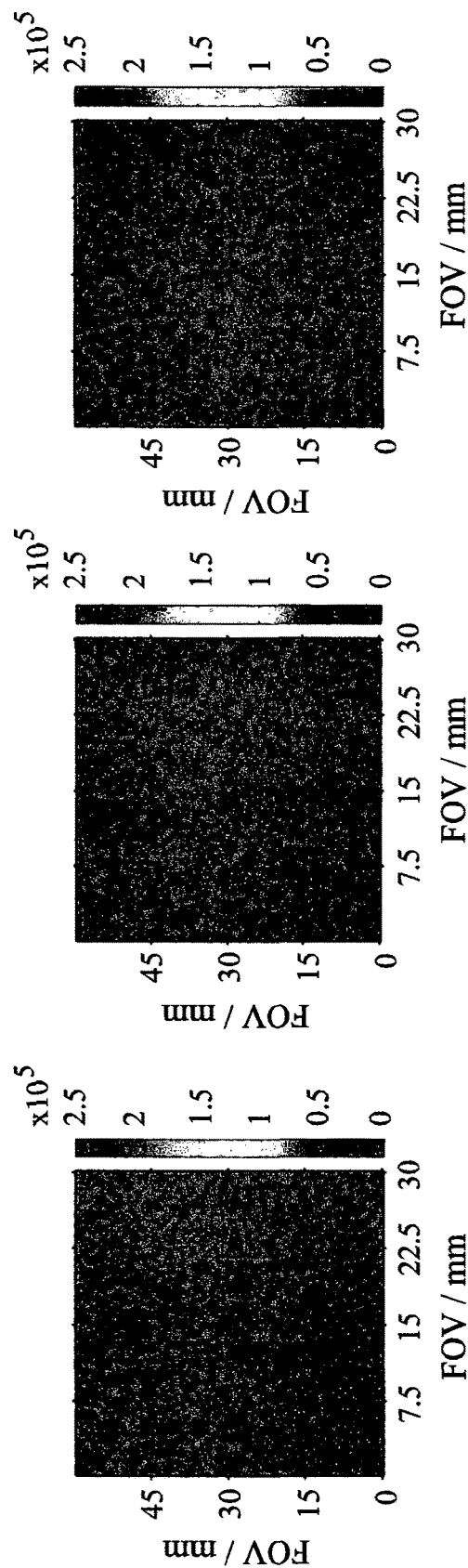
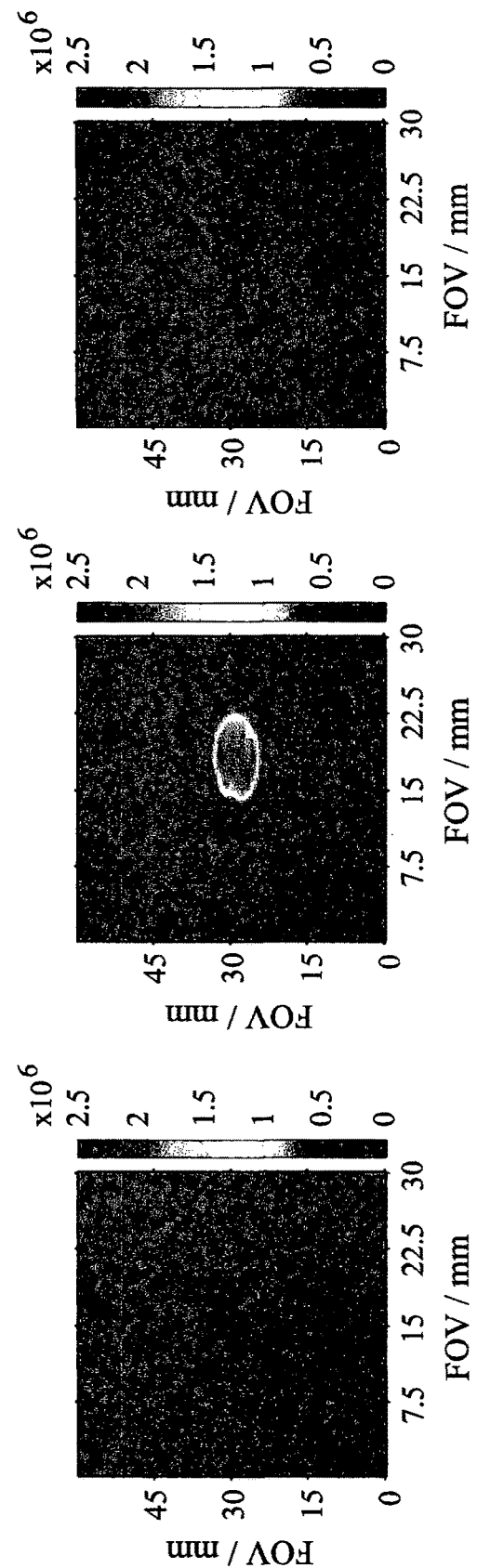
Figure S76 a)
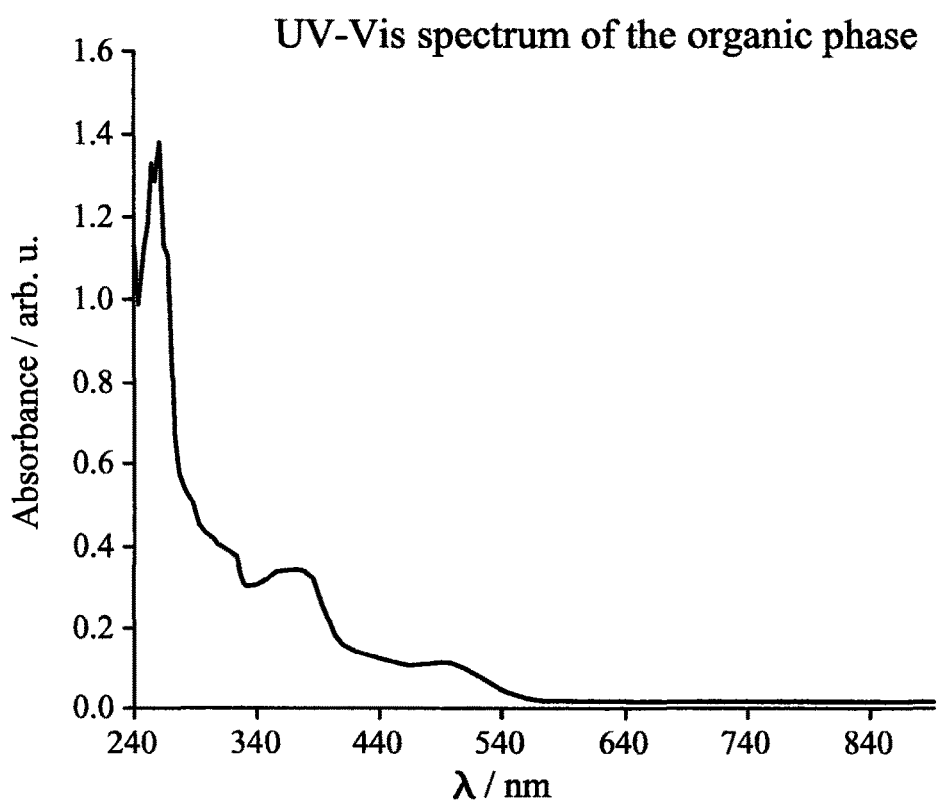
b)
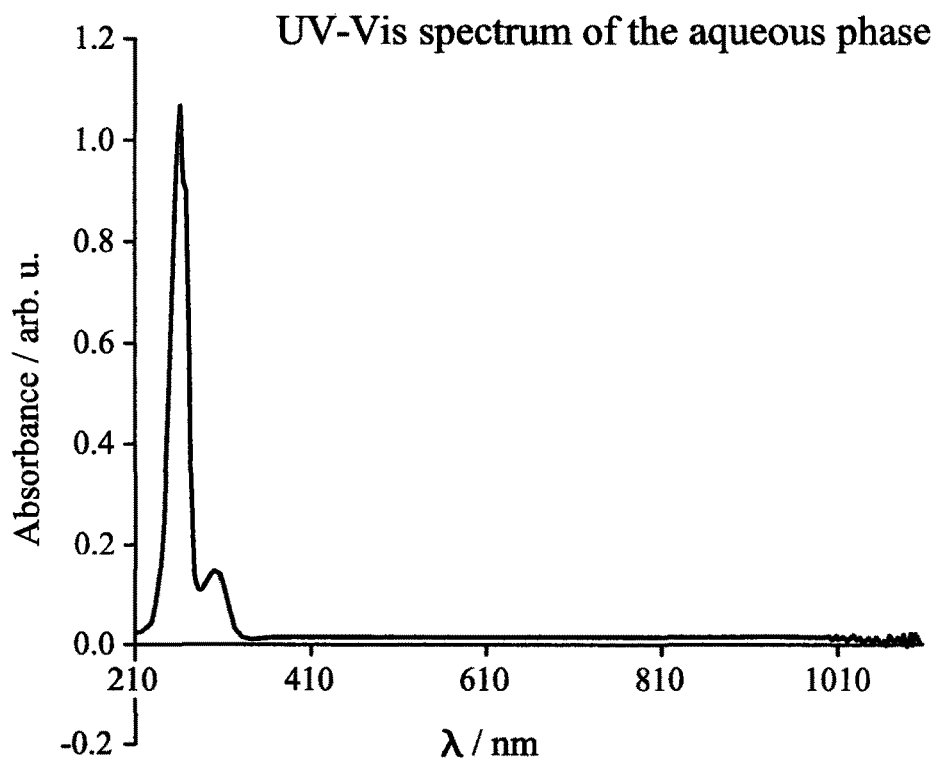
Figure S77

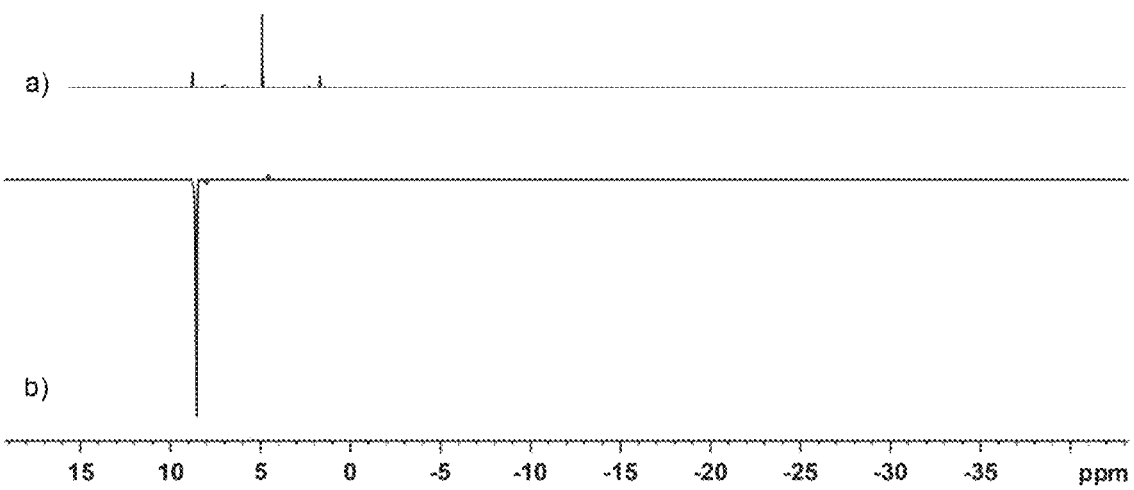
Figure S78
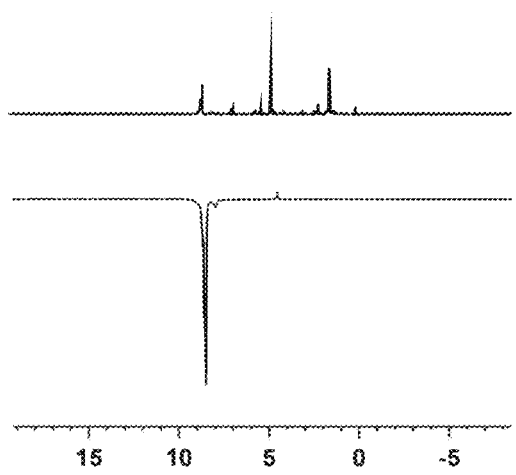
Figure S79

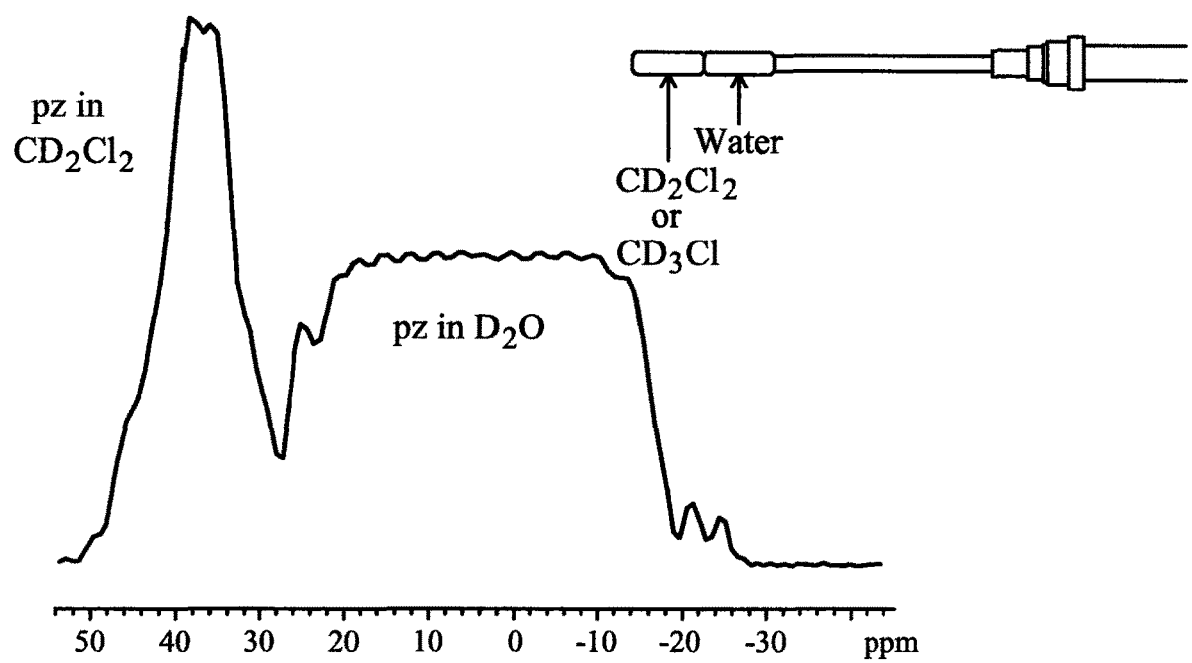
Figure S80
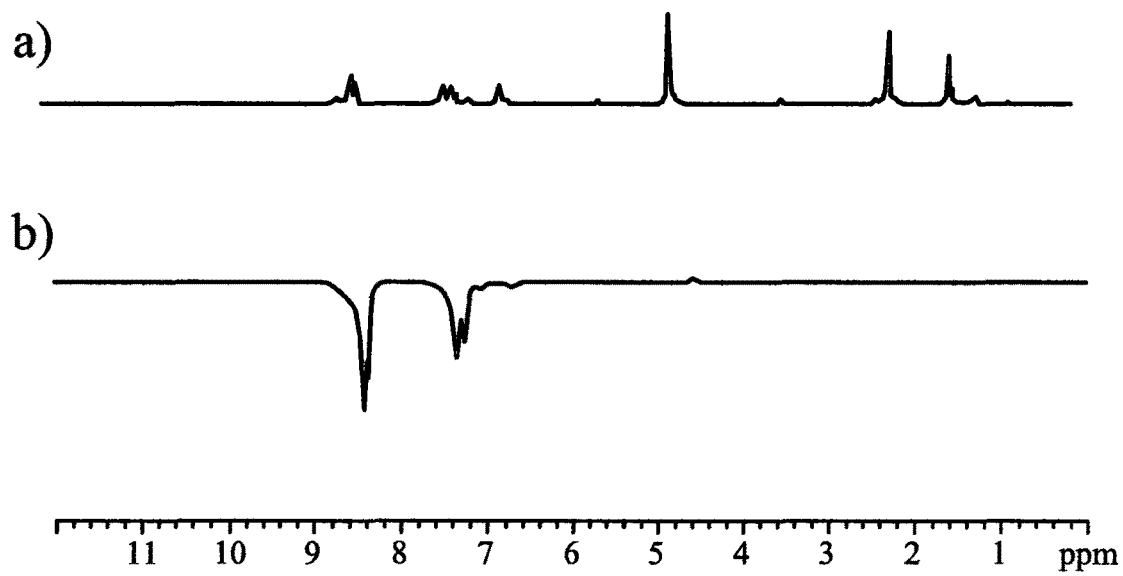
Figure S81

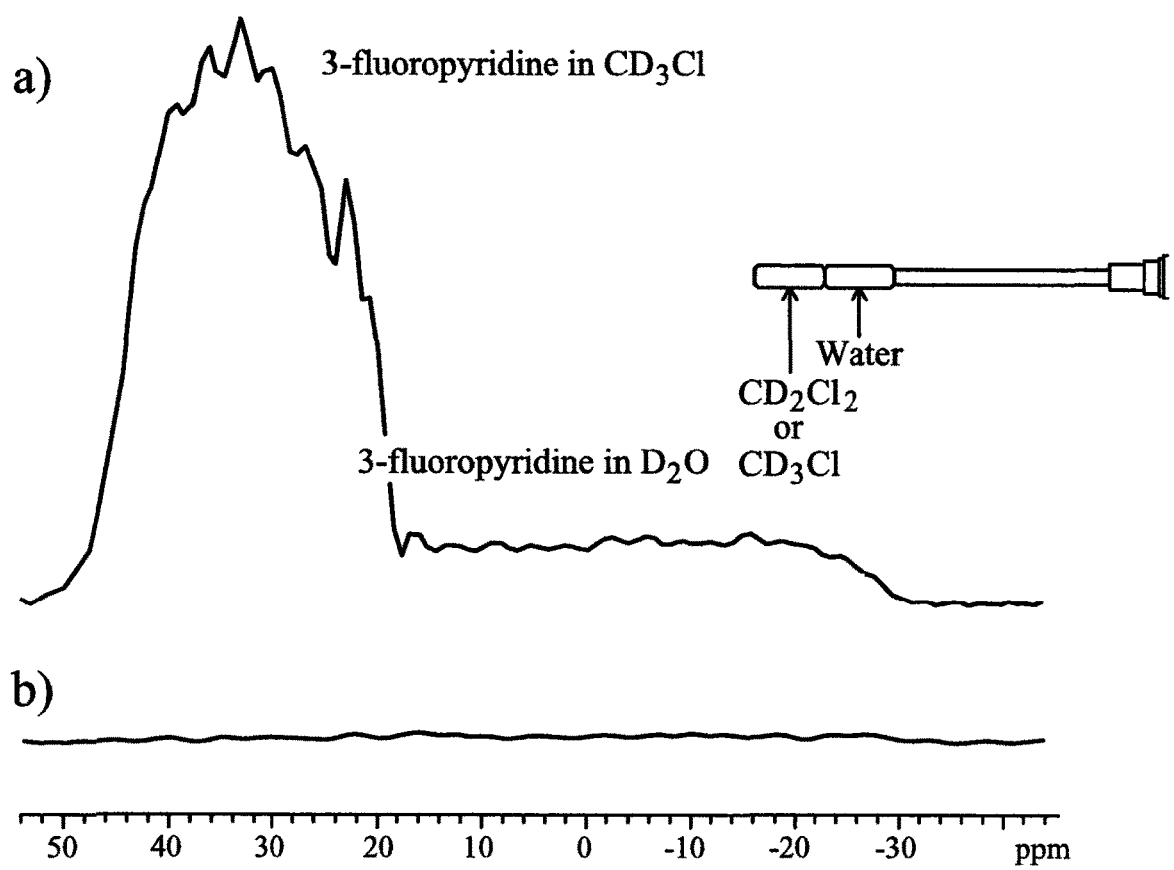
Figure S82
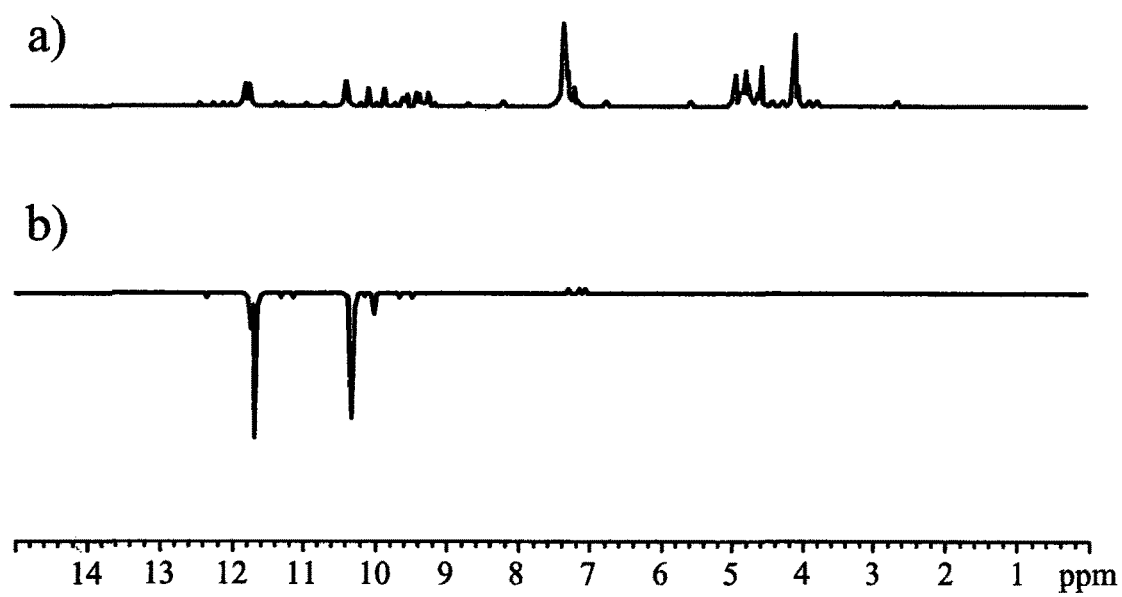
Figure S83

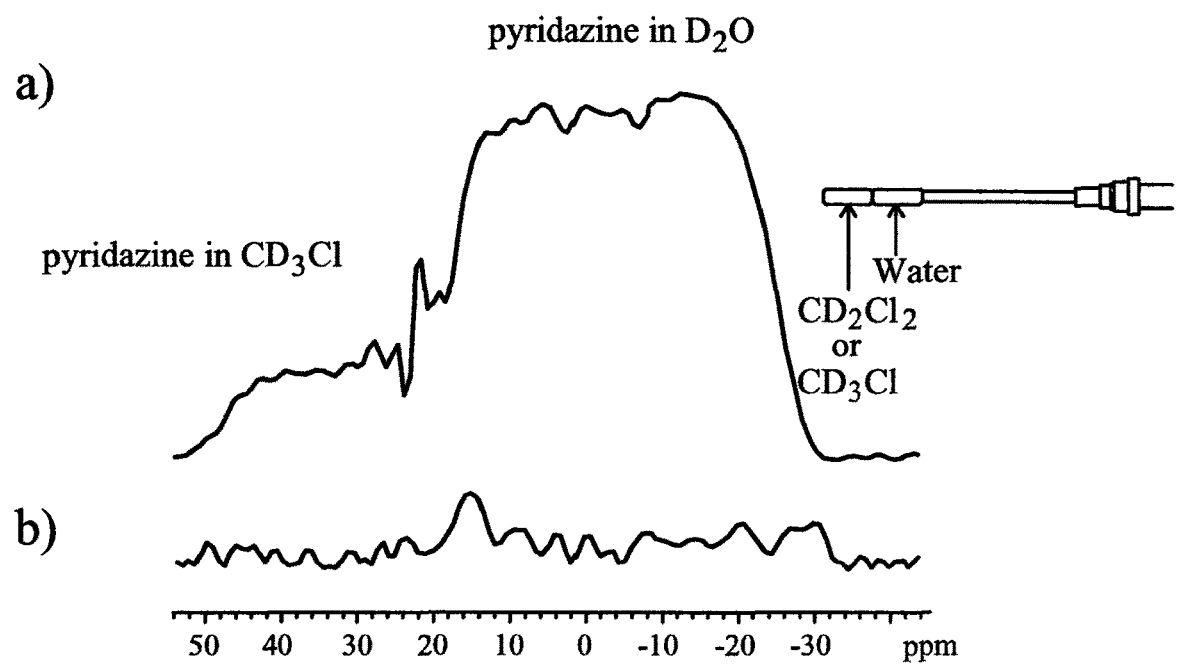
Figure S84
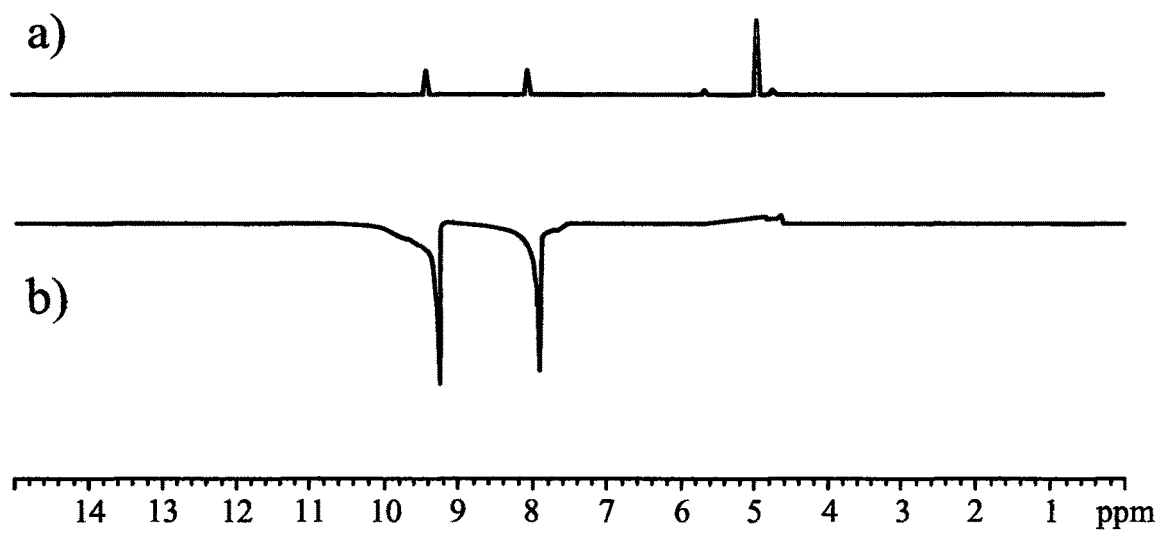
Figure S85

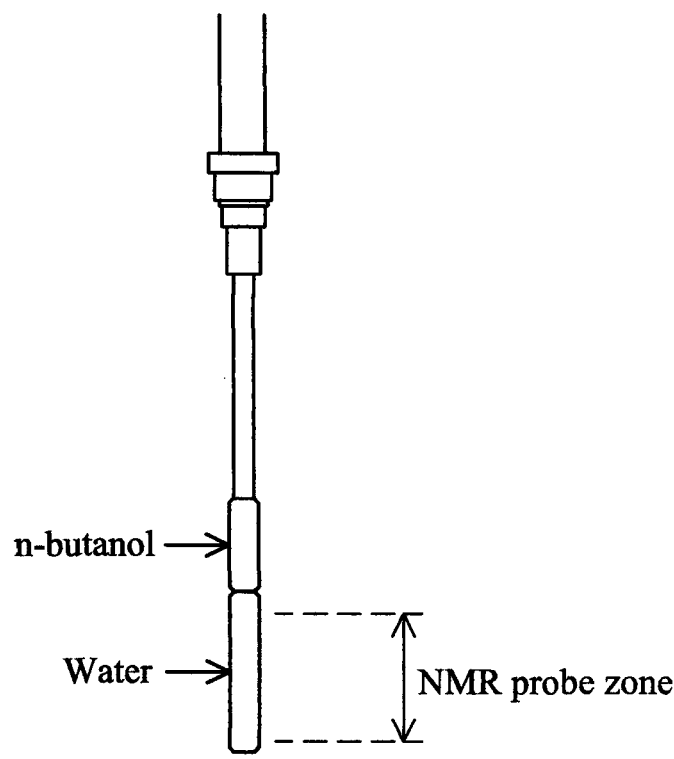
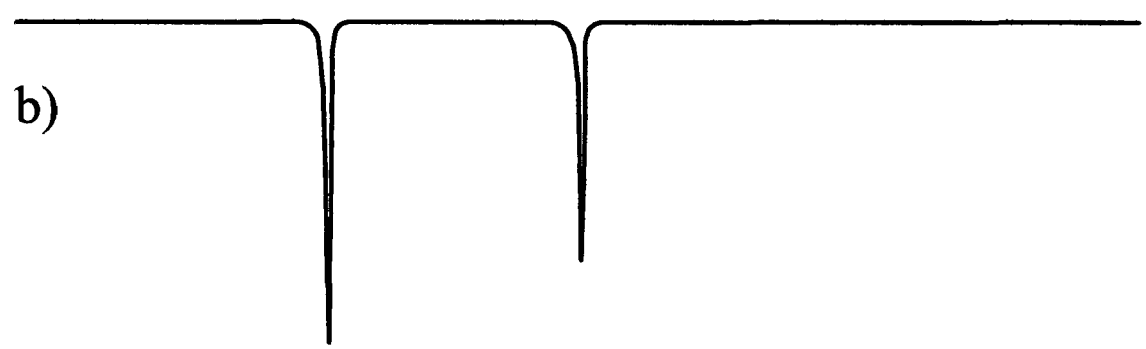
Figure S86

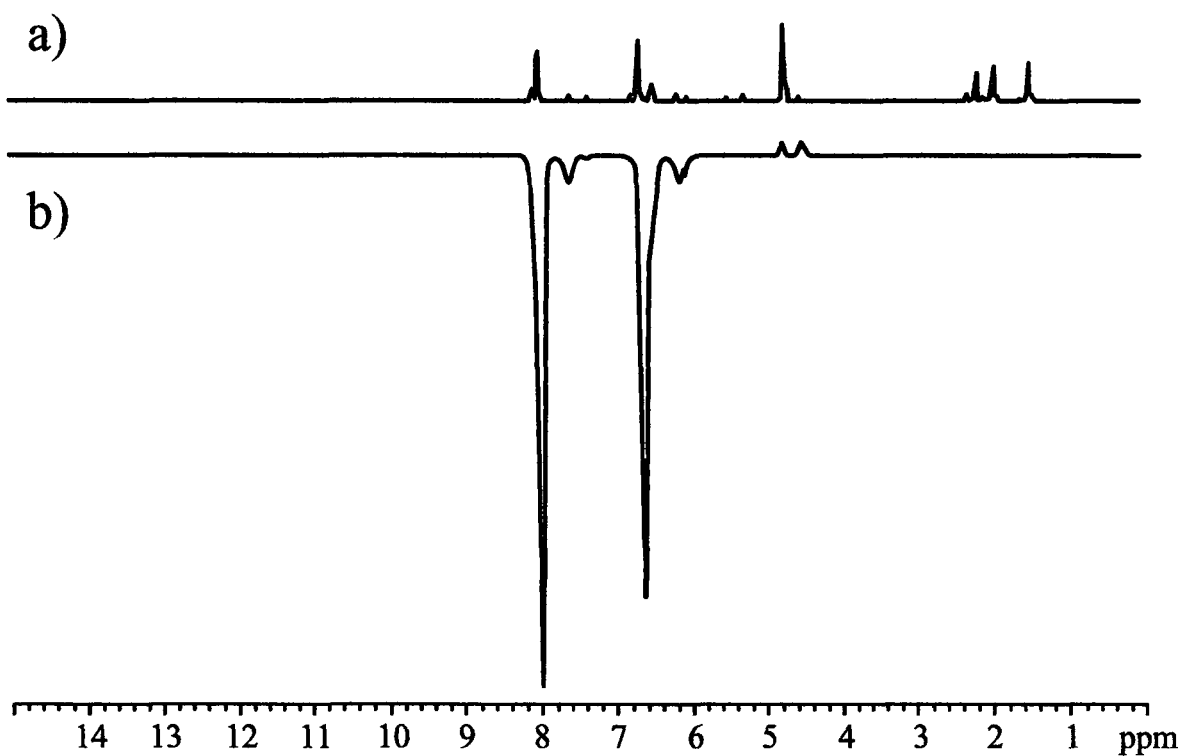
Figure S87
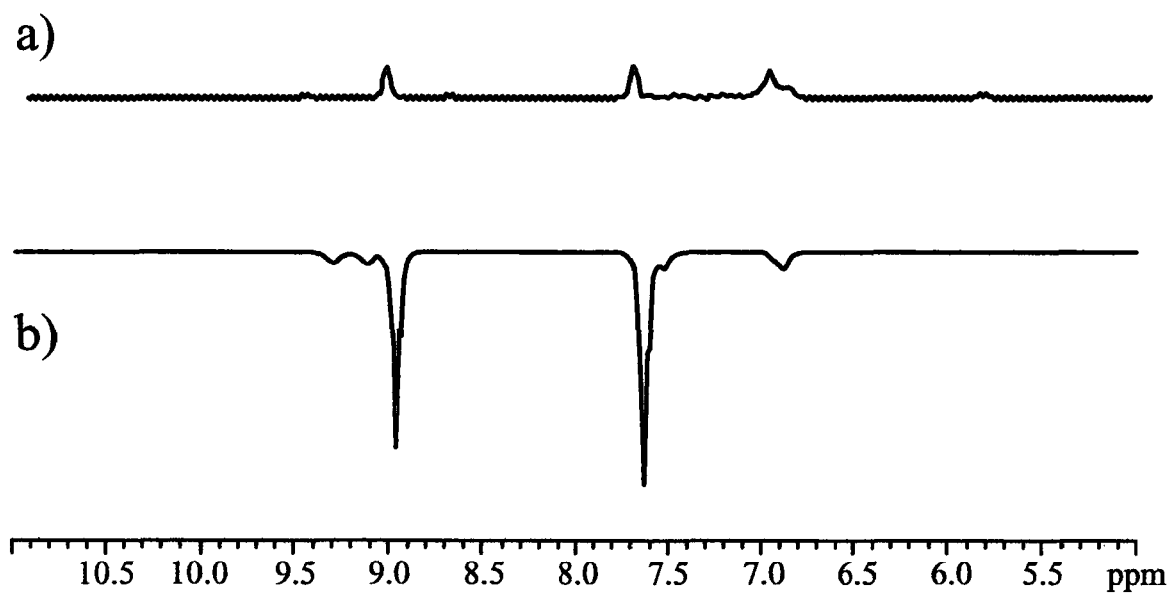
Figure S88

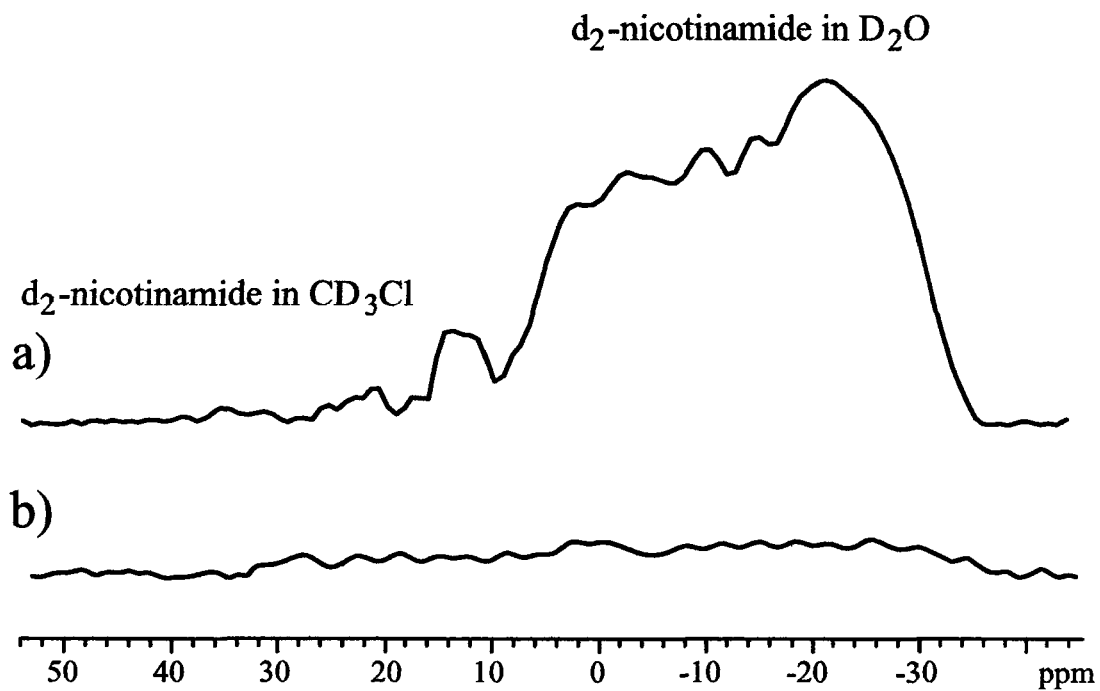
Figure S90
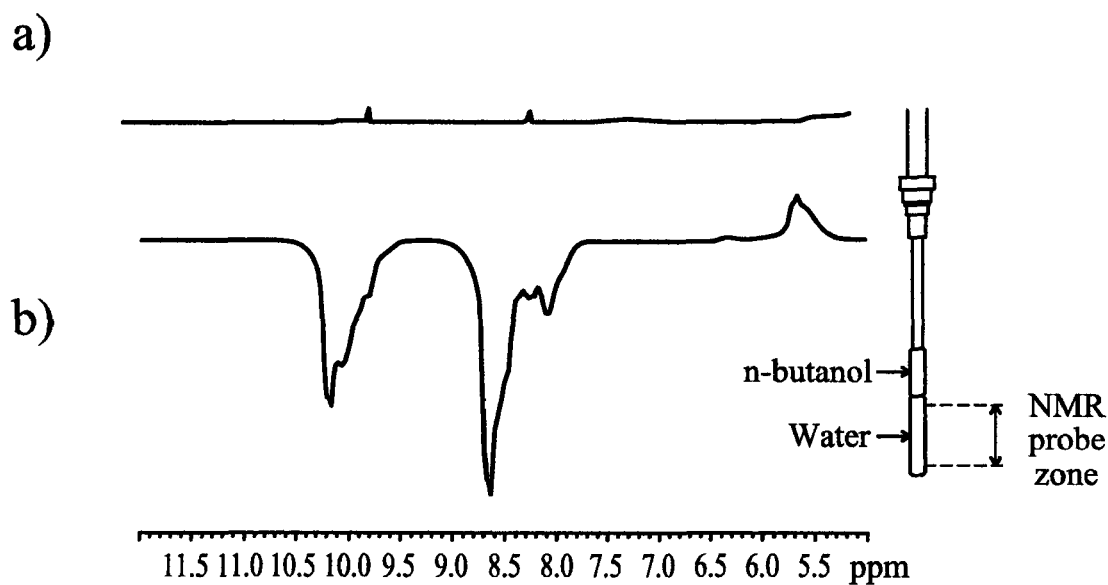
Figure S91 a)
b)
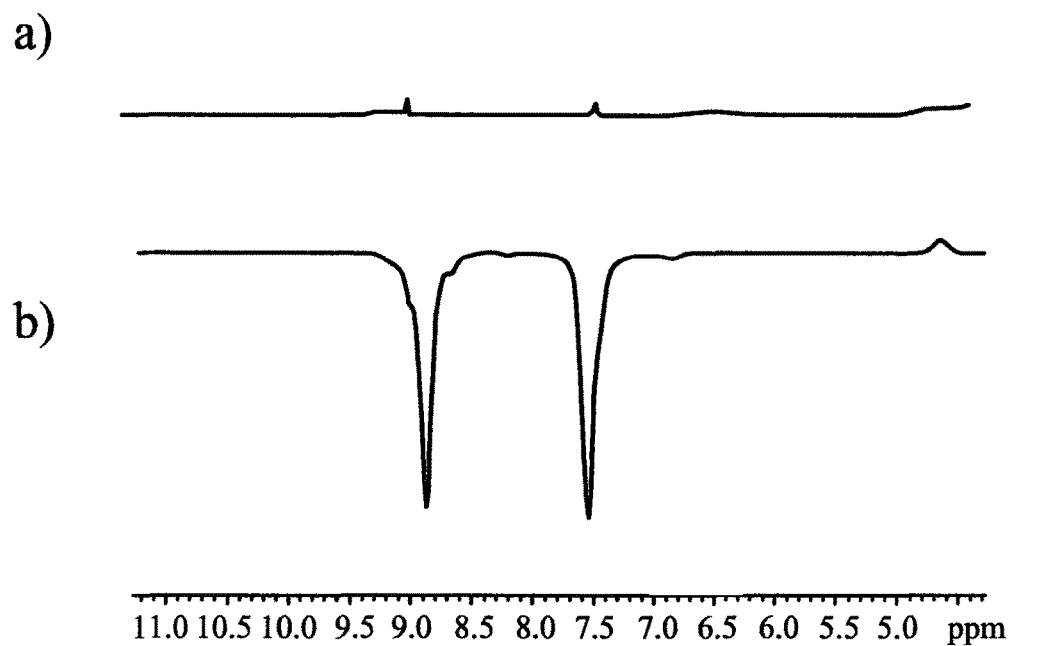
Figure S92
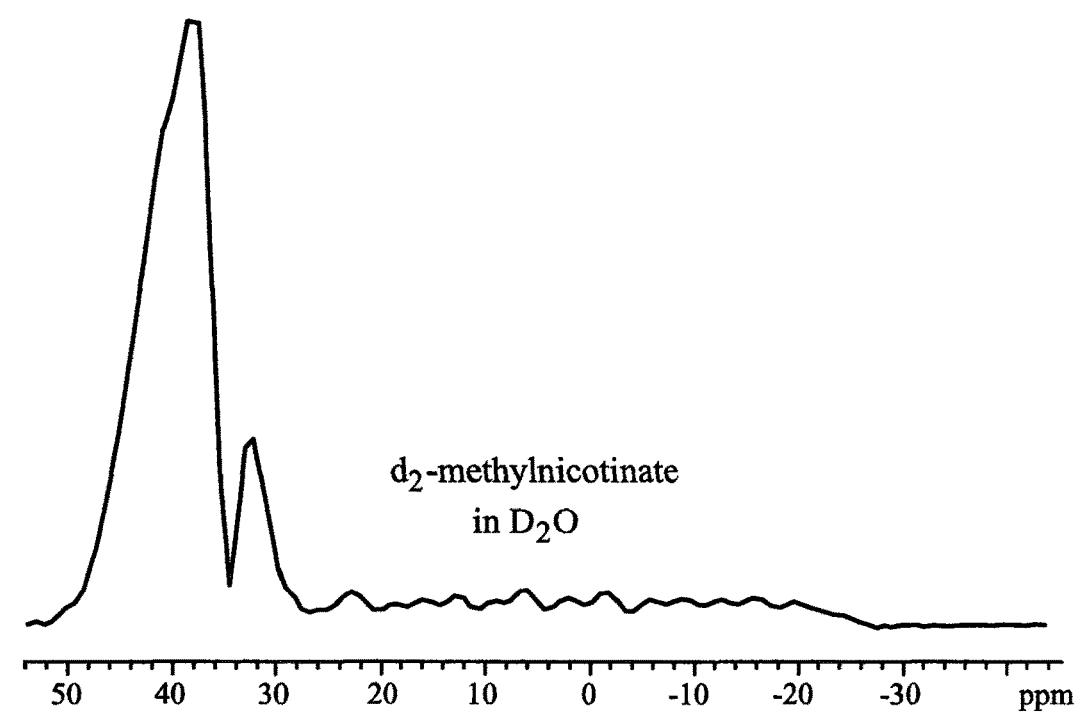
Figure S93

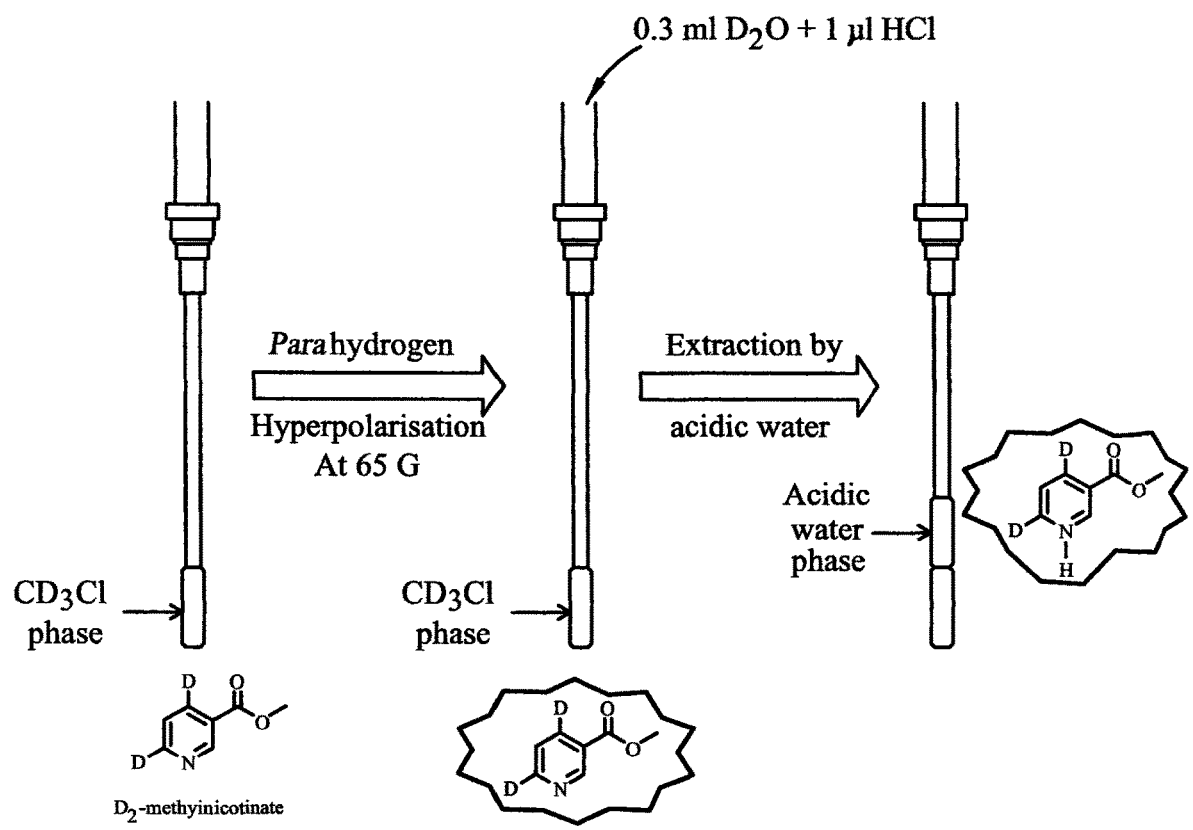
Figure S94
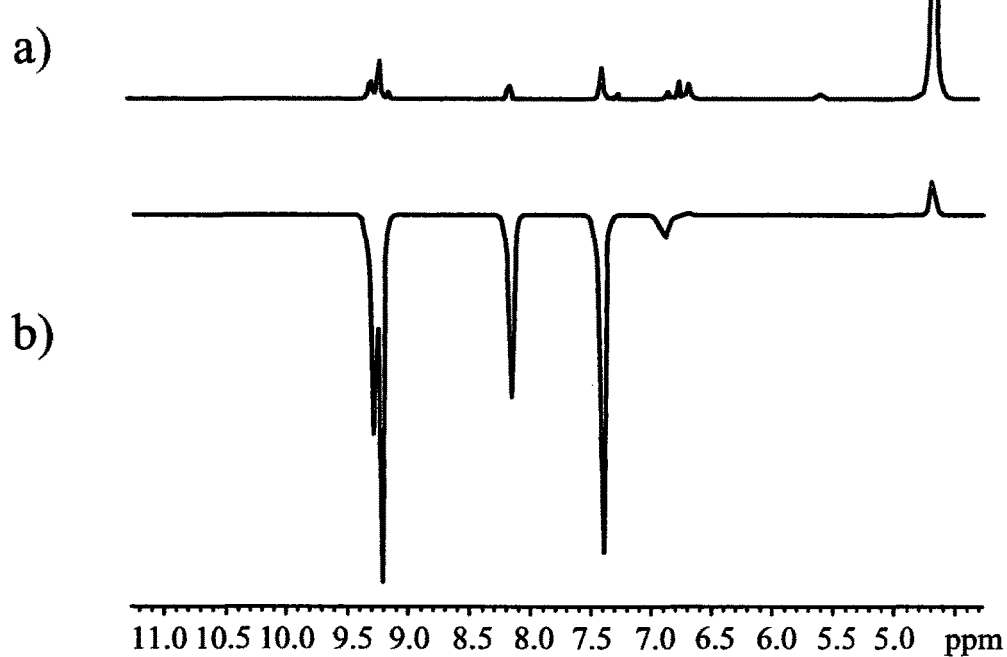
Figure S95

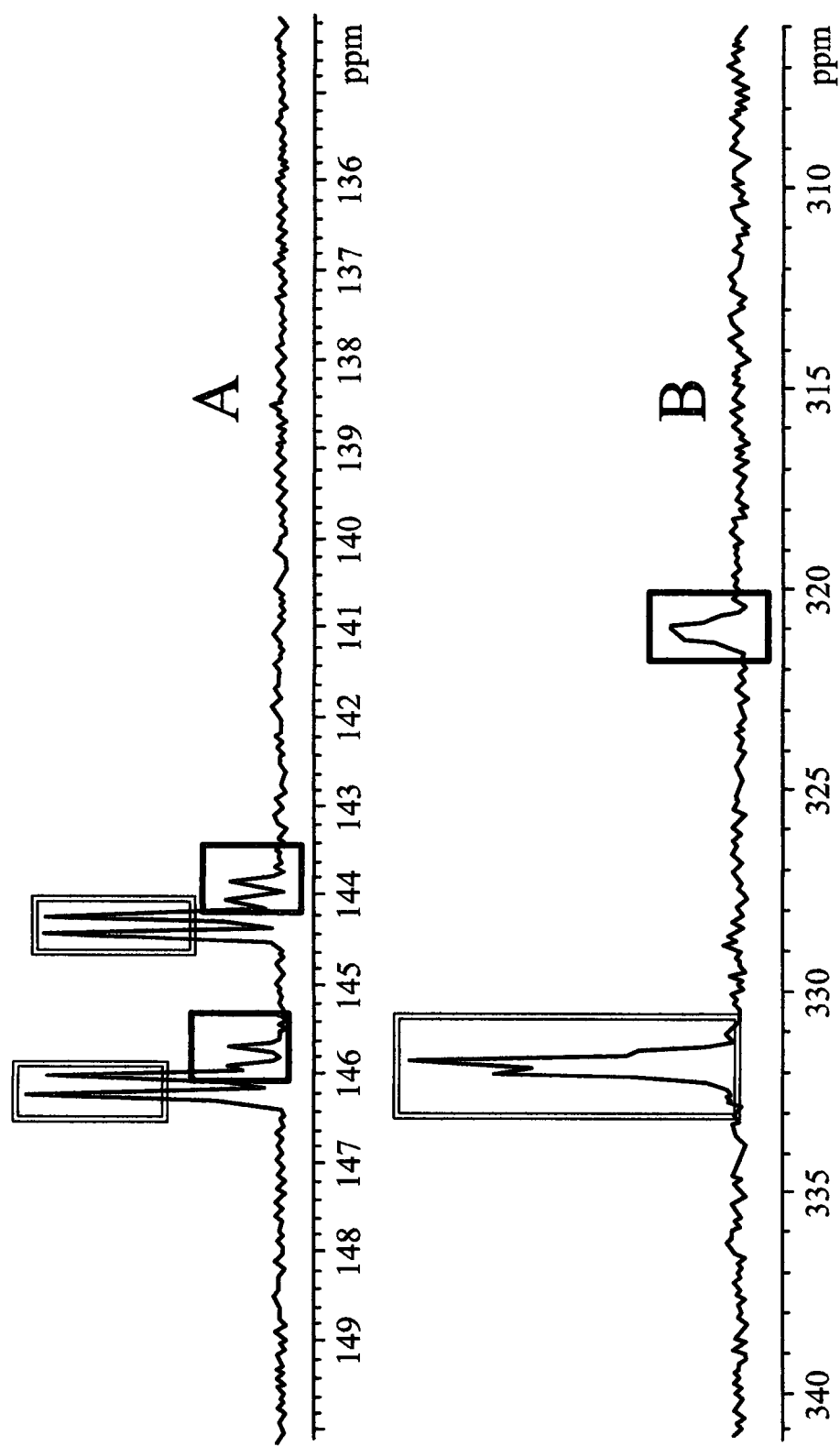
Figure S96

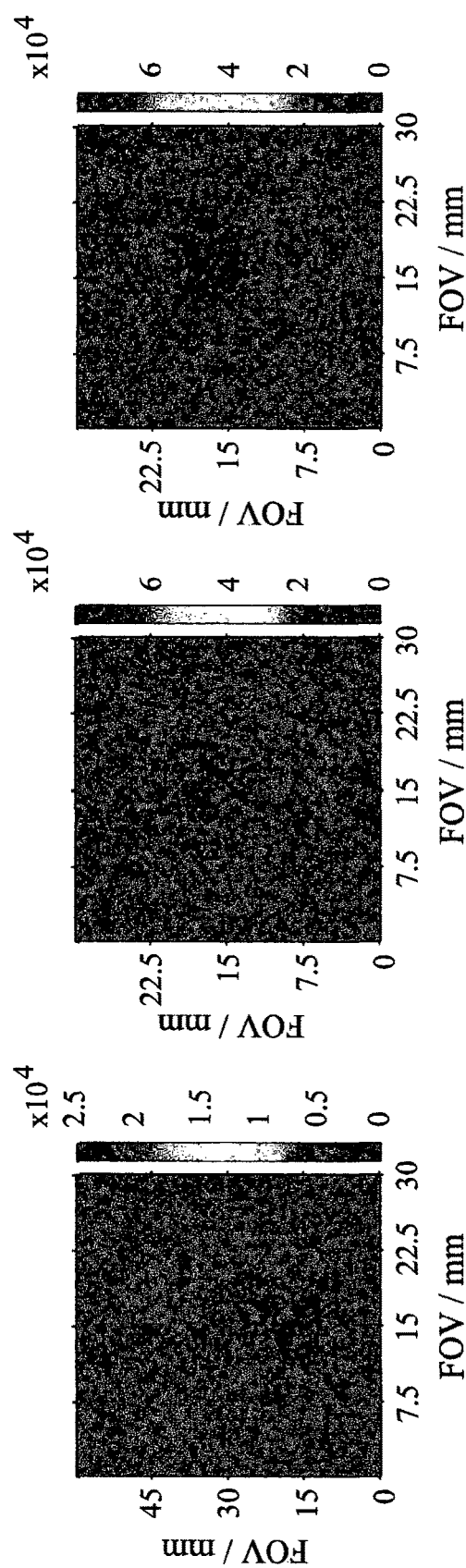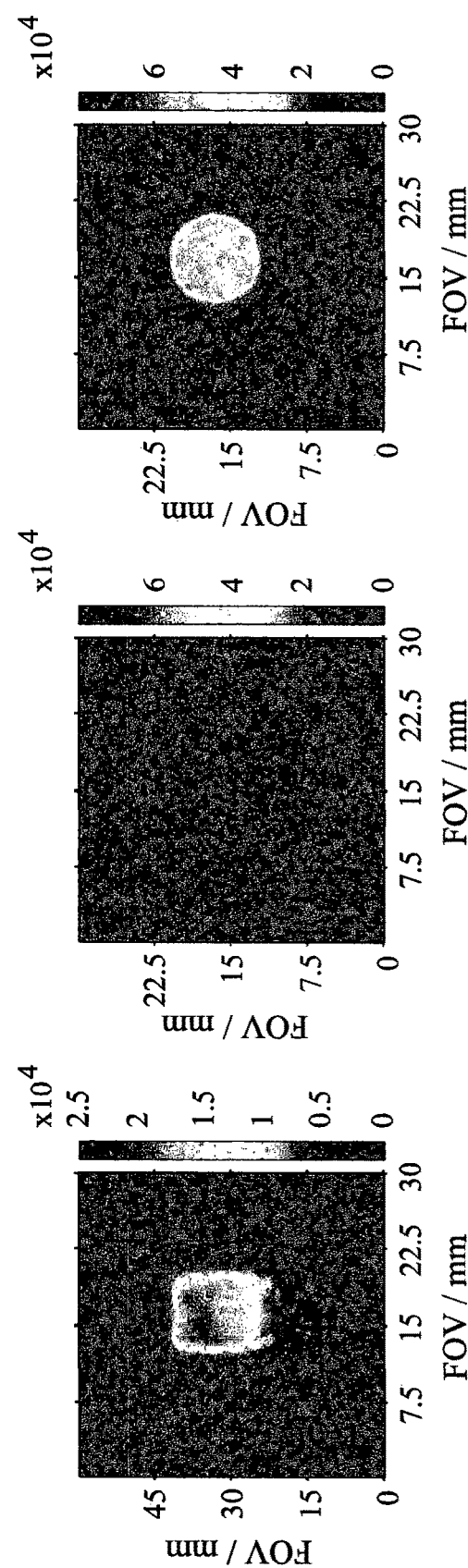
Figure S97

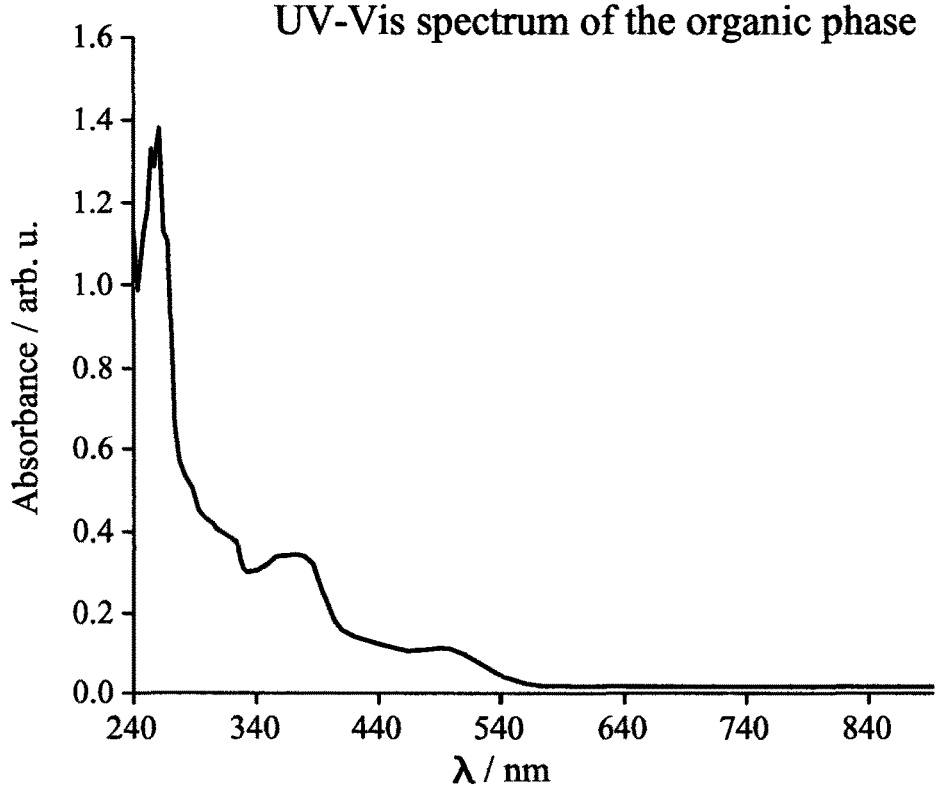
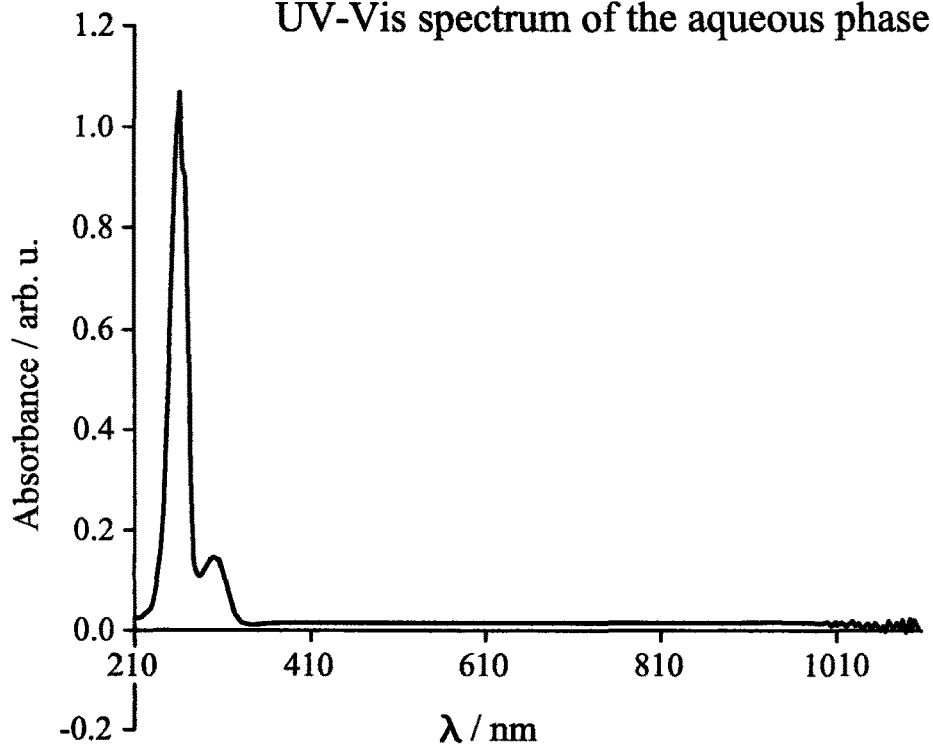
Figure S98

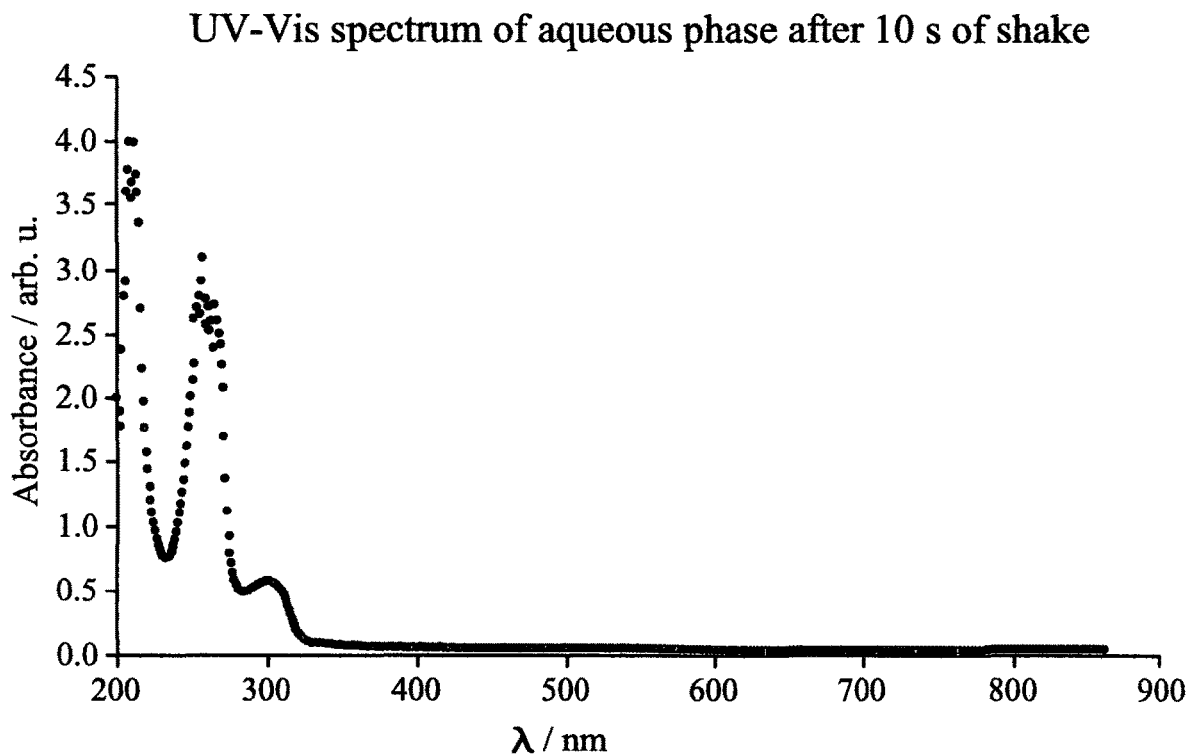
Figure S99
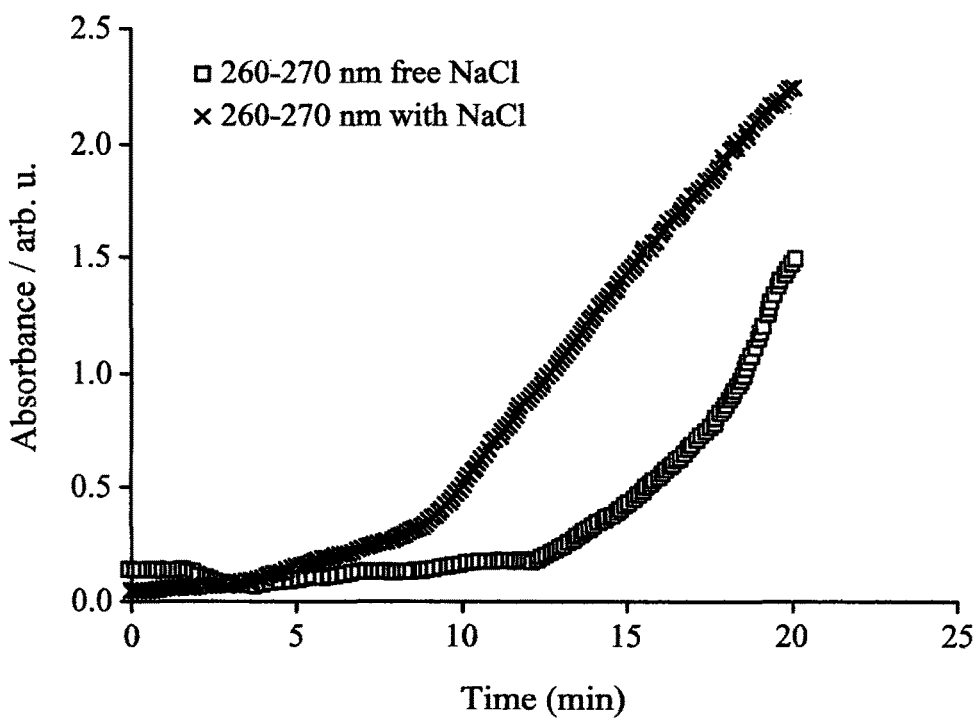
Figure S100

HYPERPOLARISATION IN AQUEOUS MEDIA VIA SABRE

CROSS REFERENCE TO RELATED APPLICATIONS

This is the national phase under 35 U.S.C. § 371 of International Application No. PCT/GB2018/050573, filed on Mar. 7, 2018, which claims priority to and the benefit of United Kingdom Patent Application No. 1703658.3 filed on Mar. 7, 2017, the entire disclosures of each of which are incorporated by reference herein.

FIELD OF THE INVENTION

The present invention relates to a method for the production of an aqueous imaging medium of a hyperpolarised agent through Signal Amplification By Reverse Exchange (SABRE).

More particularly, the present invention provides an aqueous imaging medium, a method of preparation of said imaging medium and a method for carrying out an MR experiment, e.g. NMR or MRI, with enhanced sensitivity on a water soluble compound comprising hyperpolarisable nuclei.

BACKGROUND OF THE INVENTION

NMR is commonly used across a large number of disciplines, including chemistry, biochemistry and medicine, and is inherently insensitive as it probes a population difference between states that are close in energy. This population difference can be increased by employing a hyperpolarisation technique, such as optical pumping, dynamic nuclear polarisation (DNP)[1] or the use of parahydrogen (p-$H_2$)[2], via parahydrogen induced polarization (PHIP)[3], to increase sensitivity.

Magnetic resonance imaging (MRI) is a technique based upon the science of nuclear magnetic resonance (NMR). MRI has become particularly attractive to physicians as images of parts of a patient's body thereof can be obtained non-invasively and without exposing the patient and the medical personnel to potentially harmful radiation such as X-rays.

Furthermore, due to its high quality images and good spatial and temporal resolution, MRI is a favourable imaging technique for imaging patients' soft tissue and organs.

Signal amplification by reversible exchange (SABRE) is a technique which increases the response (or visibility) of compounds in NMR and MRI measurements. This increased visibility allows higher contrast and resolution MRI imaging, shorter scan times and lower detection thresholds in NMR spectroscopy. Unlike other polarisation methods, such as DNP, the SABRE process can be performed in seconds, and the agents are then measured using NMR or MRI.

One of the main advantages of SABRE is that it achieves this result without the incorporation of p-$H_2$ into the substrate. This technique is effectively a form of catalysis which utilizes a suitable catalyst[5], to reversibly bind both $H_2$ (p-$H_2$) and the substrate in order to assemble a reaction intermediate in which polarization is able to transfer, at low magnetic fields, from p-$H_2$ into the substrate.[6]

NMR and MRI involve the detection of what can be viewed to be transitions of nuclear spins between an excited state and a ground state in an applied magnetic field. Because the energy difference between these states is relatively small, the usual Boltzmann distribution of chemically identical nuclei is such that at room temperature the populations of nuclear spin states which are in dynamic equilibrium are almost identical. Since the strength of the detected signal in magnetic resonance experiments is proportional to the population difference, NMR and MRI signals are typically weak.

The strength of detectable NMR signals can however be enhanced by hyperpolarising the magnetic nuclei. Hyperpolarisation in this context refers to a process in which a significant excess of magnetic nuclei are induced into a spin state. This results in a large increase in available signal due to the much larger inequality of populations across the energy levels that will ultimately be probed. In order for a hyperpolarised state to be useful, it is important that the spin state is sufficiently long lived to provide useful information, i.e. that the relaxation time of the spin state is 'long'. The rules governing the relaxation rates of nuclear spins are complex but known. It suffices to say that certain nuclei and spins systems have relaxation times which may extend from seconds to hours, days, months or even years.

There are a number of ways to induce certain nuclei into a hyperpolarised state. The simplest way is to cool the material to very low temperatures in the presence of a magnetic field, which will favour population of the lower energy state in which the spins of the nuclei are aligned with the applied magnetic field. This method is suitable for the production of hyperpolarised monatomic gases such as xenon or helium-3. The polarization levels of these nuclei have also been increased via the use of laser-based technologies.

One important objective of hyperpolarisation lies in the area of magnetic resonance imaging (MRI) where applications in medical diagnosis are expected.[7] In fact, biomedical applications such as tumour or metabolic-flux imaging, in vivo, are beginning to become a reality for the resulting hyperpolarised agents.[8] Consequently, the toxicity of the SABRE catalyst, solvent and substrate combination need to be minimized if this method is ever to find clinical use.

Nuclei can be hyperpolarised by a process known as parahydrogen induced polarization (PHIP). PHIP has proved to be highly efficient and has currently achieved greater enhancement of heteronuclear NMR signals than other methods known in the art. PHIP is generally the result of a chemical reaction in which the parahydrogen nuclei are transferred irreversibly into another molecule having certain symmetry properties. Under the right circumstances, the spin state of the parahydrogen molecule is preserved in the spins of the two hydrogen atoms which become part of the new molecule. If other NMR-active nuclei are within coupling distance of the hydrogen nuclei, spin polarization of those nuclei can be transferred spontaneously in an optimal magnetic field. In this way, the signals of heteronuclei such as $^{13}C$, $^{15}N$ and $^{31}P$ can be enhanced. By way of example, WO 99/24080 describes a PHIP process in which parahydrogen is added across a symmetrical carbon-carbon double bond containing a $^{13}C$ centre. In one example of such a process, Wilkinson's catalyst is first reduced by addition of parahydrogen, followed by addition of an ethylene ligand. The resulting hydride ligands then undergo a migratory insertion reaction with the ethylene ligand, which subsequently dissociates from the complex to form uncoordinated hyperpolarised ethane. An overview of PHIP is given in Blazina et al, Dalton Trans., 2004, 2601-2609.

Conventional PHIP processes therefore involve the chemical addition of parahydrogen to hydrogenatable substrates (compounds), usually organic substrates (compounds) containing double and triple bonds. These processes are therefore limited to substrates (compounds) capable of undergoing hydrogenation. Furthermore, hydrogen equivalence is not preserved at all stages, which leads to some loss of hyperpolarisation through relaxation.

Currently the best reported catalyst for SABRE is [IrCl(COD)(IMes)][9], delivering $^1$H-signal enhancements of up to 4000 fold in methanol-$d_4$ solution where there is both high catalyst and p-$H_2$ solubility. While previous studies have shown that less toxic ethanol-$d_6$/$D_2O$ mixtures can be employed, the level of signal gain is typically reduced.[10] Feiters et al, prepared a water soluble catalyst for use with SABRE but the resulting enhancements in water were again weak when compared to those in methanol.[11] Others have further modified this approach but low activity has proven to be a common issue.[12]

However, we have now surprisingly found that the principles of phase transfer catalysis can be used to dramatically improve the SABRE response in water whilst simultaneously achieving catalyst separation (Scheme 1).

SUMMARY OF THE INVENTION

Thus, according to a first aspect of the invention there is provided a method for the preparation of an aqueous imaging medium, said method comprising the steps of
(i) preparing a multiphasic solvent system comprising an aqueous component and a non-aqueous component, said solvent comprising a target substrate and a (SABRE) hyperpolarisation transfer catalyst;
(ii) adding $H_2$ or parahydrogen (p-$H_2$) gas to the solvent system;
(iii) agitating the solvent system to form an emulsion comprising the aqueous component and the non-aqueous component thereby transferring the spin order from the hyperpolarisation transfer catalyst to the target substrate;
(iv) if the target substrate is in the non-aqueous component adjusting the pH and/or the temperature to extract the target substrate into the aqueous component; and
(v) adding a solvent phase-separation promoter; and
(vi) separating the non-aqueous component and the aqueous component wherein the aqueous component contains the hyperpolarised target substrate and provides an aqueous imaging medium.

In one particular aspect of the invention the multiphasic solvent system is a biphasic solvent system.

According to one aspect of the invention the target substrate is not water soluble and therefore, both the target substrate and the (SABRE) hyperpolarisation transfer catalyst are in the non-aqueous component. In such a case after hyperpolarisation has transferred to the target substrate the pH of the solvent system may be adjusted so as to allow the target substrate to be extracted into the aqueous component.

In this aspect of the invention the adjustment of the pH may comprise the addition of acid of base to the solvent system. Furthermore in the presence of acid it would be unlikely that the target substrate will polarise because the substrate may be protonated, hence the target substrate may no longer bind to the hyperpolarisation transfer catalyst.

This can be achieved when both solvents are present together but the utilization of the separate steps reflects a refinement where hyperpolarisation transfer can occur prior to extraction of the target substrate into the aqueous component. Furthermore, it is anticipated that the addition of salts or organic species, such as citric acid, that change the pH (acid or base) will be beneficial in also extending the relaxation time of the target substrate.

According to a preferred aspect of the invention the target substrate is water soluble therefore the target substrate is in both the aqueous component and the non-aqueous component while the (SABRE) hyperpolarisation transfer catalyst resides mainly or solely in the non-aqueous component.

Non-Aqueous Component

The non-aqueous component will generally comprise a solvent that is immiscible with water. Such water immiscible solvents will generally comprise non-polar organic solvents. Examples of such water immiscible solvents include, but shall not be limited to aromatic solvents, such as benzene and toluene; halogenated hydrocarbons solvents, such as chloroform and dichloromethane. Other examples of solvents include, but are not limited to, n-butanol, dichloromethane, methyl-t-butyl ether, ethyl acetate or 2-butanone.

The ratio of the aqueous component and the non-aqueous component may vary depending, inter alia, upon the nature of the target substrate. The ratio of aqueous component to non-aqueous component will generally be from about 0.1:1 to about 10:1 v/v.

Generally, the ratio of aqueous component to non-aqueous component will be selected to maximise the degree of hyperpolarisation of the target substrate; and/or to maximise the speed of phase separation; and/or the concentration of hyperpolarised agent that ultimately sits in the aqueous phase.

Furthermore, the choice of solvent and/or the ratio of the aqueous component and the non-aqueous component may be varied to maximise the relaxation time of the hyperpolarised substrate in the aqueous phase. For example, relaxation may be maximized by utilising $D_2O$ instead of water. The use of $D_2O$ as herein described shall include using a mixture of $D_2O$ and water, for example in a ratio of $D_2O$:$H_2O$ of about 1:1 v/v, but could span any proportion. In addition, relaxation time may be maximized by addition of a further co-solvent. An example of such co-solvents includes, but shall not be limited to ethanol or $d_6$-ethanol.

(SABRE) Hyperpolarisation Transfer Catalyst

The (SABRE) hyperpolarisation transfer catalyst may be selected from those known in the art. Thus, the (SABRE) hyperpolarisation transfer catalyst may be a homogeneous or heterogeneous hyperpolarisation transfer catalyst.

The nature of the catalyst may vary, but may, for example, take the form of a conventionally known hydrogenation catalyst. Thus, such catalysts may be homogeneous catalysts, for example, Wilkinson's catalyst, or heterogeneous catalysts, such as Pd on carbon. Thus, such homogeneous catalysts may include, but shall not be limited to, rhodium based catalysts, such as Wilkinson's catalyst and iridium based catalysts, such as Crabtree's catalyst. Heterogeneous catalysts may comprises one or more platinum group metals, particularly platinum, palladium, rhodium and ruthenium, precious metal catalysts, such as silver or gold, or non-precious metal catalysts, such as those based on nickel, e.g. Raney nickel.

Preferred (SABRE) hyperpolarisation transfer catalysts are thus described in our co-pending application No. PCT/GB2009/002860. Such catalysts include, for example, Ir(Cl(COD)IMes and analogues thereof. Alternatively, the (SABRE) hyperpolarisation transfer catalyst may comprise a $^2$H-labelled counterpart of Ir(Cl(COD)IMes or a catalyst optimised to work in the non-aqueous phase with the selected substrate. It may also come from the examples herein described.

IMes
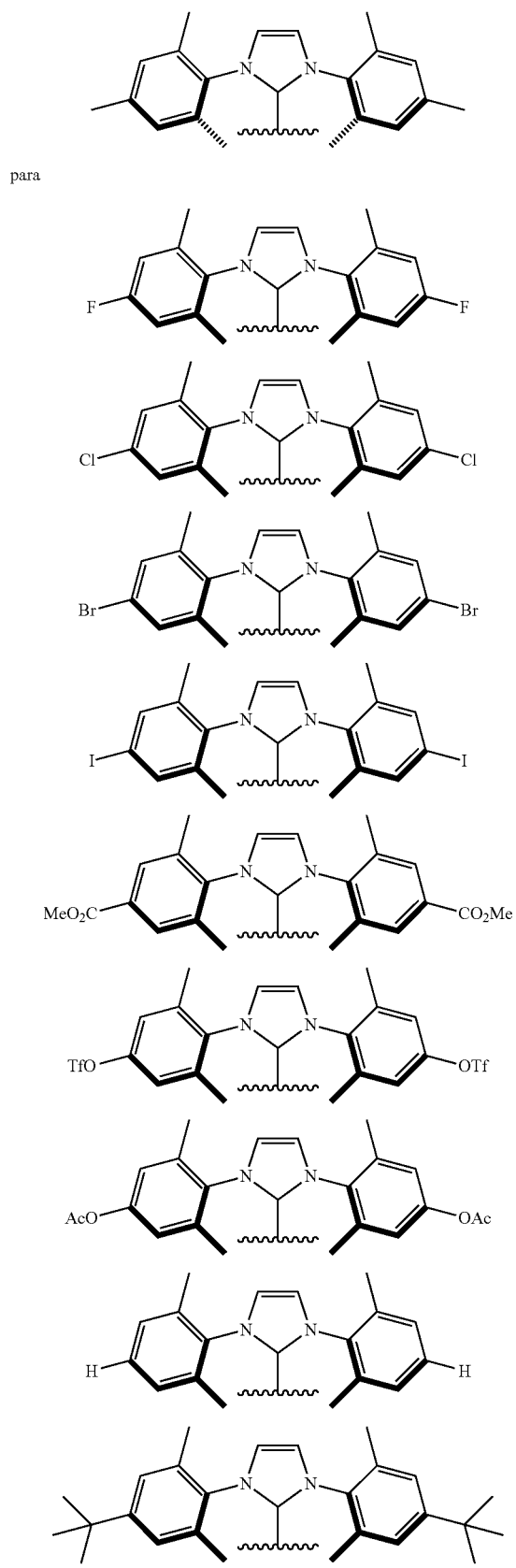
para
meta
ortho
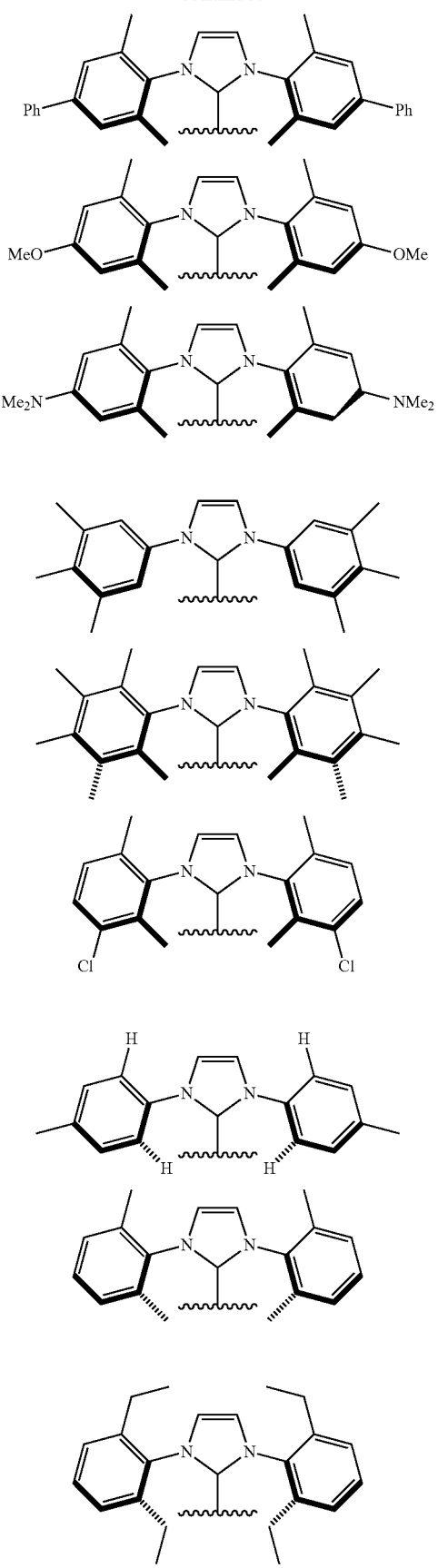

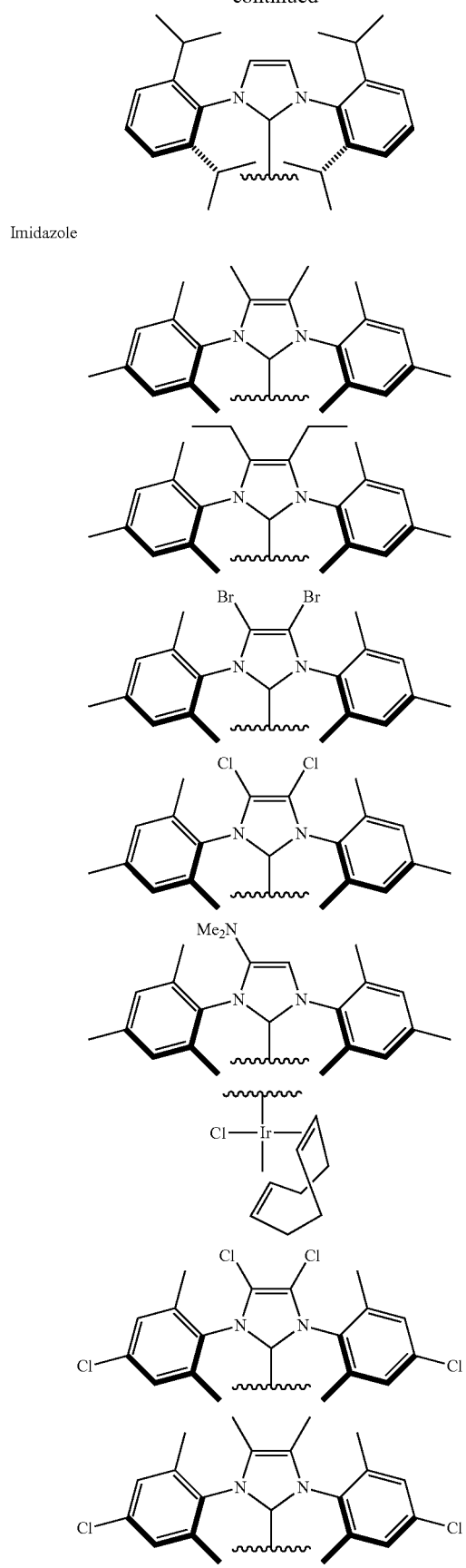
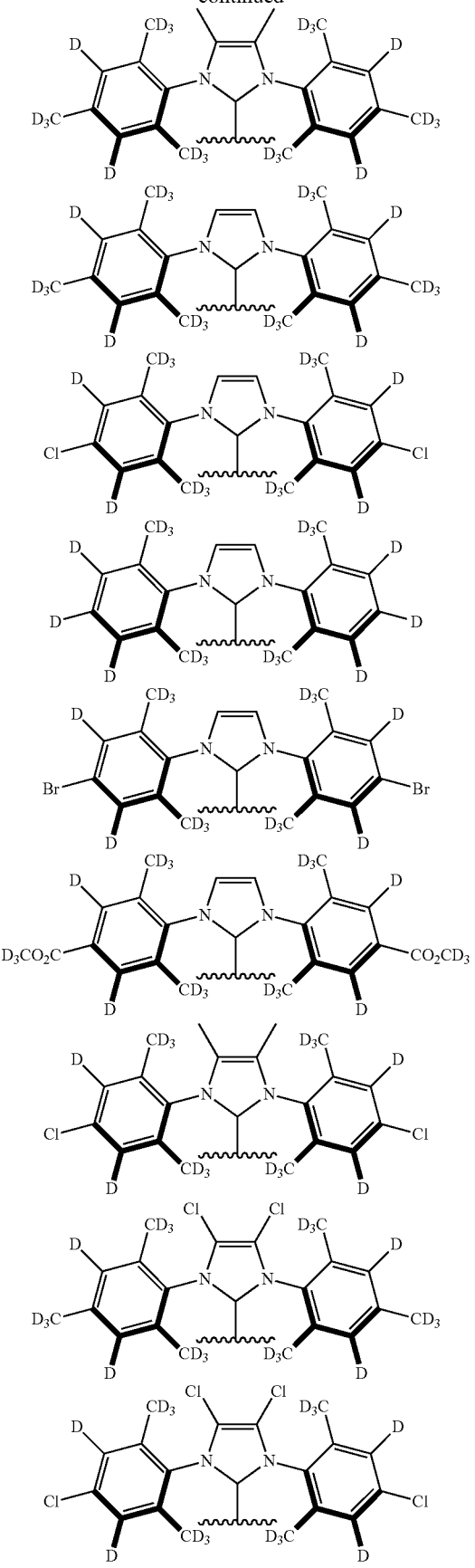

-continued

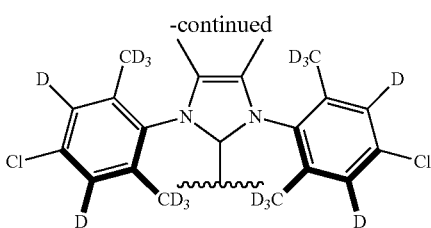

These species are often referred to a precatalysts because they are stable they become active during the catalytic process, in this case through their reaction with the target substrate and $H_2$ Target Substrate The target substrate will generally contain its spin 1/2 nuclei (e.g. $^1H$, $^{13}C$, $^{31}P$, $^{15}N$ or $^{19}F$) at the natural abundance level. The selected target will contain appropriate $^2H$ or Cl or O labels to maximise the relaxation times of the nuclei spins that are to be hyperpolarised (e.g. $^1H$, $^{13}C$, $^{31}P$, $^{15}N$, $^{29}Si$ or $^{19}F$). The selected target will contain appropriate $^{13}C$ or $^{15}N$ labelling to maximise the proportion of the target that can be created in a hyperpolarised NMR visible form in conjunction with appropriate $^2H$, O or Cl labelling to extend their magnetic state lifetimes. The selected target will contain spin pairs of appropriate $^1H$, $^{13}C$, $^{31}P$, $^{15}N$, $^{29}Si$ or $^{19}F$ labels to enable the formation of long-live states (singlet states) between the corresponding spin pairs (e.g. $^1H$, $^{13}C$, P, $^{15}N$, $^{29}Si$ or $^{19}F$) within a molecular scaffold that contains appropriate $^2H$ or Cl labelling to extend their lifetime. In the case where the target substrate contains pairs, these may be homo-nuclear or hetero-nuclear in nature. Examples, of such pairs include, but shall not be limited to $^1H/^1H$, $^1H/^{13}C$, $^1H/^{19}F$, $^1H/^{15}N$ or $^{13}C/^{13}C$ or any other combination of spin one half nuclei.

Examples of such hyperpolarisation targets include, but shall not be limited to nicotinamide, nicotine, pyrazine, 5-methyl pyrimidine or any suitable reagent, or mixture of reagents, that is known in the art to be capable of being hyperpolarised through SABRE, to produce an appropriate concentration of substrate for detection.

Forming an Emulsion

Agitation of the resulting solution to create the mixing necessary for hyperpolarisation transfer may comprise of stirring, shaking or the application of ultrasound or a combination thereof under a pressure of parahydrogen gas.

Adding Parahydrogen and Catalyst Activation

The addition of $H_2$ or parahydrogen (p-$H_2$) gas to the solvent may take place prior to the solvent system being agitated or may take place concurrent with agitation. Catalyst activation under parahydrogen may take place prior to the final hyperpolarisation transfer step or be part of the hyperpolarisation transfer step.

Solvent Phase-Separation Promoter

Any known phase-separation promoter may be used. Desirably such a phase-separation promoter will be suitable for in vivo use and therefore should be suitable to achieve physiological conditions. In addition, the phase-separation promoter should be suitable to withstand variations in pH which may be desirable to achieve optimal SABRE. Selection of the phase-separation promoter may also be desirable to optimise organic phase extraction; and/or to optimise the speed of phase-separation.

Examples of phase-separation promoters include alkali metal salts, such as sodium or potassium salts; or alkaline earth metal salts, such as calcium. Alkali metal salts are preferred, such as NaCl, or $NaO_2CCH_3$, NaOH, $NaHCO_3$ or $Na_2(CO_3)$. A further phase-separation promoters may comprise an alcohol such as ethanol.

The amount of phase-separation promoters may vary depending, inter alia, upon the nature of the phase-separation promoters, the nature of hyperpolarisation target, etc. When the aim is to create a biocompatible system, NaCl or KCl may be used as a phase-separation promoter to produce a saline or saline-like solution. Therefore, the amount of the phase-separation promoter may vary depending upon, inter alia, the nature of the phase-separation promoter. Generally, the phase-separation promoter may be from about 0.33% w/v to about 9% w/v. However, it will be understood by the person skilled in the art that more or less of the phase-separation promoter may be included, as required.

According to a further aspect of the invention there is provided a method of producing a hyperpolarised target substrate in an aqueous imaging medium, said method comprising the steps of (i) preparing a multiphasic solvent system comprising an aqueous component and a non-aqueous component, said solvent comprising a target substrate and a (SABRE) hyperpolarisation transfer catalyst;

(ii) adding $H_2$ or parahydrogen (p-$H_2$) gas to the solvent system;

(iii) agitating the solvent system to form an emulsion comprising the aqueous component and the non-aqueous component thereby transferring the spin order from the hyperpolarisation transfer catalyst to the target substrate;

(iv) if the target substrate is in the non-aqueous component adjusting the pH to extract the target substrate into the aqueous component; and (v) adding solvent phase-separation promoter;

(vi) separating the non-aqueous component and the aqueous component wherein the aqueous component contains the hyperpolarised target substrate and provides an aqueous imaging medium; and (vii) performing SABRE by replacing the $H_2$ gas with p-$H_2$ to create a hyperpolarised agent whilst agitating the mixture.

According to a yet further aspect of the invention there is provided a method of producing a hyperpolarised target substrate in an aqueous imaging medium, said method comprising the steps of:

(i) preparing a solvent system comprising an aqueous component and a non-aqueous component, said solvent comprising a target substrate and a (SABRE) hyperpolarisation transfer catalyst;

(ii) adding $H_2$ or parahydrogen (p-$H_2$) gas to the solvent system;

(iii) agitating the solvent system to form an emulsion comprising the aqueous component and the non-aqueous component thereby transferring the spin order from the hyperpolarisation transfer catalyst to the target substrate;

(iv) if the target substrate is in the non-aqueous component adjusting the pH to extract the target substrate into the aqueous component; and (v) adding solvent phase-separation promoter;

(vi) separating the non-aqueous component and the aqueous component wherein the aqueous component contains the hyperpolarised target substrate and provides an aqueous imaging medium;

(vii) performing SABRE by replacing the $H_2$ gas with p-$H_2$ to create a hyperpolarised agent whilst agitating the mixture;

(viii) optimising the solvent composition; and
(ix) optimising the phase separation promoter and it loading.

In one particular aspect of the invention the multiphasic solvent system is a biphasic solvent system.

According to one aspect of the invention the target substrate is not water soluble and therefore, both the target substrate and the (SABRE) hyperpolarisation transfer catalyst are in the non-aqueous component. In such a case after hyperpolarisation has transferred to the target substrate the pH of the solvent system may be adjusted so as to allow the target substrate to be extracted into the aqueous component.

According to a preferred aspect of the invention the target substrate is water soluble therefore the target substrate is in the aqueous component and the (SABRE) hyperpolarisation transfer catalyst is in the non-aqueous component.

According to this aspect of the invention the method generally comprises optimally transferring polarisation in low field to the nuclei of the target substrate e.g. $^{1}H$, $^{13}C$, $^{31}P$, $^{15}N$, $^{29}Si$ or $^{19}F$.

The polarisation transfer as herein described may be optimised by controlling one or more of
(i) the temperature;
(ii) the pressure of $H_2$ or appropriate buffer gas such as $N_2$;
(iii) the rate of agitation/speed of stirring;
(iv) the magnetic field experience by the system;
(v) the time of parahydrogen exposure; and/or
(vi) the concentration of the hyperpolarisation transfer catalyst and/or the target substrate.

The aforementioned method may optionally be carried out in conjunction with using a spin lock or ultra-low field transfer to create long-lived magnetisation of the singlet type between pairs of spins (e.g. $^{1}H$-$^{1}H$, $^{13}C$-$^{13}C$, $^{15}N$-$^{15}N$ or $^{1}H$-$^{13}C$, $^{15}N$-$^{13}C$, etc.) via ultra-low field transfer, or the application of r.f. excitation to the initially created SABRE hyperpolarised state.

The method will usually comprise waiting an appropriate amount of time to allow the aqueous component and the non-aqueous component of the solvent system to separate.

Optionally, the method may comprise the use of an in-line probe, e.g. a UV probe, if needed, to establish that the catalyst concentration is sufficiently low for in vivo injection. Advantageously, according to the method of the invention it has been found that no [none detectable] remaining hyperpolarisation transfer catalyst can be found in the separated aqueous component of the solvent system. The use of an in-line probe as herein described makes full use of the fact that the hyperpolarisation transfer catalyst is no longer present in the aqueous component and therefore unable to promote the relaxation of the target substrate in the aqueous phase/aqueous component, thereby maximising longevity of the resulting hyperpolarised signal.

If the concentration of the hyperpolarisation transfer catalyst in the separated aqueous component remains too high, it is within the scope of the present invention to add a catalyst deactivator to facilitate catalyst transfer to the non-aqueous phase/non-aqueous component. An example of a catalyst deactivator is a chelating ligand, such as 2,2'-bipyridine and 1,10-phenanthroline.

Using an appropriate delivery device to procure the hyperpolarised substrate detection by NMR or MRI may facilitate one or more of the following:
(i) after an appropriate amount removing a sample of the hyperpolarised substrate from the aqueous component;
(ii) use UV monitoring to assess suitability immediately prior to sample removal or after sample removal;
(iii) use pH monitoring to assess suitability immediately prior to sample removal or after sample removal;
(iv) employ filtration to achieve sterility after sample removal; and
(v) injection or transport of the sample into a target for subsequent detection by NMR or MRI, where the target might be a suitable sample tube, an animal or a human.

According to a further aspect of the invention there is provided a pharmaceutically acceptable formulation comprising an aqueous solution of a hyperpolarised substrate for use as an imaging medium.

In a preferred aspect of the invention the pharmaceutically acceptable formulation comprises an aqueous solution of a hyperpolarised substrate and a solvent phase-separation promoter for use as an imaging medium. Such a formulation may preferably comprise a saline solution of a hyperpolarised substrate for use as an imaging medium.

According to this aspect of the invention there is provided an imaging medium for in vivo magnetic resonance (MR) detection comprising a hyperpolarised substrate in an aqueous solution. In a preferred aspect the imaging medium comprises a hyperpolarised substrate and a solvent phase-separation promoter in an aqueous solution. According to this aspect of the invention there is especially provided an imaging medium as herein described comprising a hyperpolarised substrate in a saline solution.

According to another aspect of the invention there is provided an instrument for automated agent delivery for in vivo magnetic resonance (MR) detection.

According to this aspect of the invention the instrument for automated in vivo magnetic resonance (MR) detection comprises a mixing chamber for a multiphasic solvent system, said mixing chamber adapted to be positioned in a magnetic field; said mixing chamber adapted to be connected to:
a parahydrogen source and a pressure regulator;
a water input supply;
a solvent input supply;
mans for generating an emulsion;
acid/base input supply and a pH meter;
optionally means for adding a solvent phase-separation promoter;
means for a separating the multiphasic solvent system; and
an aqueous imaging medium outlet to an in vivo sample delivery system.

More particularly, the instrument as herein described is as represented schematically in accompanying figure S76.

The invention will now be illustrated by way of example only and with reference to the accompanying drawings, in which:

Scheme 1 illustrates the partitioning of the SABRE catalyst and hyperpolarisation target between the two immiscible phases of chloroform and water allows the principles of phase-transfer catalysis to be employed in conjunction with parahydrogen to produce high levels of hyperpolarisation in the aqueous phase without catalyst contamination;

Figure S1 is a schematic drawing of the NMR tube containing the sample and the position of the two voxels used for spectra acquisition;

Figure S2 is the $^{1}H$ NMR spectra of 2a. Top: Boltzmann equilibrium conditions. Bottom: SABRE hyperpolarised;

Figure S3 is the $^{1}H$ NMR spectra of 2b. Top: Boltzmann equilibrium conditions. Bottom: SABRE hyperpolarised;

Figure S4 is the $^{1}H$ NMR spectra of 2c. Top: Boltzmann equilibrium conditions. Bottom: SABRE hyperpolarised;

Figure S5 is the $^1$H NMR spectra of 2d. Top: Boltzmann equilibrium conditions. Bottom: SABRE hyperpolarised;

Figure S6 is the $^1$H NMR spectra of 2e. Top: Boltzmann equilibrium conditions. Bottom: SABRE hyperpolarised;

Figure S7 is the $^1$H NMR spectra of 2f. Top: Boltzmann equilibrium conditions. Bottom: SABRE hyperpolarised;

Figure S8 is the $^1$H NMR spectrum of 3a acquired under thermal equilibrium conditions (x512);

Figure S9 illustrates the pyrazine signal acquired hyperpolarised under SABRE immediately after the polarisation transfer step (top) and 30 seconds after the polarisation transfer step (bottom) when complete separation has occurred;

Figure S10 is the. $^1$H NMR spectrum of pyrazine acquired in thermal equilibrium conditions (x512);

Figure S11 is the. $^1$H NMR spectrum of 3b hyperpolarised under SABRE, acquired immediately after the polarisation transfer step (middle) and 30 seconds after the polarisation transfer step (bottom) when complete separation has occurred;

Figure S12 is the. $^1$H NMR spectrum of 3c acquired in thermal equilibrium conditions (x512);

Figure S13 is the $^1$H NMR spectrum of 3c hyperpolarised under SABRE, acquired immediately after the polarisation transfer step (top) and 30 seconds after the polarisation transfer step (bottom) when complete separation has occurred;

Figure S14 is the $^1$H NMR spectrum of 3d acquired in thermal equilibrium conditions (x512);

Figure S15 is the $^1$H NMR spectrum of 3d hyperpolarised under SABRE, acquired immediately after the polarisation transfer step (top) and 30 seconds after the polarisation transfer step (bottom) when complete separation has occurred;

Figure S16 is the $^1$H NMR spectrum of 3e acquired in thermal equilibrium conditions (x512);

Figure S17 is the $^1$H NMR spectrum of 3e hyperpolarised under SABRE, acquired 30 seconds after the polarisation transfer step, when complete separation has occurred;

Figure S18 illustrates the pyrazine signal acquired in Boltzmann equilibrium conditions (top, x256) and hyperpolarised under SABRE, acquired immediately after the polarisation transfer step (middle) and 30 seconds after the polarisation transfer step (bottom) when complete separation has occurred;

Figure S19 illustrates the pyrazine signal acquired in Boltzmann equilibrium conditions (top, x 256) and hyperpolarised under SABRE acquired 30 seconds after the polarisation transfer step (bottom) when complete separation has occurred;

Figure S20 is the 1D projection of $^2$H signal showing the distribution of solvents in the NMR tube prior to the shaking process;

Figure S21 is the 1D projection of the pyrazine signal after shaking the sample for 10 seconds as a function of time (Left) thermal equilibrium conditions; and (Right) SABRE hyperpolarised;

Figure S22 is the (Left) 1D projection of $^2$H signal showing the distribution of solvents in the NMR tube prior to the shaking process; and (Right) the 1D projections of the $^1$H signal as a function of time;

Figure S23 is the 1D projection of the pyrazine signal after shaking the sample for 10 seconds as a function of time (Left) thermal equilibrium conditions; and (Right) SABRE hyperpolarised;

Figure S24 is the (Left) 1D projection of $^2$H signal showing the distribution of solvents in the NMR tube prior to the shaking process; and (Right) the 1D projections of the 1H signal as a function of time;

Figure S25 is the 1D projection of the pyrazine signal after shaking the sample for 10 seconds as a function of time (Left) thermal equilibrium conditions; and (Right) SABRE hyperpolarised;

Figure S26 is the (Left) 1D projection of $^2$H signal showing the distribution of solvents in the NMR tube prior to the shaking process; and (Right) the 1D projections of the H signal as a function of time;

Figure S27 is the 1D projection of the pyrazine signal after shaking the sample for 10 seconds as a function of time (Left) thermal equilibrium conditions; and (Right) SABRE hyperpolarised;

Figure S28 is the (Left) 1D projection of $^2$H signal showing the distribution of solvents in the NMR tube prior to the shaking process; and (Right) the 1D projections of the $^1$H signal as a function of time;

Figure S29 is the 1D projection of the pyrazine signal after shaking the sample for 10 seconds as a function of time (Left) thermal equilibrium conditions; and (Right) SABRE hyperpolarised;

Figure S30 is the (Left) 1D projection of $^2$H signal showing the distribution of solvents in the NMR tube prior to the shaking process; and (Right) 1D projections of the $^1$H signal as a function of time;

Figure S31 is the 1D projection of the pyrazine signal after shaking the sample for 10 seconds as a function of time (Left) thermal equilibrium conditions; and (Right) SABRE hyperpolarised;

Figure S32 is the (Left) 1D projection of $^2$H signal showing the distribution of solvents in the NMR tube prior to the shaking process; and (Right) 1D projections of the $^1$H signal as a function of time;

Figure S33 is the 1D projection of the pyrazine signal after shaking the sample for 10 seconds as a function of time (Left) thermal equilibrium conditions; and (Right) SABRE hyperpolarised;

Figure S34 is the (Left) 1D projection of $^2$H signal showing the distribution of solvents in the NMR tube prior to the shaking process; and (Right) 1D projections of the $^1$H signal as a function of time;

Figure S35 is the 1D projection of the pyrazine signal after shaking the sample for 10 seconds as a function of time (Left) thermal equilibrium conditions; and (Right) SABRE hyperpolarised;

Figure S36 is the (Left) 1D projection of $^2$H signal showing the distribution of solvents in the NMR tube prior to the shaking process; and (Right) the 1D projections of the $^1$H signal as a function of time;

Figure S37 is the 1D projection of the pyrazine signal after shaking the sample for 10 seconds as a function of time (Left) thermal equilibrium conditions; and (Right) SABRE hyperpolarised;

Figure S38 is the (Left) 1D projection of 2H signal showing the distribution of solvents in the NMR tube prior to the shaking process; and (Right) 1D projections of the $^1$H signal as a function of time;

Figure S39 is the 1D projection of the pyrazine signal after shaking the sample for 10 seconds as a function of time (Left) thermal equilibrium conditions; and (Right) SABRE hyperpolarised;

Figure S40 is the (Left) 1D projection of $^2$H signal showing the distribution of solvents in the NMR tube prior to the shaking process; and (Right) 1D projections of the $^1$H signal as a function of time;

Figure S41 is the 1D projection of the pyrazine signal after shaking the sample for 10 seconds as a function of time (Left) thermal equilibrium conditions; and (Right) SABRE hyperpolarised;

Figure S42 is the (Left) 1D projection of $^2$H signal showing the distribution of solvents in the NMR tube prior to the shaking process; and (Right) 1D projections of the $^1$H signal as a function of time;

Figure S43 is the 1D projection of the pyrazine signal after shaking the sample for 10 seconds as a function of time (Left) thermal equilibrium conditions; and (Right) SABRE hyperpolarised;

Figure S44 is the (Left) 1D projection of $^2$H signal showing the distribution of solvents in the NMR tube prior to the shaking process; and (Right) 1D projections of the $^1$H signal as a function of time;

Figure S45 is the 1D projection of the pyrazine signal after shaking the sample for 10 seconds as a function of time (Left) thermal equilibrium conditions; and (Right) SABRE hyperpolarised;

Figure S46 is the 1D projection of 2H signal showing the distribution of solvents in the NMR tube prior to the shaking process; and (Right) 1D projections of the $^1$H signal as a function of time;

Figure S47 is the 1D projection of the pyrazine signal after shaking the sample for 10 seconds as a function of time (Left) thermal equilibrium conditions; and (Right) SABRE hyperpolarised, measured after 30 s from the shaking process;

Figure S48 is the (Left) 1D projection of $^2$H signal showing the distribution of solvents in the NMR tube prior to the shaking process; and (Right) 1D projections of the $^1$H signal as a function of time;

Figure S49 is the 1D projection of the pyrazine signal after shaking the sample for 10 seconds as a function of time (Left) thermal equilibrium conditions; and (Right) SABRE hyperpolarised, measured after 20 s from the shaking process;

Figure S50 is the 1D projection of 2H signal showing the distribution of solvents in the NMR tube prior to the shaking process; and (Right) 1D projections of the $^1$H signal as a function of time;

Figure S51 is the 1D projection of the pyrazine signal after shaking the sample for 10 seconds as a function of time (Left) thermal equilibrium conditions; and (Right) SABRE hyperpolarised, measured after 20 s from the shaking process;

Figure S52 is the 1D projection of the pyrazine signal after shaking the sample for 10 seconds as a function of time measured after 20 s from the shaking process and after adding another 4.5 mg NH$_4$Cl;

Figure S53 is the (Left) 1D projection of 2H signal showing the distribution of solvents in the NMR tube prior to the shaking process; and (Right) 1D projections of the $^1$H signal as a function of time;

Figure S54 is the 1D projection of the substrate signal after shaking the sample for 10 seconds as a function of time after adding p-H$_2$;

Figure S55 is the 1D projection of 2H signal showing the distribution of solvents in the NMR tube prior to the shaking process;

Figure S56 is the 1D projection of the substrate signal after shaking the sample for 10 seconds as a function of time (Left) thermal equilibrium conditions; and (Right) SABRE hyperpolarised;

Figure S57 is the 1D projection of $^2$H signal showing the distribution of solvents in the NMR tube prior to the shaking process;

Figure S58 is the 1D projection of the substrate signal after shaking the sample for 10 seconds as a function of time (Left) thermal equilibrium conditions; and (Right) SABRE hyperpolarised;

Figure S59 is the (Left) 1D projection of $^2$H signal showing the distribution of solvents in the NMR tube prior to the shaking process; and (Right) 1D projections of the $^1$H signal as a function of time;

Figure S60 is the 1D projection of the substrate signal after shaking the sample for 10 seconds as a function of time (Left) thermal equilibrium conditions; and (Right) SABRE hyperpolarised;

Figure S61 is the (Left) 1D projection of $^2$H signal showing the distribution of solvents in the NMR tube prior to the shaking process; and (Right) 1D projections of the $^1$H signal as a function of time;

Figure S62 is the 1D projection of the substrate signal after shaking the sample for 10 seconds as a function of time (Left) thermal equilibrium conditions; and (Right) SABRE hyperpolarised;

Figure S63 is the (Left) 1D projection of $^2$H signal showing the distribution of solvents in the NMR tube prior to the shaking process; and (Right) 1D projections of the $^1$H signal as a function of time;

Figure S64: is the 1D projection of the substrate signal after shaking the sample for 10 seconds as a function of time (Left) thermal equilibrium conditions; and (Right) SABRE hyperpolarised;

Figure S65: is $^1$H NMR spectra of 3h acquired in thermal equilibrium conditions (top, x 256) and SABRE hyperpolarised (bottom) at 310 K;

Figure S66: 1D projection of the substrate signal (3h) after shaking the sample for 10 seconds as a function of time at a). 268 K, b). 298 K, c). 310 K and d). 320 K;

Figure S67 is 1D MRI projections of the $^1$H SABRE hyperpolarised signal of pyrazine (2i);

Figure S68 is 1D MRI projections of the $^1$H SABRE hyperpolarised signal of pyrazine, the samples have been prepared using 17-fold excess of ligand (Left) 2g; and (Right) 2h;

Figure S69 is 2D RARE images of the $^1$H SABRE hyperpolarised signal of pyrazine (2i) (Left) thermal equilibrium; and (Right) hyperpolarised;

Figure S70 is 2D RARE images of the $^1$H SABRE hyperpolarised signal of pyrazine (2g) (Left) thermal equilibrium; and (Right) hyperpolarised;

Figure S71 is 2D RARE images of the $^1$H SABRE hyperpolarised signal of pyrazine (2h) (Left) thermal equilibrium; and (Right) hyperpolarised;

Figure S72 is 2D MRI images of the $^1$H SABRE hyperpolarised signal of pyrazine as a function of time. Images have been acquired (from top to bottom) after 0.8, 1.6, 2.4 and 3.2 s from inserting the sample into the imaging system (Left) 2i, (Middle) 2g; and (Right) 2h;

Figure S73 is the SVS of pyrazine in water as a function of substrate excess;

Figure S74 is 1D MRI projections of the $^1$H SABRE hyperpolarised signal of pyrazine (Left) 3f 1-fold excess, 3.3 mg NH$_4^+$CH$_3$COO; and (Right) 3g 17-fold excess, 3.3 mg NH$_4^+$CH$_3$COO$^-$, 1 mg NaCl;

Figure S75 is 2D MRI images the $^1$H signal of pyrazine (1-fold excess+3.3 mg NH$_4^+$CH$_3$COO$^-$ (3f)) (from left to right) sagittal image of the whole tube, axial projection (5 mm slice) through the part of the tube containing CDCl$_3$, axial projection (5 mm slice) through the part of the tube containing $D_2O$. Top: thermal equilibrium conditions, bottom: SABRE hyperpolarised;

Figure S76 is 2D MRI images the H signal of pyrazine (17-fold excess+3.3 mg $NH_4^+CH_3COO^-$+1 mg NaCl, 3g). From left to right: sagittal image of the whole tube, axial projection (5 mm slice) through the part of the tube containing $CDCl_3$, axial projection (5 mm slice) through the part of the tube containing $D_2O$. Top: thermal equilibrium conditions, bottom: SABRE hyperpolarised;

Figure S77 is (a) UV-visible spectrum of chloroform layer after dilution (100 times). In this layer the catalyst characterized by two absorption bands at $\lambda_1=374$ nm ($\epsilon=6800$ $l \cdot mol^{-1} \cdot cm^{-1}$) and $\lambda_2=500$ nm ($\epsilon=2200$ $l \cdot mol^{-1} \cdot cm^1$) and pyrazine at $\lambda_1=261$ nm. (b) UV-visible of $D_2O$ layer after dilution of 10 times; in this layer, the pyrazine was the main product;

Figure S78 is $^1H$ NMR spectra of pz. (a) Boltzmann equilibrium conditions (x64 vertical expansion relative to (b)), (b) SABRE hyperpolarised trace detailing a 1500-fold signal enhancement;

Figure S79 is a $^1H$ NMR spectra of pz. (a) Boltzmann equilibrium conditions (x128 vertical expansion relative to (b)), (b) SABRE hyperpolarised trace detailing a 1300-fold signal enhancement;

Figure S80 is a 1D projection of the $^1H$ NMR signal showing the hyperpolarised pz in water and $CD_2Cl_2$ after complete phase separation;

Figure S81 is a $^1H$ NMR spectra of 3-fluoropyridine. (a) Boltzmann equilibrium conditions (x64 vertical expansion relative to (b)), (b) SABRE hyperpolarised trace detailing a 500-fold signal enhancement;

Figure S82 is (a) 1D projection of the $^1H$ NMR signal showing the hyperpolarised 3-fluoropyridine in water and $CD_3Cl$ after complete separation. (b) 1D projection of the corresponding $^1H$ NMR signal collected under Boltzmann equilibrium conditions;

Figure S83 is a $^1H$ NMR spectra of pyridazine. (a) Boltzmann equilibrium conditions (x32 vertical expansion relative to (b)), (b) SABRE hyperpolarised trace detailing a 200-fold signal enhancement;

Figure S84 is (a) 1D projection of the $^1H$ NMR signal showing the hyperpolarised pyridazine in water and $CD_3Cl$ after complete separation. (b) 1D projection of the H NMR signal resulting at Boltzmann equilibrium conditions (x64 vertical expansion relative to (a));

Figure S85 is a $^1H$ NMR spectra of pyridazine (a) Boltzmann equilibrium conditions (x16 vertical expansion relative to (b)), (b) SABRE hyperpolarised trace detailing 200-fold signal enhancement;

Figure S86 is a $^1H$ NMR spectra of pyridazine (a) Boltzmann equilibrium conditions (x32 vertical expansion relative to (b)), (b) SABRE hyperpolarised trace detailing a 400-fold signal enhancement;

Figure S87 is a $^1H$ NMR spectra of 4-aminopyridine (a) Boltzmann equilibrium conditions (x16 vertical expansion relative to (b)), (b) SABRE hyperpolarised trace detailing a 300-fold signal enhancement;

Figure S88 is a $^1H$ NMR spectra of $d_2$-nicotinamide. (a) Boltzmann equilibrium conditions (x32 vertical expansion relative to (b)), (b) SABRE hyperpolarised trace detailing a 600-fold signal enhancement;

Figure S90 is (a) 1D projection of the $^1H$ NMR signal showing the hyperpolarised $d_2$-nicotinamide in water and $CD_3Cl$ after complete separation. (b) 1D projection of the $^1H$ NMR signal resulting from Boltzmann equilibrium conditions (x32 vertical expansion relative to (a));

Figure S91 is a $^1H$ NMR spectra of $d_2$-nicotinamide. (a) Boltzmann equilibrium conditions (x2 vertical expansion relative to (b)), (b) SABRE hyperpolarised trace detailing a 400-fold signal enhancement;

Figure S92 is a $^1H$ NMR spectra of $d_2$-nicotinamide. (a) Boltzmann equilibrium conditions (x32 vertical expansion relative to (b)), (b) SABRE hyperpolarised trace detailing a 750-fold signal enhancement;

Figure S93 is a 1D projection of the $^1H$ NMR signal showing the hyperpolarised $d_2$-nicotinamide in water and $CD_3Cl$ after complete separation;

Figure S94 illustrates the extraction of $d_2$-methylnicotinate after SABRE hyperpolarisation;

Figure S95 is a $^1H$ NMR spectra of $d_2$-methylnicotinate after extraction by acidified $D_2O$. (a) Boltzmann equilibrium conditions (x64 vertical expansion relative to (b)), (b) SABRE hyperpolarised trace detailing a 750-fold signal enhancement;

Figure S96 is (A): SABRE $^{13}C$ response of pz in the water (blue) and chloroform (orange) phases after transfer at 30 G. (B): SABRE $^{15}N$ NMR pz response in the water (blue) and chloroform (orange) phases after transfer at ~0 G in a µ-metal shield;

Figure S97 is a 2D MRI images the $^1H$ signal of pyridazine (7-fold excess+20 mg NaCl). From left to right: sagittal image of the whole tube, axial projection through the part of the tube containing $CDCl_3$, axial projection through the part of the tube containing $D_2O$: Top: thermal equilibrium conditions, bottom: SABRE hyperpolarised;

Figure S98 is (a) UV-visible spectrum of the chloroform layer after dilution (100 times). In this layer the catalyst is characterized by two absorption bands at $\lambda_1=374$ nm ($\epsilon=6800$ $l \cdot mol^{-1} \cdot cm^{-1}$) and $\lambda_2=500$ nm ($\epsilon=2200$ $l \cdot mol^{-1} \cdot cm^{-1}$) with pyrazine providing the $\lambda_1$ 261 nm signal. (b) UV-visible spectrum of the $D_2O$ layer after dilution of 10 times. In this layer, the pyrazine proved to be the main product;

Figure S99 is a UV-visible response of the water phase that results 10 seconds after phase separation has started;

Figure S100 is a UV-visible response of pz in the chloroform phase as a function of time after the shake; and FIG. 101 is a schematic representation of a delivery system.

EXPERIMENTAL PROCEDURES

Materials

All of the experimental procedures associated with this work were carried out under nitrogen using standard Schlenk techniques. The solvents used were dried using an Innovative Technology anhydrous solvent system, or distilled from an appropriate drying agent under nitrogen. The catalyst precursor ([Ir(IMes)(COD)Cl] (1) employed in this work was synthesized by established procedures according to literature methods. Deuterated chloroform ($CDCl_3$), deuterated water ($D_2O$), deuterated ethanol (EtOD) and pyrazine (2) were purchased from Sigma Aldrich and used as supplied.

SABRE Analysis

All samples have been prepared in standard 5 mm NMR tubes equipped with Young taps. In a typical experiment set, arrays of NMR measurements were collected using either 4 equivalents of substrate (1-fold excess) to 5 mM of iridium or 20 equivalents of substrate (17-fold excess) to 5 mM iridium dissolved in mixtures of $CDCl_3$ and $D_2O$. The exact composition of each sample analysed is specified detailed in Table S1.

TABLE S1

Detailed composition of samples studied in this work.

| Sample ID | Ligand concentration [mmol] | CDCl$_3$ volume [μl] | D$_2$O volume [μl] | Additive | Additive Concentration [mmol] |
|---|---|---|---|---|---|
| Group 1 | | | | | |
| 1a | 0.012 | 600 | 0 | — | — |
| 1b | 0.012 | 500 | 100 | — | — |
| 1c | 0.012 | 400 | 200 | — | — |
| 1d | 0.012 | 300 | 300 | — | — |
| 1e | 0.012 | 200 | 400 | — | — |
| 1f | 0.012 | 100 | 500 | — | — |
| 1g | 0.012 | 20 | 580 | — | — |
| Group 2 | | | | | |
| 2a | 0.012 | 600 | 0 | — | |
| 2b | 0.012 | 400 | 200 | NaCl | 0.0170 |
| 2c | 0.012 | 300 | 300 | NaCl | 0.0170 |
| 2d | 0.012 | 200 | 400 | NaCl | 0.0170 |
| 2e | 0.012 | 100 | 500 | NaCl | 0.0170 |
| 2f | 0.012 | 250 | 350 | NaCl | 0.0085 |
| 2g | 0.060 | 300 | 300 | NaCl | 0.0170 |
| 2h | 0.060 | 300 | 300 | NaCl | 0.0340 |
| 2i | 0.060 | 300 | 300 | NaCl EtOD, 50μl | 0.0340 |
| Group 3 | | | | | |
| 3a | 0.012 | 300 | 300 | NaOH | 0.0085 |
| 3b | 0.012 | 300 | 300 | Na$_2$CO$_3$ | 0.0085 |
| 3c | 0.012 | 300 | 300 | NaHCO$_3$ | 0.0085 |
| 3d | 0.012 | 300 | 300 | CH$_3$COO$^-$Na$^+$ | 0.0085 |
| 3e | 0.012 | 300 | 300 | CH$_3$COO$^-$NH$_4$$^+$ | 0.0085 |
| 3f | 0.012 | 300 | 300 | NH$_4$$^+$Cl$^-$ | 0.0085 |
| 3g | 0.060 | 300 | 300 | NH$_4$$^+$Cl$^-$ NaCl | 0.0085 0.0170 |
| 3h | 0.030 | 300 | 300 | NaCl | 0.0500 |

After adding p-H$_2$ at 3 bar pressure, H NMR spectra were recorded using R/2 excitation pulses immediately after shaking the sample in a magnetic field of 65 G. Enhancement factors were calculated by using the ratio of the integral areas of individual resonances in the hyperpolarised spectrum and the spectrum collected under normal H$_2$ and Boltzmann equilibrium conditions respectively.

Similar experiments have been performed in order to assess the possibility to polarize heteronuclei such as $^{13}$C and $^{15}$N. $^{13}$C hyperpolarisation experiments have been performed using polarization transfer fields between 0 and 65 G, while $^{15}$N data has been acquired at 0 G field, by inserting the tube and shaking the sample in a μ-metal shield designed to shield the sample form the environmental magnetic field.

1D MRI Experiments

All 1D MRI experiments have been performed using a 400 MHz Bruker Avance spectrometer equipped with a z-gradient of maximum strength of 0.536 T/m. As a function of the observed nucleus, the experiments can be separated in two categories:

1D projections of the $^2$H signal amplitude on the z direction (parallel to the magnet bore and the NMR sample tube). These experiments have been performed with the purpose of observing the spatial distribution of the two solvents.

1D projections of the $^1$H signal amplitude on the z direction (parallel to the magnet bore and the NMR sample tube). In a typical experiment, 128 projections have been acquired immediately after the shaking process. These experiments have been performed with the purpose of observing the spatial distribution of the substrate in thermal equilibrium conditions, after shaking in the presence of o-H$_2$ and well as after shaking in the presence of p-H$_2$.

2D MRI Experiments

All 2D MRI experiments have been performed using a 400 MHz Bruker Avance spectrometer equipped with a micro imaging gradient set with maximum amplitude of 1 T/m and a double resonance birdcage coil with a diameter of 30 mm. All samples have been prepared in 10 mm diameter standard NMR tubes. The hyperpolarisation step has achieved by shaking the sample under p-H$_2$ for 10 seconds at 65G in the stray field of the magnet. Images have been acquired using the rapid acquisition schemes based on spin echoes (RARE) and gradient echoes respectively (Steady State Free Precession-SSFP). The $^1$H MRI acquisition parameters were, as follows:

For SSFP images: field of view 60×60 mm$^2$, slice thickness 2.5 mm, matrix size 64×64 (zero-filled to 128×128) leading to a nominal 2D resolution of 0.94×0.94 mm$^2$ (digital resolution 0.47×0.47 mm$^2$). TE/TR 2/4 ms. Repetition time between two consecutive image acquisition: 600 ms. Excitation pulse angle: 30°.

For RARE images: field of view 30×60 mm$^2$, slice thickness 2.5 mm, matrix size 64×64 (zero-filled to 128×128) leading to a nominal 2D resolution of 0.47×0.94 mm$^2$ (digital resolution 0.23×0.47 mm$^2$). TE/TE$_{eff}$/TR: 4/4/1100 ms. Echo train length: 64.

A sine bell squared filter has been applied prior to the Fourier transform to minimize the contribution of noise in the images. Data post processing has been done using home developed routines in Prospa (Magritek) and MATLAB (MathWorks).

Single Voxel Spectroscopy (SVS) Experiments

SVS experiments have been performed using the setup described in section 1.4. $^1$H SABRE hyperpolarised spectra of pyrazine have been acquired by selecting two separate voxels (matrix size 5×5×5 mm$^3$) located parallel to the tube's vertical axis, as depicted in Figure S1. In order to minimize artefacts caused by diffusion and turbulence on the time scale of the experiment, an outer volume suppression scheme (OVS) has been used prior to data acquisition.

Results and Discussion

1. NMR Spectroscopy Results 1.1 Optimization Experiments Performed on Pyrazine Dissolved in CDCl$_3$/D$_2$O Mixtures In order to determine the optimal composition of the biphasic solvent used for SABRE catalysis, H hyperpolarisation experiments have been performed on a series of samples in which the ratio of the inorganic to organic phase has been varied in a linear fashion. For each sample five up to ten hyperpolarisation experiments have been performed by shaking the sample in the stray field of the magnet at 30 G for 10 seconds and immediately acquiring a $^1$H spectrum after the hyperpolarisation transfer step has been completed. The enhancement factor was calculated as the average value of the integral areas of the hyperpolarised resonances divided by the corresponding area of the spectrum acquired in Boltzmann equilibrium conditions. The composition of each sample together with the corresponding enhancement and associated errors are presented in Table S2.

TABLE S2

Enhancements obtained for samples 1a-1g, together with the associated experimental errors.

| Sample | CDCl$_3$ Volume [μL] | D$_2$O Volume [μL] | Enhancement | Error [±] |
|---|---|---|---|---|
| 1a | 600 | 0 | 512 | 19 |
| 1b | 500 | 100 | 564 | 18 |
| 1c | 400 | 200 | 649 | 33 |
| 1d | 300 | 300 | 645 | 16 |
| 1e | 200 | 400 | 690 | 22 |
| 1f | 100 | 500 | 650 | 24 |
| 1g | 20 | 580 | 281 | 29 |

1.2 SABRE Hyperpolarisation of Pyrazine in CDCl$_3$/D$_2$O Mixtures in the Presence of NaCl.

Sample: 1-Fold Excess Pyrazine; CDCl$_3$:D$_2$O Ratio 0.6:0 (2a)

Figure S2. $^1$H NMR spectra of 2a. Top: Boltzmann equilibrium conditions. Bottom: SABRE hyperpolarised.

Sample: 1-Fold Excess Pyrazine; CDCl$_3$:D$_2$O Ratio 0.4:0.2 (2b)

Figure S3. $^1$H NMR spectra of 2b. Top: Boltzmann equilibrium conditions. Bottom: SABRE hyperpolarised.

Sample: 1-Fold Excess Pyrazine; CDCl$_3$:D$_2$O Ratio 0.3:0.3 (2c)

Figure S4. $^1$H NMR spectra of 2c. Top: Boltzmann equilibrium conditions. Bottom: SABRE hyperpolarised.

Sample: 1-Fold Excess Pyrazine; CDCl$_3$:D$_2$O Ratio 0.2:0.4 (2d)

Figure S5. $^1$H NMR spectra of 2d. Top: Boltzmann equilibrium conditions. Bottom: SABRE hyperpolarised.

Sample: 1-Fold Excess Pyrazine; CDCl$_3$:D$_2$O Ratio 0.1:0.5 (2e)

Figure S6. $^1$H NMR spectra of 2e. Top: Boltzmann equilibrium conditions. Bottom: SABRE hyperpolarised.

Sample: 1-Fold Excess Pyrazine; CDCl$_3$:D$_2$O Ratio 0.25:0.35 (2f)

Figure S7. $^1$H NMR spectra of 2f. Top: Boltzmann equilibrium conditions. Bottom: SABRE hyperpolarised.

1.3 SABRE Hyperpolarisation of Pyrazine in CDCl$_3$/D$_2$O Mixtures in the Presence of Other Salts.

Sample: 1-Fold Excess Pyrazine+NaOH (3a)

A sample was prepared using 1-fold excess of ligand relative to the active iridium catalyst (5 mM) in a mixture of 0.3 ml CDCl$_3$ and 0.3 D$_2$O. NaOH (0.0085 mmol) was then added as the separation promoting agent. When examining the result obtained after acquiring a 90° spectrum in Boltzmann equilibrium conditions, it can be seen that NaOH addition leads to a clear difference in the chemical shift of the pyrazine resonance in the two different solvents.

The pyrazine $^1$H NMR signal, typically observed as a singlet in the previous experiments, appears now as a sharp, narrow peak (corresponding to the ligand dissolved in the organic phase) and a low-intensity, broad resonance, shifted downfield from the former, corresponding to the substrate present in the aqueous phase (Figure S8).

When examining the analogous spectra acquired after SABRE hyperpolarisation, the chemical shift difference cannot be observed if the measurement is performed immediately after the polarisation transfer step, due to the extreme line broadening artefacts introduced by the fact that the data is acquired during the stabilisation of the mixture (motion artefacts). However, is the mixture is allowed to separate prior to data acquisition, the chemical shift difference between the resonances of the ligand dissolved in the organic and inorganic phase can be clearly detected (Figure S9).

Figure S9. Pyrazine signal acquired hyperpolarised under SABRE immediately after the polarisation transfer step (top) and 30 seconds after the polarisation transfer step (bottom) when complete separation has occurred.

Sample: 1-Fold Excess Pyrazine+Na$_2$CO$_3$ (3b)

A sample was prepared using 1-fold excess of ligand to 5 mM of Ir dissolved in a mixture of 0.3 ml CDCl$_3$ and 0.3 D$_2$O. Na$_2$CO$_3$ was added as a separation agent. When examining the result obtained after acquiring a 90 spectrum in Boltzmann equilibrium conditions, it can be seen that, similarly to the data presented above, a chemical shift separation of the pyrazine resonance as a function of solvent is seen.

The chemical shift difference is preserved in the $^1$H hyperpolarised spectrum acquired after the mixture is allowed to separate. However, as Na$_2$CO$_3$ is a much milder base (pK$_b$ 3.67) when compared to NaOH (pK$_b$ 0.2). The two substrate resonances appear much narrower and closer together (Figure S10).

Figure S10. $^1$H NMR spectrum of pyrazine acquired in thermal equilibrium conditions (x512).

Figure S11. $^1$H NMR spectrum of 3b hyperpolarised under SABRE, acquired immediately after the polarisation transfer step (middle) and 30 seconds after the polarisation transfer step (bottom) when complete separation has occurred.

Sample: 1-Fold Excess Pyrazine+NaHCO$_3$ (3c)

A sample was prepared using 1-fold excess of ligand to 5 mM of Ir dissolved in a mixture of 0.3 ml CDCl$_3$ and 0.3 D$_2$O. NaHCO$_3$ was added as a separation agent. When examining the result obtained after acquiring a 90° spectrum in Boltzmann equilibrium conditions, a chemical shift separation similar to the examples presented above can be detected (Figure S12).

Figure S12. $^1$H NMR spectrum of 3c acquired in thermal equilibrium conditions (x512).

The analogous spectrum acquired in hyperpolarised conditions after the mixture was allowed to separate exhibits several resonances instead of the two observed previously (Figure S13).

Figure S13. $^1$H NMR spectrum of 3c hyperpolarised under SABRE, acquired immediately after the polarisation transfer step (top) and 30 seconds after the polarisation transfer step (bottom) when complete separation has occurred.

Sample: 1-Fold Excess Pyrazine+$CH_3COO^-Na^+$ (3d)

A sample was prepared using 1-fold excess of ligand to 5 mM of Ir dissolved in a mixture of 0.3 ml $CDCl_3$ and 0.3 $D_2O$. $NaCO_3CH_3$ was added as a separation agent. The use of an acidic additive again leads to a difference in the chemical shift of the pyrazine resonances as a function of solvent pH.

Figure S14. $^1$H NMR spectrum of 3d acquired in thermal equilibrium conditions (x512).

Figure S15. $^1$H NMR spectrum of 3d hyperpolarised under SABRE, acquired immediately after the polarisation transfer step (top) and 30 seconds after the polarisation transfer step (bottom) when complete separation has occurred.

Sample: 1-Fold Excess Pyrazine+$CH_3COO$-$NH_4$+(3e)

A sample was prepared using 1-fold excess of ligand to 5 mM of Ir dissolved in a mixture of 0.3 ml $CDCl_3$ and 0.3 $D_2O$. $NH_4CO_3CH_3$ was added as a separation agent. The $^1$H spectrum acquired in thermal equilibrium conditions exhibits two sharp resonances accompanied by a very broad peak located downfield (Figure S16).

Figure S16. $^1$H NMR spectrum of 3e acquired in thermal equilibrium conditions (x512).

Figure S17. $^1$H NMR spectrum of 3e hyperpolarised under SABRE, acquired 30 seconds after the polarisation transfer step, when complete separation has occurred.

Sample: 1-Fold Excess Pyrazine+$Cl^-NH_4$+(3f)

Figure S18. Pyrazine signal acquired in Boltzmann equilibrium conditions (top, x256) and hyperpolarised under SABRE, acquired immediately after the polarisation transfer step (middle) and 30 seconds after the polarisation transfer step (bottom) when complete separation has occurred.

Sample: 17-Fold Excess Pyrazine+$NH_4Cl$+NaCl (3g)

Figure S19. Pyrazine signal acquired in Boltzmann equilibrium conditions (top, x 256) and hyperpolarised under SABRE acquired 30 seconds after the polarisation transfer step (bottom) when complete separation has occurred.

2. 1D MRI Results 2.1 SABRE hyperpolarisation of pyrazine in $CDC_3/D_2O$ mixtures Results obtained for a mixture of 0.020 ml $CDCl_3$ and 0.580 ml $D_2O$ are shown in Figures S20 and S21.

2.2 SABRE Hyperpolarisation of Pyrazine in $CDCl_3/D_2O$ Mixtures in the Presence of NaCl Sample: 1-Fold Excess Pyrazine Dissolved in 0.4 ml $CDCl_3$+0.2 ml $D_2O$+1 mg NaCl (2b).

Results are shown in Figures S22 and S23.

Sample: 1-Fold Excess Pyrazine Dissolved in 0.3 ml $CDCl_3$+0.3 ml $D_2O$+1 mg NaCl (2c).

Results are shown in Figures S24 and S25.

Sample: 1-Fold Excess Pyrazine Dissolved in 0.2 ml $CDCl_3$+0.4 ml $D_2O$+1 mg NaCl (2d).

Results are shown in Figures S26 and S27.

Sample: 1-Fold Excess Pyrazine Dissolved in 0.1 ml $CDCl_3$+0.5 ml $D_2O$+1 mg NaCl (2e).

Results are shown in Figures S28 and S29.

Sample: 1-Fold Excess Pyrazine Dissolved in 0.25 ml $CDCl_3$+0.35 ml $D_2O$+0.5 Mg NaCl (2f).

Results are shown in Figures S30 and S31.

Sample: 17-Fold Excess Pyrazine Dissolved in 0.3 ml $CDCl_3$+0.3 ml $D_2O$+1 mg NaCl (2g).

Results are shown in Figures S32 and S33.

Sample: 17-Fold Excess Pyrazine Dissolved in 0.3 ml $CDCl_3$+0.3 ml $D_2O$+2 mg NaCl (2h).

Results are shown in Figures S34 and S35.

Sample: 17-fold excess pyrazine dissolved in 0.3 ml $CDCl_3$+0.3 ml $D_2O$+2 mg NaCl+50 µl EtOD (2i).

Results are shown in Figures S36 and S37.

2.3 SABRE Hyperpolarisation of Pyrazine in $CDCl_3/D_2O$ Mixtures in the Presence of Other Salts.

Sample: 1-Fold Excess Pyrazine Dissolved in 0.3 ml $CDC_{13}$+0.3 ml $D_2O$+0.35 mg NaOH (3a).

Results are shown in Figures S38 and S39.

Sample: 1-Fold Excess Pyrazine Dissolved in 0.3 ml $CDCl_3$+0.3 ml $D_2O$+1 mg $Na_2CO_3$ (3b).

Results are shown in Figures S40 and S41.

Sample: 1-Fold Excess Pyrazine Dissolved in 0.3 ml $CDC_{13}$+0.3 ml $D_2O$+0.7 mg $NaHCO_3$ (3c).

Results are shown in Figures S42 and S43.

Sample: 1-Fold Excess Pyrazine Dissolved in 0.3 ml $CDC_{13}$+0.3 ml $D_2O$+0.57 mg $Na^+CH_3COO^-$ (3d).

Results are shown in Figures S44 and S45.

Sample: 1-Fold Excess Pyrazine Dissolved in 0.3 ml $CDCl_3$+0.3 ml $D_2O$+0.6 mg $NH_4^+CH_3COO^-$ (3e).

Results are shown in Figures S46 and S47.

Sample: 1-Fold Excess Pyrazine Dissolved in 0.3 ml $CDCl_3$+0.3 ml $D_2O$+0.5 mg $NH_4Cl$(3f).

Results are shown in Figures S48 and S49.

Sample: 17-Fold Excess Pyrazine Dissolved in 0.3 ml $CDCl_3$+0.3 ml $D_2O$+0.5 mg $NH_4Cl$+1 mg NaCl (3g).

Results are shown in Figures S50 to S52.

2.4 SABRE Hyperpolarisation of Other Substrates in $CDC_3/D_2O$ Mixtures.

In order to demonstrate that the approach of CASH SABRE is widely extendable to a whole range of substrates, we have performed hyperpolarisation experiments on a set of samples prepared using a 1:1 organic:aqueous phase ratio and a series of ligands which present significant interest in terms of biomedical applications. The ligands analysed are presented in Scheme S1.

Scheme S1. Substrates tested to prove the wide applicability of the CASH SABRE method.

a).

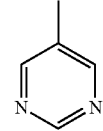

b).

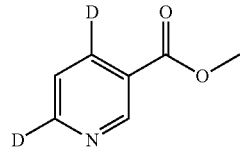

c).

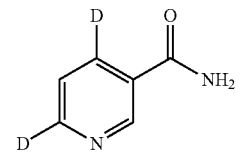

-continued d).

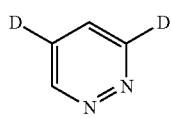

a). 5-methylpyridine, b). d$_2$-methylnicotinate, c). d$_2$-nicotinamide, d). d$_2$-pyridazine.

Sample: 1-Fold Excess 5-Methylpyrimidine Dissolved in 0.3 ml CDCl$_3$+0.3 ml D$_2$O+0.5 mg NaCl.
 Results are shown in Figures S53 and S54.
Sample: 1-Fold Excess 5-Methylpyrimidine Dissolved in 0.3 ml CDCl$_3$+0.3 ml D$_2$O+2 mg NaCl+20 µl EtOD.
 Results are shown in Figures S55 and S56.
Sample: 1-Fold Excess 5-Methylpyrimidine Dissolved in 0.3 ml CDCl$_3$+0.3 ml D$_2$O+2 mg NaCl+40 µl EtOD.
 Results are shown in Figures S57 and S58.
Sample: 1-Fold Excess d$_2$-Pyridazine Dissolved in 0.3 ml CDC$_{13}$+0.3 ml D$_2$O+1.0 Mg NaCl.
 Results are shown in Figures S59 and S60.
Sample: 1-Fold Excess d$_2$-Methylnicotinate Dissolved in 0.3 ml CDCl$_3$+0.3 ml D$_2$O+1.0 mg NaCl.
 Results are shown in Figures S61 and S62.
Sample: 1-Fold Excess d$_2$-Nicotinamide Dissolved in 0.3 ml CDCl$_3$+0.3 ml D$_2$O+1.0 mg NaCl.
 Results are shown in Figures S63 and S64.
Sample: 7-Fold Excess Pyrazine Dissolved in 0.3 ml CDCl$_3$+0.3 ml D$_2$O+3 mg NaCl (3h).
 Results are shown in Figures S65 and S66.
3. 2D MRI Results
3.1 2D MRI of SABRE Hyperpolarised Pyrazine in CDCl$_3$/D$_2$O Mixtures in the Presence of NaCl.
 Prior to 2D data acquisition, 1D projections of the signal derived from the hyperpolarised protons of pyrazine have been acquired on samples prepared with 1-fold excess of ligand, 17-fold excess of ligand and 17-fold excess of ligand in the presence of 50 µl of EtOD. The results are presented in Figure S65.
 The data show that in the absence of EtOD the pyrazine is uniformly distributed in both CDCl$_3$ and D$_2$O, with average ratios of 8:3 for the sample containing 1 fold excess and 5:1.5 for the sample containing 17-fold excess. EtOD addition promotes the transition of the ligand dissolved in CDCl$_3$ towards the interface with D$_2$O (Figure S66).
 2D images of the samples have been acquired using a RARE protocol with centric k-space sampling in thermal equilibrium conditions and after 10 s of shaking in the stray field of the magnet in the presence of p-H$_2$. The results are depicted in Figures S67 to S69.
 In order to assess the evolution of the hyperpolarised signal as a function of time in both phases, gradient echo images acquired using a low flip angle pulse for excitation have been acquired each 0.8 s after the hyperpolarisation step. The results, presented in Figure S70 and S71, show that, in a first instance, a more intense signal is obtained in the CDCl$_3$ phase. After longer acquisition times, the signal intensity in the D$_2$O phase becomes comparable with that of the signal in the CDCl$_3$ phase, demonstrating the continuous diffusion of hyperpolarised pyrazine in water.
 It is worth noting that, in the sample containing EtOD, the highest signal intensity is obtained at the interface, as previously shown by the 1D projections. This reflects the possibility of using SABRE in the study of interface processes in multi-phase systems.

3.2 2D MRI of SABRE Hyperpolarised Pyrazine in CDCl$_3$/D$_2$O Mixtures in the Presence of Other Salts.
 Prior to 2D data acquisition, 1D projections of the signal derived from the hyperpolarised protons of pyrazine have been acquired on samples 3f and 3g, prepared with 1-fold excess of ligand and 3.3 mg NH$_4^+$CH$_3$COO$^-$, and 17-fold excess of ligand and 3.3 mg NH$_4^+$CH$_3$COO$^-$+1 mg NaCl respectively. The results are presented in Figure S72.
 2D images of the samples have been acquired using a RARE protocol with centric k-space sampling in thermal equilibrium conditions and after 10 s of shaking in the stray field of the magnet in the presence of p-H$_2$. The results are depicted in Figure S73 for the sample prepared with a 1-fold excess of pyrazine and Figure S74 for the sample prepared with 17-fold excess of pyrazine.
4. Quality Control by UV-Vis
 Figure S75 provides (a) UV-visible spectrum of chloroform layer after dilution (100 times). In this layer the catalyst characterized by two absorption bands at $\lambda_1$=374 nm ($\varepsilon$=6800 l·mol$^{-1}$·cm$^{-1}$) and $\lambda_2$=500 nm ($\varepsilon$=2200 l·mol$^{-1}$·cm$^{-1}$) and pyrazine at $\lambda_1$=261 nm. (b) UV-visible of D$_2$O layer after dilution of 10 times. In this layer, the pyrazine was the main product.
Example Results to Illustrate the SABRE-Biphasic Method.
5. Pyrazine (pz)
5.1 in CD$_3$Cl/D$_2$O in the Ratio 0.3:0.3
 A sample was prepared using a 4-fold excess of pyrazine (pz) relative to the iridium catalyst IrCl(COD)(IMes-d$_{22}$) at a 5 mM level in a mixture of 0.3 ml of CDCl$_3$ and 0.3 ml of D$_2$O. NaCl (0.017 mmol) was then added to promote phase separation. The NMR result after the application of a 90 r.f. pulse to H at Boltzmann equilibrium conditions is shown in Figure S78. When compared to the hyperpolarised result it can be seen that the pyrazine substrate exhibits a signal enhancement of 1500 fold per proton nucleus.
5.2 in CD$_2$Cl$_2$/D$_2$O in the Ratio 0.3/0.3
 An analogous sample was prepared using a 4-fold excess of pyrazine (pz) relative to IrCl(COD)(IMes-d$_{22}$) (5 mM) in a mixture of 0.3 ml CD$_2$Cl$_2$ and 0.3 ml of D$_2$O. NaCl (0.017 mmol) was again added. The hyperpolarisation process now resulted in a pyrazine enhancement level of 1300 fold per proton and we therefore illustrate the process whereby solvent variation can be used to improve the level of signal gain (Figure S2). Figure S79 details the corresponding profile which established that pyrazine hyperpolarisation is exhibited in the aqueous phase.
6. SABRE Hyperpolarisation of 3-Fluoropyridine, Pyridazine and 4-Aminopyridine as Further Examples

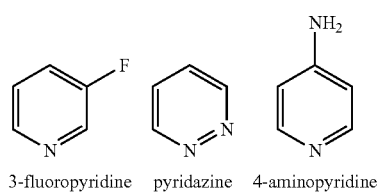

3-fluoropyridine    pyridazine    4-aminopyridine 6.1 3-Fluoropyridine in CD$_3$Cl/D$_2$O in the Ratio 0.3:0.3
 A sample was prepared using a 10-fold excess of 3-fluoropyridine relative to the IMes iridium catalyst (5 mM) in a mixture of 0.3 ml CDCl$_3$ and 0.3 ml of D$_2$O. NaCl (0.017 mmol) was added as the phase separation promoter. It can again be seen that 3-fluoropyridine is hyperpolarised in the water phase (Figures S81 and S82).

3-fluoropyridine is highly soluble in organic solvent such as $CD_3C$ or $CD_2Cl_2$. As a consequence, 3-fluoropyridine was enhanced much better in organic phase rather aqueous phase (Figure S82).

6.2 Pyridazine in $CD_3Cl/D_2O$ in the Ratio 0.3:0.3

A sample was prepared using a 4-fold excess of pyridazine relative to the IMes iridium catalyst (5 mM) in a mixture of 0.3 ml $CDCl_3$ and 0.3 ml $D_2O$. NaCl (0.017 mmol) was then added as the phase separation promoting agent. When examining the results obtained after acquiring appropriate NMR spectra it can be seen that pyridazine is hyperpolarised in the water phase (Figures S83 and S84).

6.3 Pyridazine in $CD_2Cl_2/D_2O$ in the Ratio 0.3:0.3

A sample was prepared using a 4-fold excess of pyridazine relative to the IMes iridium catalyst (5 mM) in a mixture of 0.3 ml of $CD_2Cl_2$ and 0.3 ml of $D_2O$. NaCl (0.017 mmol) was then added as the phase separation promoting agent. When examining the hyperpolarised NMR results it can be seen that pyridazine is hyperpolarised in water phase (Figure S85).

6.4 Pyridazine in n-Butanol/$D_2O$ in the Ratio 0.2:0.5

A sample was prepared using a 10-fold excess of pyridazine relative to the IMes iridium catalyst (5 mM) in a mixture of 0.2 ml n-butanol and 0.5 ml $D_2O$. NaCl (0.34 mmol) was then added as the phase separation promoting agent. When examining the hyperpolarisation study results it can be seen that pyridazine is hyperpolarised in the water phase. Here n-butanol acts as solvent that is poorly miscible with water. In this experiment, water is now the lower layer and n-butanol the upper layer. The reported NMR measurements now reflect a direct examination of the water phase because of the coil orientation.

6.5 4-Aminopyridine in $CD_2Cl_2/D_2O$ in the Ratio 0.3:0.3

4-aminopyridine is a fully water soluble substrate. To be hyperpolarised, a co-solvent such as ethanol was required to increase the solubility of 4-aminopyridine in organic phase where the catalyst and $pH_2$ are presenting.

A sample was prepared using a 10-fold excess of 4-aminopyradizine relative to the IMes iridium catalyst (5 mM) in a mixture of 0.25 ml of $CD_2Cl_2$, 0.1 ml of EtOD and 0.35 ml of $D_2O$. NaCl (0.034 mmol) was then added as the phase separation promoting agent. When examining the results obtained after hyperpolarisation, it can be seen that 4-aminopyridine is hyperpolarised in the water phase (Figure S87).

7. Optimisation of the SABRE-Biphasic Hyperpolarisation of $d_2$-Nicotinamide and $d_2$-Methylnicotinate

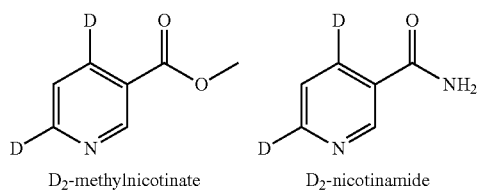

D₂-methylnicotinate            D₂-nicotinamide 7.1 $d_2$-Nicotinamide in $CD_3Cl/D_2O$ in the Ratio 0.3:0.3

A sample was prepared using a 10-fold excess of d2-nicotinamide relative to the IMes iridium catalyst (5 mM) in a mixture of 0.3 ml CD3Cl and 0.3 ml D2O. NaCl (0.24 mmol) was then added as the phase separation promoting agent. When examining the results obtained it can be seen that d2-nicotinamide is hyperpolarised in the water phase (Figure S88).

$D_2$-nicotinamide is full water soluble substrate and partially soluble in organic solvent such as $CD_2Cl_2$ or $CD_3Cl$. High enhancement of $d_2$-nicotinamide was observed in aqueous phase when $D_2O$ layer is containing at least 4.5% (weight) of NaCl as indicated in Figure S90.

7.2 $d_2$-Nicotinamide in a n-Butanol/$D_2O$ Sample of Ratio 0.2:0.5

A sample was prepared using a 4-fold excess of $d_2$-nicotinamide relative to the IMes iridium catalyst (5 mM) in a mixture of 0.2 ml of n-butanol and 0.5 ml of $D_2O$. NaCl (0.29 mmol) was then added as the phase separation promoting agent. The resulting $d_2$-nicotinamide signal was now hyperpolarised in the water phase after SABRE transfer (Figure S91).

7.3 $d_2$-Nicotinamide in $CD_2Cl_2/D_2O$ Solution in the Ratio 0.3:0.3

A sample was prepared using a 10-fold excess of $d_2$-nicotinamide relative to the IMes iridium catalyst (5 mM) in a mixture of 0.3 ml of $CD_2Cl_2$ and 40 μl of $D_2O$. After activation by 3 bar $H_2$ overnight, NaCl (0.24 mmol) as the separation promoting agent in 0.26 ml of $D_2O$ was added to the activated solution. The results reveal that $d_2$-nicotinamide is hyperpolarised in the water phase.

7.4 $d_2$-Methylnicotinate in $CD_3Cl$(0.3 ml) then Extracted by Acidified (pH~3) $D_2O$ (0.3 ml) Solution $D_2$-methylnicotinate is fully soluble in $CD_3Cl$ phase and partially soluble in $D_2O$ phase. When the direct biphasic SABRE method ($CD_3Cl/D_2O$+NaCl) is applied to hyperpolarise $d_2$-methynicotinade.

When a sample was prepared using a 4-fold excess of $d_2$-methylnicotinate (relative to the IMes iridium catalyst 5 mM) in a mixture of 0.3 ml of $CD_3Cl$ and 0.3 ml of $D_2O$ in presence NaCl (0.017 mmol as the phase separation promoting agent), weak enhancement was observed in water layer however in $CD_3Cl$ layer a high enhancement was clearly seen (Figure S93).

Here we exemplify a method to promote aqueous phase separation when the agent prefers the non-aqueous phase. It involves acidification. A sample was prepared using a 10-fold excess of $d_2$-methylnicotinate relative to the IMes iridium catalyst (5 mM) in 0.3 ml $CD_3Cl$. The catalyst was then activated by adding 3 bar of $H_2$ and leaving it overnight at 298 K. When $pH_2$ was then used, the $d_2$-methylnicotinate signal proved to be enhanced by 2500 fold per proton through SABRE. Immediately, 0.3 ml of $D_2O$ containing 1 μl of HCl was added to the hyperpolarised $d_2$-methylnicotinate solution and the sample shaken to promote phase separation. Upon phase separation it could be established that hyperpolarised $d_2$-methylnicotinate is visible in the water phase.

8. Hyperpolarisation of $^3C$, $^{15}N$ of Pyrazine

Hence we believe that this new and simple Biphasic Hyperpolarisation via Signal Amplification By Reversible Exchange (Biphasic-SABRE) approach reflects an exciting route to produce high levels of hyperpolarisation in a biocompatible aqueous medium without catalyst contamination. We have demonstrated $^1H$, $^{13}C$ and $^{15}N$ detection is possible in water phases via biphasic-SABRE.

A sample was prepared using a 20-fold excess of pyrazine (pz) relative to the IMes iridium catalyst (5 mM) in a mixture of 0.3 ml of $CDCl_3$ and 0.3 ml of $D_2O$. NaCl (0.34 mmol) was then added to promote phase separation. When the high-resolution $^{13}C$ and $^{15}N$ responses of pz are examined, strong signals are detected in the aqueous and chloroform phases at different frequencies (Figure S96, 180- and 3000-fold enhancements, respectively).

9.0 2D MRI of SABRE Hyperpolarised Pyridazine in $CDCl_3/D_2O$ Mixtures in the Presence of NaCl.

We also explored the MRI detection of hyperpolarised pyridazine, which, as previously shown, tends to successfully concentrate in the aqueous phase, thus making this substrate a good candidate for in vivo MRI applications. 2D images of a sample containing 7-fold excess pyridazine have been acquired using a RARE protocol. The results, presented in Figure S97, show that, after phase separation, excellent signal enhancement can be detected in the aqueous phase (top of the tube, see sagittal image) and almost no hyperpolarised pyridazine response is present in the organic phase.

10. Quality Control by UV-Vis and Transport Between the Phases

A UV spectrum was recorded to monitor the amount of catalyst present in the aqueous phase 10 seconds after mixing. As detailed in Figure S98 no signal is seen which places an upper limit of $1.5 \times 10^{-6}$ mol $dm^{-3}$ on the iridium concentration based on $[Ir(H)_2(IMes)(pz)_3]Cl$. The sample used mimicked that of 5.1.

Relative rates of pz transfer from the aqueous phase into chloroform were assessed, with, and without NaCl, by UV monitoring as detailed in Figure S100. This involved layering a sample of $H_2O$ containing pyrazine over an equivalent volume of $CHCl_3$ that contained no pz. It appears that while the relative partitioning of pz between these phases was unaffected by added NaCl (within the error of a control measurement) but the presence of NaCl was found to increase the rate of pz transfer between the phases.

REFERENCES

[1] J. H. Ardenkjær-Larsen, B. Fridlund, A. Gram, G. Hansson, L. Hansson, M. H. Lerche, R. Servin, M. Thaning, K. Golman, *Proceedings of the National Academy of Sciences* 2003, 100, 1015-10163.
[2] C. R. Bowers, D. P. Weitekamp, *Journal of the American Chemical Society* 1987, 109, 5541-5542.
[3] T. C. Eisenschmid, R. U. Kirss, P. P. Deutsch, S. I. Hommeltoft, R. Eisenberg, J. Bargon, R. G. Lawler, A. L. Balch, *Journal of the American Chemical Society* 1987, 109, 8089-8091.
[4] R. W. Adams, J. A. Aguilar, K. D. Atkinson, M. J. Cowley, P. I. P. Elliott, S. B. Duckett, G. G. R. Green, I. G. Khazal, J. Lopez-Serrano, D. C. Williamson, *Science* 2009, 323, 1708-1711.
[5] K. D. Atkinson, M. J. Cowley, P. I. P. Elliott, S. B. Duckett, G. G. R. Green, J. Lopez-Serrano, A. C. Whitwood, *Journal of the American Chemical Society* 2009, 131, 13362-13368.
[6] R. W. Adams, S. B. Duckett, R. A. Green, D. C. Williamson, G. G. R. Green, *The Journal of Chemical Physics* 2009, 131, 194505.
[7] J. Kurhanewicz, D. B. Vigneron, K. Brindle, E. Y. Chekmenev, A. Comment, C. H. Cunningham, R. J. DeBerardinis, G. G. Green, M. O. Leach, S. S. Rajan, R. R. Rizi, B. D. Ross, W. S. Warren, C. R. Malloy, *Neoplasia* 2011, 13, 81-97.
[8] aM. A. Schroeder, H. J. Atherton, L. C. Heather, J. L. Griffin, K. Clarke, G. K. Radda, D. J. Tyler, *Nmr in Biomedicine* 2011, 24, 980-987; bB. Pullinger, H. Profka, J. H. Ardenkjaer-Larsen, N. N. Kuzma, S. Kadlecek, R. R. Rizi, *Nmr in Biomedicine* 2012, 25, 1113-1118; cT. H. Witney, K. M. Brindle, *Biochemical Society Transactions* 2010, 38, 1220-1224; dE. Y. Chekmenev, J. Hoevener, V. A. Norton, K. Harris, L. S. Batchelder, P. Bhattacharya, B. D. Ross, D. P. Weitekamp, *Journal of the American Chemical Society* 2008, 130, 4212-+.
[9] M. J. Cowley, R. W. Adams, K. D. Atkinson, M. C. R. Cockett, S. B. Duckett, G. G. R. Green, J. A. B. Lohman, R. Kerssebaum, D. Kilgour, R. E. Mewis, *Journal of the American Chemical Society* 2011, 133, 6134-6137.
[10] R. E. Mewis, K. D. Atkinson, M. J. Cowley, S. B. Duckett, G. G. R. Green, R. A. Green, L. A R. Highton, D. Kilgour, L. S. Lloyd, J. A. B. Lohman, D. C. Williamson, *Magnetic Resonance in Chemistry* 2014, 52, 358-369.
[11] P. Spannring, I. Reile, M. Emondts, P. P. M. Schleker, N. K. J. Hermkens, N. G. J. van der Zwaluw, B. J. A. van Weerdenburg, P. Tinnemans, M. Tessari, B. Blumich, F. Rutjes, M. C. Feiters, *Chemistry—a European Journal* 2016, 22, 9277-9282.
[12] aF. Shi, P. He, Q. A. Best, K. Groome, M. L. Truong, A. M. Coffey, G. Zimay, R. V. Shchepin, K. W. Waddell, E. Y. Chekmenev, B. M. Goodson, *Journal of Physical Chemistry C* 2016, 120, 12149-12156; bM. Fekete, C. Gibard, G. J. Dear, G. G. R. Green, A. J. J. Hooper, A. D. Roberts, F. Cisnetti, S. B. Duckett, *Dalton Transactions* 2015, 44, 7870-7880; cH. F. Zeng, J. D. Xu, M. T. McMahon, J. A. B. Lohman, P. C. M. van Zijl, *Journal of Magnetic Resonance* 2014, 246, 119-121.
[13] Francesca Reineri, Alessandra Viale, Giovanbattista Giovenzana, Daniela Santelia, Walter Dastru, Roberto Gobetto, and Silvio Aime, *Journal of the American Chemical Society* 2008, 130, 15047-15053.
[14] Francesca Reineri, Tommaso Boi & Silvio Aime, *Nature Communications*, 6:5858.

The invention claimed is:

1. A method for the preparation of an aqueous imaging medium, said method comprising the steps of:
   (i) preparing a multiphasic solvent system comprising an aqueous component and a non-aqueous component, said solvent comprising a target substrate and a SABRE hyperpolarisation transfer catalyst;
   (ii) adding parahydrogen (p-$H_2$) gas to the solvent system;
   (iii) agitating the solvent system to form an emulsion or mixture comprising the aqueous component and the non-aqueous component thereby transferring the spin order from the hyperpolarisation transfer catalyst to the target substrate;
   (iv) if the target substrate is in the non-aqueous component adjusting the pH to extract the target substrate into the aqueous component;
   (v) adding a solvent phase-separation promoter; and
   (vi) simultaneously with the formation of a hyperpolarised target substrate separating the non-aqueous component and the aqueous component wherein the aqueous component contains the hyperpolarised target substrate and provides an aqueous imaging medium.

2. A method according to claim 1 wherein the multiphasic solvent system is a biphasic solvent system.

3. A method according to claim 1 wherein the target substrate and the SABRE hyperpolarisation transfer catalyst are in the non-aqueous component and the pH and the temperature are adjusted to allow the target substrate to be extracted into the aqueous component after hyperpolarisation has transferred to the target substrate.

4. A method according to claim 3 wherein the pH is adjusted by the addition of salts or organic species.

5. A method according to claim 1 wherein the target substrate is in both the aqueous component and the non-aqueous component while the SABRE hyperpolarisation transfer catalyst resides mainly or solely in the non-aqueous component.

6. A method according to claim 1 wherein the non-aqueous component comprises a solvent that is immiscible with water.

7. A method according to claim 6 wherein the water immiscible solvent is an aromatic solvent or a halogenated hydrocarbon solvent.

8. A method according to claim 7 wherein the water immiscible solvent is selected from the group consisting of benzene, toluene, chloroform, dichloromethane n-butanol, methyl-t-butyl ether, ethyl acetate and 2-butanone.

9. A method according to claim 1 wherein the aqueous component includes a co-solvent.

10. A method according to claim 1 wherein the SABRE hyperpolarisation transfer catalyst is a homogeneous catalyst selected from the group consisting of rhodium based catalysts and iridium based catalysts.

11. A method according to claim 1 wherein the SABRE hyperpolarisation transfer catalyst is a heterogeneous catalyst selected from the group consisting of one or more platinum group metals or non-precious metal catalysts.

12. A method according to claim 1 wherein the SABRE hyperpolarisation transfer catalyst is Ir(CI(COD)IMes or analogues thereof or a $^2$H-labelled counterpart of Ir(CI(COD)IMes.

13. A method according to claim 1 wherein the SABRE hyperpolarisation transfer catalyst is selected from the group consisting of:

IMes

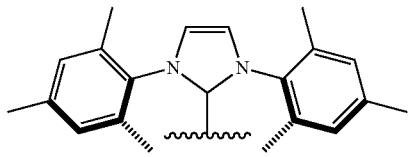

para

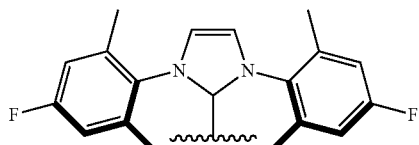

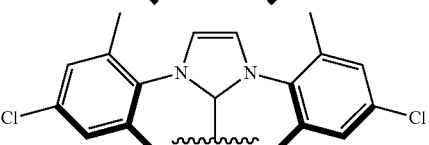

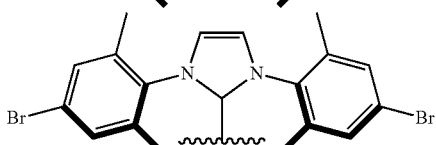

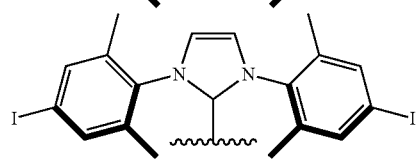

-continued

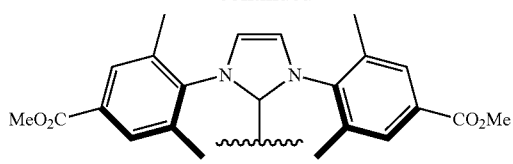

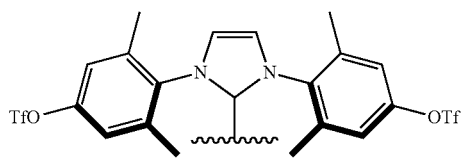

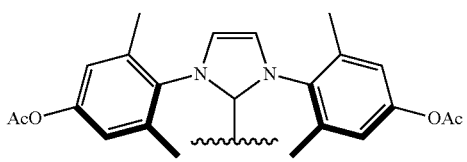

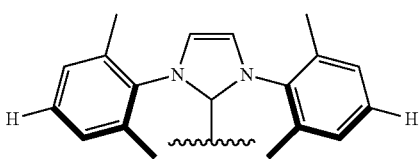

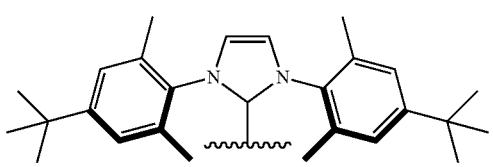

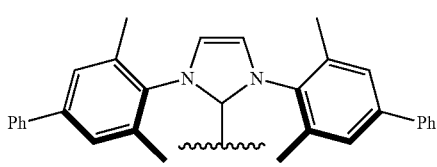

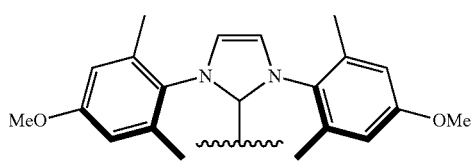

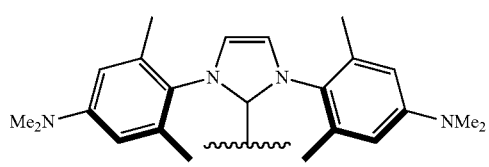

meta

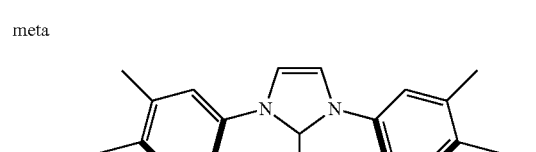

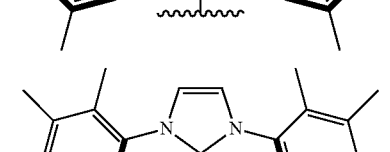

33
-continued
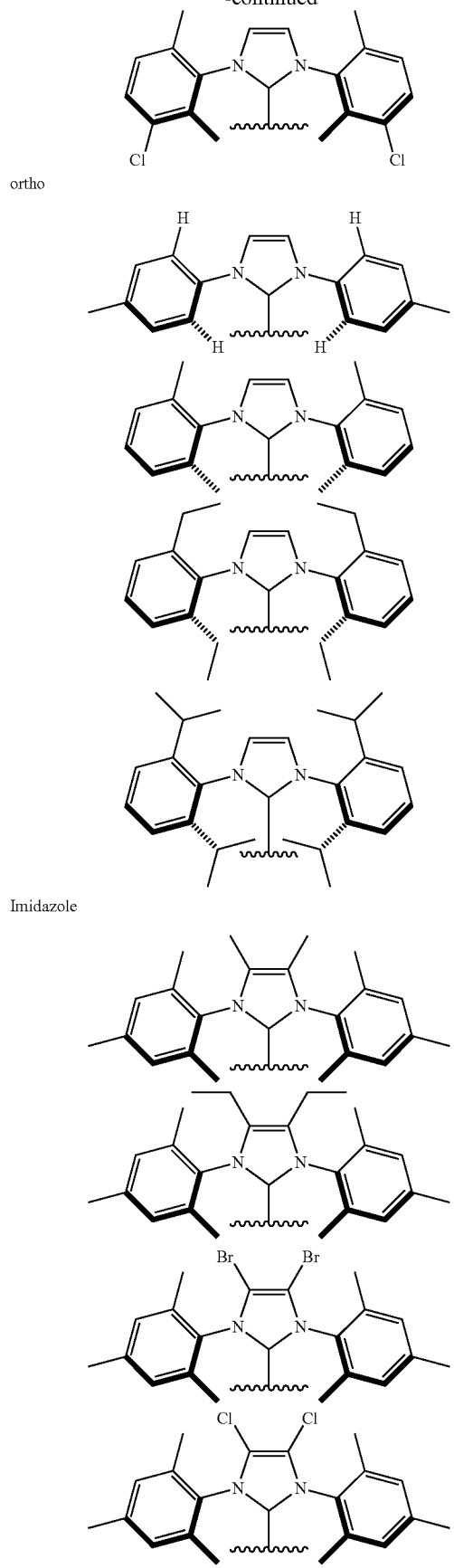
ortho
Imidazole
34
-continued
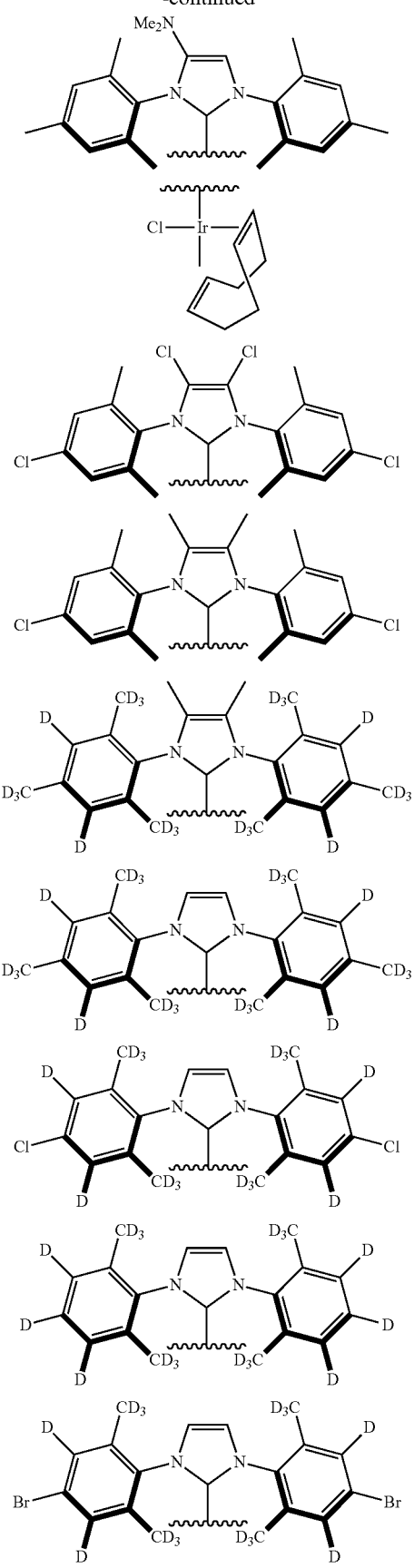

-continued

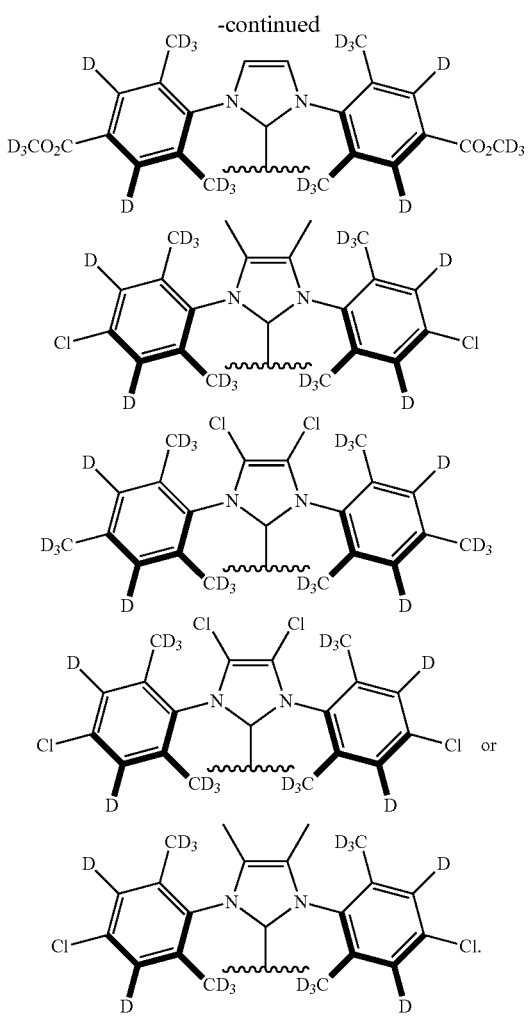

14. A method according to claim 1 wherein the target substrate will contain at least one spin 1/2 nuclei and wherein the at least one spin 1/2 nuclei is selected from the group consisting of $^1H$, $^{13}C$, $^{31}P$, $^{15}N$, $^{29}Si$ and $^{19}F$.

15. A method according to claim 1 wherein the target substrate contains appropriate $^2H$, O or Cl labels to maximise the relaxation times of the nuclei spins that are to be hyperpolarised.

16. A method according to claim 1 wherein the target substrate comprises one or more of nicotinamide, nicotine, pyrazine, 5-methyl pyrimidine or any suitable reagent, or mixture of reagents, that is known in the art to be capable of being hyperpolarised through SABRE, to produce an appropriate concentration of substrate for detection.

17. A method according to claim 1 wherein the phase-separation promoter is an alkali metal salt or an alkaline earth metal salt.

18. A method according to claim 1 wherein the phase-separation promoter is an alcohol.

19. A method of producing a hyperpolarised target substrate in an aqueous imaging medium, said method comprising the steps of:
   (i) preparing a multiphasic solvent system comprising an aqueous component and a non-aqueous component, said solvent comprising a target substrate and a SABRE hyperpolarisation transfer catalyst;
   (ii) adding parahydrogen (p-$H_2$) gas to the solvent system;
   (iii) agitating the solvent system to form an emulsion or mixture comprising the aqueous component and the non-aqueous component thereby transferring the spin order from the hyperpolarisation transfer catalyst to the target substrate;
   (iv) if the target substrate is in the non-aqueous component adjusting the pH to extract the target substrate into the aqueous component; and
   (v) adding solvent phase-separation promoter;
   (vi) separating the non-aqueous component and the aqueous component wherein the aqueous component contains the hyperpolarised target substrate and provides an aqueous imaging medium; and
   (vii) performing SABRE by creating a hyperpolarised agent with p-$H_2$ whilst agitating the mixture and simultaneously forming a hyperpolarised target substrate to provide an aqueous imaging medium.

20. A method according to claim 19 wherein the multiphasic solvent system is a biphasic solvent system.

* * * * *